US012639250B2

(12) United States Patent
Morgan et al.

(10) Patent No.: US 12,639,250 B2
(45) Date of Patent: May 26, 2026

(54) INTELLIGENT DATA PORTS FOR MODULAR ENERGY SYSTEMS

(71) Applicant: Cilag GmbH International, Zug (CH)

(72) Inventors: Joshua P. Morgan, Loveland, OH (US); Daniel C. Herman, Maineville, OH (US); Joshua M. Henderson, Montgomery, OH (US); Andrew W. Carroll, Cincinnati, OH (US); Eitan T. Wiener, Loveland, OH (US); Jeffrey L. Aldridge, Lebanon, OH (US)

(73) Assignee: Cilag GmbH International, Zug (CH)

( * ) Notice: Subject to any disclaimer, the term of this patent is extended or adjusted under 35 U.S.C. 154(b) by 781 days.

(21) Appl. No.: 17/217,397

(22) Filed: Mar. 30, 2021

(65) Prior Publication Data

US 2022/0318179 A1 Oct. 6, 2022

(51) Int. Cl.
*G06F 13/42* (2006.01)
*A61B 17/32* (2006.01)
(Continued)

(52) U.S. Cl.
CPC .. *G06F 13/4282* (2013.01); *A61B 17/320068* (2013.01); *A61B 18/12* (2013.01);
(Continued)

(58) Field of Classification Search
CPC .... G06F 13/4282; G06F 1/3253; G06F 21/44; A61B 17/320068; A61B 18/12; A61B 2018/00994; H02H 9/02
See application file for complete search history.

(56) References Cited

U.S. PATENT DOCUMENTS 4,171,700 A 10/1979 Farin
4,378,801 A 4/1983 Oosten
(Continued)

FOREIGN PATENT DOCUMENTS

EP 0408160 A1 1/1991
EP 0473987 A1 3/1992
(Continued)

OTHER PUBLICATIONS

Sorrells, P., "Application Note AN680. Passive RFID Basics," retrieved from http://ww1.microchip.com/downloads/en/AppNotes/00680b.pdf on Feb. 26/2020, Dec. 31, 1998, pp. 1-7.
(Continued)

*Primary Examiner* — Benjamin J Klein
*Assistant Examiner* — Thien Jason Tran
(74) *Attorney, Agent, or Firm* — Vorys, Sater, Seymour and Pease LLP

(57) ABSTRACT

Disclosed in an accessory circuit for a modular energy system. The accessory circuit includes an accessory port configured to receive an accessory, a power supply, a processor, an isolation barrier configured to electrically isolate the processor and the power supply from the accessory port. A flexible serial communication interface is coupled between the processor and the accessory port. The flexible serial communication interface is configured to support multiple communication protocols. A presence detection circuit is coupled between the accessory port and the processor. The presence detection circuit is configured to detect presence of an accessory connected to the accessory port.

17 Claims, 35 Drawing Sheets

(51) Int. Cl.

| | | |
|---|---|---|
| *A61B 18/00* | (2006.01) | |
| *A61B 18/12* | (2006.01) | |
| *G06F 1/3234* | (2019.01) | |
| *G06F 21/44* | (2013.01) | |
| *H02H 9/02* | (2006.01) | |

(52) U.S. Cl.
CPC ............ *G06F 1/3253* (2013.01); *G06F 21/44* (2013.01); *H02H 9/02* (2013.01); *A61B 2018/00994* (2013.01)

(56) References Cited

U.S. PATENT DOCUMENTS

| | | | |
|---|---|---|---|
| 4,640,279 | A | 2/1987 | Beard |
| 4,849,752 | A | 7/1989 | Bryant |
| D303,787 | S | 10/1989 | Messenger et al. |
| 5,041,110 | A | 8/1991 | Fleenor |
| D327,061 | S | 6/1992 | Soren et al. |
| 5,189,277 | A | 2/1993 | Boisvert et al. |
| 5,204,669 | A | 4/1993 | Dorfe et al. |
| 5,318,563 | A | 6/1994 | Malis et al. |
| 5,325,270 | A | 6/1994 | Wenger et al. |
| 5,383,880 | A | 1/1995 | Hooven |
| 5,395,033 | A | 3/1995 | Byrne et al. |
| 5,425,375 | A | 6/1995 | Chin et al. |
| 5,613,158 | A | 3/1997 | Savage |
| D379,346 | S | 5/1997 | Mieki |
| 5,667,517 | A | 9/1997 | Hooven |
| 5,690,504 | A | 11/1997 | Scanlan et al. |
| 5,693,042 | A | 12/1997 | Boiarski et al. |
| 5,724,468 | A | 3/1998 | Leone et al. |
| 5,788,688 | A | 8/1998 | Bauer et al. |
| 5,817,119 | A | 10/1998 | Klieman et al. |
| 5,849,020 | A | 12/1998 | Long et al. |
| 5,865,361 | A | 2/1999 | Milliman et al. |
| 5,872,481 | A | 2/1999 | Sevic et al. |
| 5,901,150 | A | 5/1999 | Jhuboo et al. |
| 5,910,139 | A | 6/1999 | Cochran et al. |
| 5,941,846 | A | 8/1999 | Duffy et al. |
| 6,019,745 | A | 2/2000 | Gray |
| 6,049,467 | A | 4/2000 | Tamarkin et al. |
| 6,055,062 | A | 4/2000 | Dina et al. |
| 6,055,458 | A | 4/2000 | Cochran et al. |
| D431,811 | S | 10/2000 | Nishio et al. |
| 6,172,875 | B1 | 1/2001 | Suzuki et al. |
| 6,179,136 | B1 | 1/2001 | Kluge et al. |
| 6,269,411 | B1 | 7/2001 | Reasoner |
| 6,273,750 | B1 | 8/2001 | Malkowski, Jr. |
| 6,288,606 | B1 | 9/2001 | Ekman et al. |
| H2037 | H | 7/2002 | Yates et al. |
| 6,416,471 | B1 | 7/2002 | Kumar et al. |
| 6,546,270 | B1 | 4/2003 | Goldin et al. |
| 6,584,358 | B2 | 6/2003 | Carter et al. |
| 6,601,124 | B1 | 7/2003 | Blair |
| 6,611,793 | B1 | 8/2003 | Burnside et al. |
| 6,731,514 | B2 | 5/2004 | Evans |
| 6,760,218 | B2 | 7/2004 | Fan |
| 6,775,715 | B2 | 8/2004 | Spitaels et al. |
| 6,839,238 | B2 | 1/2005 | Derr et al. |
| 6,843,657 | B2 | 1/2005 | Driscoll et al. |
| 6,888,848 | B2 | 5/2005 | Beshai et al. |
| 6,913,471 | B2 | 7/2005 | Smith |
| 7,009,511 | B2 | 3/2006 | Mazar et al. |
| 7,044,949 | B2 | 5/2006 | Orszulak et al. |
| 7,074,205 | B1 | 7/2006 | Duffy et al. |
| 7,134,994 | B2 | 11/2006 | Alpert et al. |
| 7,171,784 | B2 | 2/2007 | Eenigenburg |
| 7,217,269 | B2 | 5/2007 | El-Galley et al. |
| 7,252,664 | B2 | 8/2007 | Nasab et al. |
| 7,268,684 | B2 | 9/2007 | Tethrake et al. |
| 7,331,699 | B2 | 2/2008 | Gawalkiewicz et al. |
| 7,344,532 | B2 | 3/2008 | Goble et al. |
| 7,353,068 | B2 | 4/2008 | Tanaka et al. |
| D575,792 | S | 8/2008 | Benson |
| 7,408,439 | B2 | 8/2008 | Wang et al. |
| D579,876 | S | 11/2008 | Novotney et al. |
| D583,328 | S | 12/2008 | Chiang |
| 7,496,418 | B2 | 2/2009 | Kim et al. |
| D589,447 | S | 3/2009 | Sasada et al. |
| 7,500,747 | B2 | 3/2009 | Howell et al. |
| 7,518,502 | B2 | 4/2009 | Austin et al. |
| 7,563,259 | B2 | 7/2009 | Takahashi |
| 7,601,149 | B2 | 10/2009 | DiCarlo et al. |
| 7,637,907 | B2 | 12/2009 | Blaha |
| 7,656,671 | B2 | 2/2010 | Liu et al. |
| 7,695,485 | B2 | 4/2010 | Whitman et al. |
| 7,757,028 | B2 | 7/2010 | Druke et al. |
| D631,252 | S | 1/2011 | Leslie |
| 7,932,826 | B2 | 4/2011 | Fritchie et al. |
| 7,945,065 | B2 | 5/2011 | Menzl et al. |
| 7,945,342 | B2 | 5/2011 | Tsai et al. |
| 7,982,776 | B2 | 7/2011 | Dunki-Jacobs et al. |
| 7,995,045 | B2 | 8/2011 | Dunki-Jacobs |
| 8,019,094 | B2 | 9/2011 | Hsieh et al. |
| 8,057,492 | B2 | 11/2011 | Ortiz et al. |
| D655,678 | S | 3/2012 | Kobayashi et al. |
| D657,368 | S | 4/2012 | Magee et al. |
| 8,187,263 | B2 | 5/2012 | Behnke et al. |
| 8,218,279 | B2 | 7/2012 | Liao et al. |
| 8,239,066 | B2 | 8/2012 | Jennings et al. |
| D667,838 | S | 9/2012 | Magee et al. |
| D675,164 | S | 1/2013 | Kobayashi et al. |
| D676,392 | S | 2/2013 | Gassauer |
| D678,196 | S | 3/2013 | Miyauchi et al. |
| D678,304 | S | 3/2013 | Yakoub et al. |
| 8,423,182 | B2 | 4/2013 | Robinson et al. |
| D687,146 | S | 7/2013 | Juzkiw et al. |
| 8,504,136 | B1 | 8/2013 | Sun et al. |
| 8,540,709 | B2 | 9/2013 | Allen |
| 8,551,088 | B2 | 10/2013 | Falkenstein et al. |
| 8,567,393 | B2 | 10/2013 | Hickle et al. |
| 8,594,565 | B2 | 11/2013 | Satoh et al. |
| D704,839 | S | 5/2014 | Juzkiw et al. |
| 8,795,001 | B1 | 8/2014 | Lam et al. |
| 8,799,527 | B2 | 8/2014 | Mullins et al. |
| 8,819,581 | B2 | 8/2014 | Nakamura et al. |
| 8,840,609 | B2 | 9/2014 | Stuebe |
| D716,333 | S | 10/2014 | Chotin et al. |
| 8,911,437 | B2 | 12/2014 | Horlle et al. |
| 8,917,513 | B1 | 12/2014 | Hazzard |
| 8,920,186 | B2 | 12/2014 | Shishikura |
| 8,923,012 | B2 | 12/2014 | Kaufman et al. |
| 8,961,441 | B2 | 2/2015 | Cioanta et al. |
| 8,968,296 | B2 | 3/2015 | McPherson |
| 8,986,288 | B2 | 3/2015 | Konishi |
| 9,017,326 | B2 | 4/2015 | DiNardo et al. |
| D729,267 | S | 5/2015 | Yoo et al. |
| 9,055,870 | B2 | 6/2015 | Meador et al. |
| 9,065,394 | B2 | 6/2015 | Lim et al. |
| 9,129,054 | B2 | 9/2015 | Nawana et al. |
| 9,160,853 | B1 | 10/2015 | Daddi et al. |
| 9,168,054 | B2 | 10/2015 | Turner et al. |
| 9,168,091 | B2 | 10/2015 | Janssen et al. |
| 9,198,711 | B2 | 12/2015 | Joseph |
| 9,226,766 | B2 | 1/2016 | Aldridge et al. |
| 9,226,791 | B2 | 1/2016 | McCarthy et al. |
| 9,237,921 | B2 | 1/2016 | Messerly et al. |
| 9,265,429 | B2 | 2/2016 | St. Pierre et al. |
| 9,277,961 | B2 | 3/2016 | Panescu et al. |
| 9,277,969 | B2 | 3/2016 | Brannan et al. |
| 9,281,615 | B1 | 3/2016 | Plaza et al. |
| 9,320,646 | B2 | 4/2016 | Todd et al. |
| 9,345,481 | B2 | 5/2016 | Hall et al. |
| 9,345,900 | B2 | 5/2016 | Wu et al. |
| 9,351,653 | B1 | 5/2016 | Harrison |
| 9,370,361 | B2 | 6/2016 | Viola et al. |
| 9,391,670 | B2 | 7/2016 | Brukalo et al. |
| 9,427,255 | B2 | 8/2016 | Griffith et al. |
| 9,430,438 | B2 | 8/2016 | Biskup |
| 9,463,646 | B2 | 10/2016 | Payne et al. |
| 9,474,565 | B2 | 10/2016 | Shikhman et al. |
| D772,252 | S | 11/2016 | Myers et al. |
| 9,486,271 | B2 | 11/2016 | Dunning |
| 9,491,895 | B2 | 11/2016 | Steeves et al. |

(56) References Cited

U.S. PATENT DOCUMENTS

| | | | |
|---|---|---|---|
| 9,532,827 B2 | 1/2017 | Morgan et al. |
| 9,589,720 B2 | 3/2017 | Akahane |
| 9,600,031 B2 | 3/2017 | Kaneko et al. |
| 9,603,277 B2 | 3/2017 | Morgan et al. |
| D783,675 S | 4/2017 | Yagisawa et al. |
| D784,270 S | 4/2017 | Bhattacharya |
| 9,666,974 B2 | 5/2017 | Bopp |
| 9,713,503 B2 | 7/2017 | Goldschmidt |
| 9,715,271 B2 | 7/2017 | Kaestner |
| 9,750,563 B2 | 9/2017 | Shikhman et al. |
| 9,770,103 B2 | 9/2017 | Cochran et al. |
| 9,773,093 B2 | 9/2017 | Bernini et al. |
| 9,782,214 B2 | 10/2017 | Houser et al. |
| 9,788,907 B1 | 10/2017 | Alvi et al. |
| 9,804,977 B2 | 10/2017 | Ghosh et al. |
| D806,721 S | 1/2018 | Fischer |
| 9,867,670 B2 | 1/2018 | Brannan et al. |
| 9,892,483 B2 | 2/2018 | Lee et al. |
| 9,892,564 B1 | 2/2018 | Cvetko et al. |
| 9,907,196 B2 | 2/2018 | Susini et al. |
| 9,971,395 B2 | 5/2018 | Chenault et al. |
| 9,974,595 B2 | 5/2018 | Anderson et al. |
| 9,987,068 B2 | 6/2018 | Anderson et al. |
| 9,987,072 B2 | 6/2018 | McPherson |
| 10,028,402 B1 | 7/2018 | Walker |
| 10,039,589 B2 | 8/2018 | Virshek et al. |
| D832,211 S | 10/2018 | Ladd et al. |
| 10,098,527 B2 | 10/2018 | Weisenburgh, II et al. |
| 10,105,470 B2 | 10/2018 | Reasoner et al. |
| 10,109,835 B2 | 10/2018 | Yang |
| D834,541 S | 11/2018 | You et al. |
| 10,117,702 B2 | 11/2018 | Danziger et al. |
| 10,128,612 B1 | 11/2018 | Casto |
| 10,136,954 B2 | 11/2018 | Johnson et al. |
| 10,137,245 B2 | 11/2018 | Melker et al. |
| 10,147,148 B2 | 12/2018 | Wu et al. |
| 10,166,061 B2 | 1/2019 | Berry et al. |
| 10,170,205 B2 | 1/2019 | Curd et al. |
| 10,201,365 B2 | 2/2019 | Boudreaux et al. |
| 10,339,496 B2 | 7/2019 | Matson et al. |
| 10,357,184 B2 | 7/2019 | Crawford et al. |
| 10,386,990 B2 | 8/2019 | Shikhman et al. |
| 10,441,345 B2 | 10/2019 | Aldridge et al. |
| 10,449,004 B2 | 10/2019 | Ferro et al. |
| 10,475,244 B2 | 11/2019 | Cvetko et al. |
| 10,493,287 B2 | 12/2019 | Yoder et al. |
| 10,499,847 B2 | 12/2019 | Latimer et al. |
| 10,499,996 B2 | 12/2019 | de Almeida Barreto |
| 10,523,122 B2 | 12/2019 | Han et al. |
| 10,531,579 B2 | 1/2020 | Hsiao et al. |
| D876,466 S | 2/2020 | Kobayashi et al. |
| 10,561,753 B2 | 2/2020 | Thompson et al. |
| 10,602,007 B2 | 3/2020 | Takano |
| 10,624,667 B2 | 4/2020 | Faller et al. |
| 10,624,691 B2 | 4/2020 | Wiener et al. |
| 10,675,027 B2 | 6/2020 | Aldridge et al. |
| 10,675,100 B2 | 6/2020 | Frushour |
| 10,687,884 B2 | 6/2020 | Wiener et al. |
| 10,729,502 B1 | 8/2020 | Wolf et al. |
| 10,743,872 B2 | 8/2020 | Leimbach et al. |
| 10,758,309 B1 | 9/2020 | Chow et al. |
| 10,758,310 B2 | 9/2020 | Shelton, IV et al. |
| 10,772,673 B2 | 9/2020 | Allen, IV et al. |
| 10,878,966 B2 | 12/2020 | Wolf et al. |
| 10,881,399 B2 | 1/2021 | Shelton, IV et al. |
| 10,898,256 B2 | 1/2021 | Yates et al. |
| 10,898,279 B2 | 1/2021 | Yang |
| 10,925,598 B2 | 2/2021 | Scheib et al. |
| 10,932,705 B2 | 3/2021 | Muhsin et al. |
| 10,932,772 B2 | 3/2021 | Shelton, IV et al. |
| 10,950,982 B2 | 3/2021 | Regnier et al. |
| 10,987,176 B2 | 4/2021 | Poltaretskyi et al. |
| 10,989,724 B1 | 4/2021 | Holmes et al. |
| 11,000,270 B2 | 5/2021 | Scheib et al. |
| D924,139 S | 7/2021 | Jayme |
| 11,056,244 B2 | 7/2021 | Shelton, IV et al. |
| 11,065,079 B2 | 7/2021 | Wolf et al. |
| 11,071,595 B2 | 7/2021 | Johnson et al. |
| D928,725 S | 8/2021 | Oberkircher et al. |
| D928,726 S | 8/2021 | Asher et al. |
| 11,077,312 B2 | 8/2021 | Sturman et al. |
| 11,083,489 B2 | 8/2021 | Fujii et al. |
| 11,100,255 B1 | 8/2021 | Eftimie et al. |
| 11,116,587 B2 | 9/2021 | Wolf et al. |
| 11,185,379 B2 | 11/2021 | Shuma et al. |
| D939,545 S | 12/2021 | Oberkircher et al. |
| 11,259,793 B2 | 3/2022 | Scheib et al. |
| 11,259,875 B2 | 3/2022 | Boutin et al. |
| 11,272,839 B2 | 3/2022 | Al-Ali et al. |
| 11,284,963 B2 | 3/2022 | Shelton, IV et al. |
| 11,296,540 B2 | 4/2022 | Kirleis et al. |
| 11,304,763 B2 | 4/2022 | Shelton, IV et al. |
| 11,314,846 B1 | 4/2022 | Colin et al. |
| 11,369,366 B2 | 6/2022 | Scheib et al. |
| 11,382,699 B2 | 7/2022 | Wassall et al. |
| 11,382,700 B2 | 7/2022 | Calloway et al. |
| 11,419,604 B2 | 8/2022 | Scheib et al. |
| 11,424,027 B2 | 8/2022 | Shelton, IV |
| 11,432,877 B2 | 9/2022 | Nash et al. |
| 11,464,581 B2 | 10/2022 | Calloway |
| 11,478,820 B2 | 10/2022 | Bales, Jr. et al. |
| 11,504,192 B2 | 11/2022 | Shelton, IV et al. |
| 11,510,750 B2 | 11/2022 | Dulin et al. |
| 11,559,307 B2 | 1/2023 | Shelton, IV et al. |
| 11,564,678 B2 | 1/2023 | Scheib et al. |
| 11,571,205 B2 | 2/2023 | Scheib et al. |
| 11,576,677 B2 | 2/2023 | Shelton, IV et al. |
| 11,589,888 B2 | 2/2023 | Shelton, IV et al. |
| 11,659,023 B2 | 5/2023 | Shelton, IV et al. |
| 11,712,309 B2 | 8/2023 | Barak et al. |
| 2001/0029315 A1 | 10/2001 | Sakurai et al. |
| 2001/0031975 A1 | 10/2001 | Whitman et al. |
| 2002/0022836 A1 | 2/2002 | Goble et al. |
| 2002/0052563 A1 | 5/2002 | Penn et al. |
| 2002/0148942 A1 | 10/2002 | Payne et al. |
| 2002/0151770 A1 | 10/2002 | Noll et al. |
| 2002/0183734 A1 | 12/2002 | Bommannan et al. |
| 2003/0007321 A1 | 1/2003 | Dayley |
| 2003/0040670 A1 | 2/2003 | Govari |
| 2003/0050654 A1 | 3/2003 | Whitman et al. |
| 2003/0078631 A1 | 4/2003 | Nelson et al. |
| 2003/0093103 A1 | 5/2003 | Malackowski et al. |
| 2003/0114851 A1 | 6/2003 | Truckai et al. |
| 2003/0130677 A1 | 7/2003 | Whitman et al. |
| 2003/0199794 A1 | 10/2003 | Sakurai et al. |
| 2003/0199864 A1 | 10/2003 | Eick |
| 2004/0030328 A1 | 2/2004 | Eggers et al. |
| 2004/0059323 A1 | 3/2004 | Sturm et al. |
| 2004/0094597 A1 | 5/2004 | Whitman et al. |
| 2004/0111045 A1 | 6/2004 | Sullivan et al. |
| 2004/0111081 A1 | 6/2004 | Whitman et al. |
| 2004/0153724 A1 | 8/2004 | Nicholson et al. |
| 2004/0164983 A1 | 8/2004 | Khozai |
| 2005/0010209 A1 | 1/2005 | Lee et al. |
| 2005/0013459 A1 | 1/2005 | Maekawa |
| 2005/0021026 A1 | 1/2005 | Baily |
| 2005/0021890 A1 | 1/2005 | Baker et al. |
| 2005/0070800 A1 | 3/2005 | Takahashi |
| 2005/0113815 A1 | 5/2005 | Ritchie et al. |
| 2005/0113823 A1 | 5/2005 | Reschke et al. |
| 2005/0127868 A1 | 6/2005 | Calhoon et al. |
| 2005/0127869 A1 | 6/2005 | Calhoon et al. |
| 2005/0131390 A1 | 6/2005 | Heinrich et al. |
| 2005/0159778 A1 | 7/2005 | Heinrich et al. |
| 2005/0165390 A1 | 7/2005 | Mauti et al. |
| 2005/0173490 A1 | 8/2005 | Shelton, IV |
| 2005/0229110 A1 | 10/2005 | Gegner et al. |
| 2005/0251233 A1 | 11/2005 | Kanzius |
| 2006/0020213 A1 | 1/2006 | Whitman et al. |
| 2006/0085049 A1 | 4/2006 | Cory et al. |
| 2006/0136622 A1 | 6/2006 | Rouvelin et al. |
| 2006/0149418 A1 | 7/2006 | Anvari |
| 2006/0212069 A1 | 9/2006 | Shelton, IV |
| 2006/0256516 A1 | 11/2006 | Cho |

(56) References Cited

U.S. PATENT DOCUMENTS

| | | |
|---|---|---|
| 2006/0278680 A1 | 12/2006 | Viola et al. |
| 2006/0278681 A1 | 12/2006 | Viola et al. |
| 2006/0289600 A1 | 12/2006 | Wales et al. |
| 2007/0061393 A1 | 3/2007 | Moore |
| 2007/0076363 A1 | 4/2007 | Liang et al. |
| 2007/0085602 A1 | 4/2007 | Park et al. |
| 2007/0136218 A1 | 6/2007 | Bauer et al. |
| 2007/0282321 A1 | 12/2007 | Shah et al. |
| 2008/0072896 A1 | 3/2008 | Setzer et al. |
| 2008/0090652 A1 | 4/2008 | Kuehling et al. |
| 2008/0129465 A1 | 6/2008 | Rao |
| 2008/0249377 A1 | 10/2008 | Molducci et al. |
| 2008/0316304 A1 | 12/2008 | Claus et al. |
| 2009/0036884 A1 | 2/2009 | Gregg et al. |
| 2009/0054908 A1 | 2/2009 | Zand et al. |
| 2009/0101692 A1 | 4/2009 | Whitman et al. |
| 2009/0131929 A1 | 5/2009 | Shimizu |
| 2009/0216091 A1 | 8/2009 | Arndt |
| 2009/0228024 A1 | 9/2009 | Whitfield et al. |
| 2009/0234352 A1 | 9/2009 | Behnke et al. |
| 2009/0273353 A1 | 11/2009 | Kroh et al. |
| 2010/0036405 A1 | 2/2010 | Giordano et al. |
| 2010/0069939 A1 | 3/2010 | Konishi |
| 2010/0076453 A1 | 3/2010 | Morris et al. |
| 2010/0092006 A1 | 4/2010 | Rosen |
| 2010/0120266 A1 | 5/2010 | Rimborg |
| 2010/0198200 A1 | 8/2010 | Horvath |
| 2010/0312239 A1 | 12/2010 | Sclig |
| 2011/0015660 A1 | 1/2011 | Wiener et al. |
| 2011/0092972 A1 | 4/2011 | Allen |
| 2011/0093796 A1 | 4/2011 | Plummer et al. |
| 2011/0106567 A1 | 5/2011 | Asher |
| 2011/0125149 A1 | 5/2011 | El-Galley et al. |
| 2011/0130689 A1 | 6/2011 | Cohen et al. |
| 2011/0193580 A1 | 8/2011 | League |
| 2011/0238063 A1 | 9/2011 | Gregg |
| 2011/0245630 A1 | 10/2011 | St. Pierre et al. |
| 2011/0273465 A1 | 11/2011 | Konishi et al. |
| 2011/0288451 A1 | 11/2011 | Sanai et al. |
| 2011/0306840 A1 | 12/2011 | Allen et al. |
| 2012/0029304 A1 | 2/2012 | Medina et al. |
| 2012/0116380 A1 | 5/2012 | Madan et al. |
| 2012/0132661 A1 | 5/2012 | Gu et al. |
| 2012/0319890 A1 | 12/2012 | McCormack et al. |
| 2013/0031201 A1 | 1/2013 | Kagan et al. |
| 2013/0176220 A1 | 7/2013 | Merschon et al. |
| 2013/0197503 A1 | 8/2013 | Orszulak |
| 2013/0267975 A1 | 10/2013 | Timm et al. |
| 2013/0268283 A1 | 10/2013 | Vann et al. |
| 2014/0009894 A1 | 1/2014 | Yu |
| 2014/0058714 A1 | 2/2014 | Boyer |
| 2014/0087573 A1 | 3/2014 | Kroeckel |
| 2014/0097903 A1 | 4/2014 | Aoki et al. |
| 2014/0108048 A1 | 4/2014 | Cohn |
| 2014/0155721 A1 | 6/2014 | Hauck et al. |
| 2014/0194683 A1 | 7/2014 | Nakaguchi |
| 2014/0226572 A1 | 8/2014 | Thota et al. |
| 2014/0262598 A1 | 9/2014 | Miki et al. |
| 2014/0263552 A1 | 9/2014 | Hall et al. |
| 2014/0289823 A1 | 9/2014 | Tobin |
| 2014/0378958 A1 | 12/2014 | Leussler |
| 2015/0190189 A1 | 7/2015 | Yates et al. |
| 2015/0272575 A1 | 10/2015 | Leimbach et al. |
| 2015/0289929 A1 | 10/2015 | Toth et al. |
| 2015/0300923 A1 | 10/2015 | Halbert |
| 2015/0334879 A1 | 11/2015 | Fricker |
| 2015/0373115 A1 | 12/2015 | Breakstone et al. |
| 2016/0000495 A1* | 1/2016 | Elliott ............... A61B 18/1445 606/34 |
| 2016/0045247 A1 | 2/2016 | Heim et al. |
| 2016/0045365 A1 | 2/2016 | Foster et al. |
| 2016/0058286 A1 | 3/2016 | Joshua et al. |
| 2016/0062954 A1 | 3/2016 | Ruff et al. |
| 2016/0074096 A1 | 3/2016 | Lieu |
| 2016/0120591 A1 | 5/2016 | Smith et al. |
| 2016/0164466 A1 | 6/2016 | Briffa et al. |
| 2016/0199240 A1 | 7/2016 | Newkirk et al. |
| 2016/0225192 A1 | 8/2016 | Jones et al. |
| 2016/0249945 A1 | 9/2016 | Shelton, IV et al. |
| 2016/0287312 A1 | 10/2016 | Tegg et al. |
| 2016/0287337 A1 | 10/2016 | Aram et al. |
| 2017/0000553 A1 | 1/2017 | Wiener et al. |
| 2017/0007146 A1 | 1/2017 | Schulhauser et al. |
| 2017/0024978 A1 | 1/2017 | Gulrez et al. |
| 2017/0078455 A1 | 3/2017 | Fisher et al. |
| 2017/0080346 A1 | 3/2017 | Abbas |
| 2017/0090507 A1* | 3/2017 | Wiener ............. A61B 18/1206 |
| 2017/0151011 A1 | 6/2017 | Brustad et al. |
| 2017/0189096 A1 | 7/2017 | Danziger et al. |
| 2017/0202595 A1 | 7/2017 | Shelton, IV |
| 2017/0209718 A1 | 7/2017 | Tanis et al. |
| 2017/0251305 A1 | 8/2017 | Fathollahi |
| 2017/0252091 A1 | 9/2017 | Honda |
| 2017/0296213 A1 | 10/2017 | Swensgard et al. |
| 2017/0319259 A1 | 11/2017 | Dunning |
| 2017/0360466 A1 | 12/2017 | Brown et al. |
| 2018/0014872 A1 | 1/2018 | Dickerson |
| 2018/0026469 A1 | 1/2018 | Kamath et al. |
| 2018/0042659 A1 | 2/2018 | Rupp et al. |
| 2018/0049795 A1 | 2/2018 | Swayze et al. |
| 2018/0065248 A1 | 3/2018 | Barral et al. |
| 2018/0078216 A1 | 3/2018 | Baker et al. |
| 2018/0082480 A1 | 3/2018 | White et al. |
| 2018/0099161 A1 | 4/2018 | Honda |
| 2018/0166809 A1 | 6/2018 | Brogan et al. |
| 2018/0206909 A1 | 7/2018 | Brustad et al. |
| 2018/0221005 A1 | 8/2018 | Hamel et al. |
| 2018/0228528 A1 | 8/2018 | Fraasch et al. |
| 2018/0239856 A1 | 8/2018 | Takeuchi et al. |
| 2018/0262595 A1 | 9/2018 | Perchlik |
| 2018/0262916 A1 | 9/2018 | Polley et al. |
| 2018/0263557 A1 | 9/2018 | Kahlman |
| 2018/0296283 A1 | 10/2018 | Crawford et al. |
| 2018/0333207 A1 | 11/2018 | Moctezuma De La Barrera |
| 2018/0367870 A1 | 12/2018 | Shih |
| 2019/0000478 A1 | 1/2019 | Messerly et al. |
| 2019/0069957 A1 | 3/2019 | Barral et al. |
| 2019/0124701 A1 | 4/2019 | Mcclellan |
| 2019/0125455 A1 | 5/2019 | Shelton, IV et al. |
| 2019/0200844 A1 | 7/2019 | Shelton, IV et al. |
| 2019/0200906 A1 | 7/2019 | Shelton, IV et al. |
| 2019/0200981 A1 | 7/2019 | Harris et al. |
| 2019/0201102 A1 | 7/2019 | Shelton, IV et al. |
| 2019/0201140 A1 | 7/2019 | Yates et al. |
| 2019/0201158 A1 | 7/2019 | Shelton, IV et al. |
| 2019/0206563 A1 | 7/2019 | Shelton, IV et al. |
| 2019/0224434 A1 | 7/2019 | Silver et al. |
| 2019/0236840 A1 | 8/2019 | Zuckerman et al. |
| 2019/0247141 A1 | 8/2019 | Batchelor et al. |
| 2019/0247664 A1 | 8/2019 | Irazoqui et al. |
| 2019/0269457 A1* | 9/2019 | Schofield ........... A61B 18/1233 |
| 2019/0278262 A1 | 9/2019 | Taylor et al. |
| 2019/0279524 A1 | 9/2019 | Stoyanov et al. |
| 2019/0348169 A1 | 11/2019 | Gibby et al. |
| 2019/0371012 A1 | 12/2019 | Flexman et al. |
| 2020/0004487 A1 | 1/2020 | Hanajima et al. |
| 2020/0015899 A1 | 1/2020 | Scheib et al. |
| 2020/0015900 A1 | 1/2020 | Scheib et al. |
| 2020/0015907 A1 | 1/2020 | Scheib |
| 2020/0015924 A1 | 1/2020 | Scheib et al. |
| 2020/0030044 A1 | 1/2020 | Wang et al. |
| 2020/0038120 A1 | 2/2020 | Ziraknejad et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078077 A1 | 3/2020 | Henderson et al. |
| 2020/0078078 A1 | 3/2020 | Henderson et al. |
| 2020/0078079 A1 | 3/2020 | Morgan et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078083 A1 | 3/2020 | Sprinkle et al. |
| 2020/0078089 A1 | 3/2020 | Henderson et al. |
| 2020/0078106 A1 | 3/2020 | Henderson et al. |

(56) References Cited

U.S. PATENT DOCUMENTS

| | | | |
|---|---|---|---|
| 2020/0078110 A1 | 3/2020 | Henderson et al. | |
| 2020/0078111 A1 | 3/2020 | Oberkircher et al. | |
| 2020/0078112 A1 | 3/2020 | Henderson et al. | |
| 2020/0078113 A1 | 3/2020 | Sawhney et al. | |
| 2020/0078114 A1 | 3/2020 | Asher et al. | |
| 2020/0078115 A1 | 3/2020 | Asher et al. | |
| 2020/0078116 A1 | 3/2020 | Oberkircher et al. | |
| 2020/0078117 A1 | 3/2020 | Henderson et al. | |
| 2020/0078118 A1 | 3/2020 | Henderson et al. | |
| 2020/0078119 A1 | 3/2020 | Henderson et al. | |
| 2020/0078120 A1 | 3/2020 | Aldridge et al. | |
| 2020/0081585 A1 | 3/2020 | Petre et al. | |
| 2020/0090808 A1* | 3/2020 | Carroll | H04L 67/12 |
| 2020/0100825 A1 | 4/2020 | Henderson et al. | |
| 2020/0100830 A1 | 4/2020 | Henderson et al. | |
| 2020/0106220 A1* | 4/2020 | Henderson | H04L 12/40006 |
| 2020/0129223 A1 | 4/2020 | Angeles et al. | |
| 2020/0159313 A1 | 5/2020 | Gibby et al. | |
| 2020/0237422 A1 | 7/2020 | Canady | |
| 2020/0265398 A1 | 8/2020 | Lembo | |
| 2020/0268472 A1 | 8/2020 | Wolf et al. | |
| 2020/0305924 A1 | 10/2020 | Carroll | |
| 2020/0305945 A1 | 10/2020 | Morgan et al. | |
| 2020/0314569 A1 | 10/2020 | Morgan et al. | |
| 2020/0342228 A1 | 10/2020 | Prevrhal et al. | |
| 2020/0405375 A1 | 12/2020 | Shelton, IV et al. | |
| 2021/0121246 A1 | 4/2021 | Gudalo | |
| 2021/0169578 A1 | 6/2021 | Calloway et al. | |
| 2021/0196383 A1 | 7/2021 | Shelton, IV et al. | |
| 2021/0203889 A1 | 7/2021 | Fung et al. | |
| 2021/0212717 A1 | 7/2021 | Yates et al. | |
| 2021/0236755 A1 | 8/2021 | King et al. | |
| 2021/0264680 A1 | 8/2021 | Cvetko, et al. | |
| 2021/0313938 A1 | 10/2021 | Tanaka et al. | |
| 2021/0338343 A1 | 11/2021 | Swaffield et al. | |
| 2021/0385889 A1 | 12/2021 | Patel | |
| 2022/0032442 A1 | 2/2022 | Sheffield et al. | |
| 2022/0104867 A1 | 4/2022 | Shelton, IV et al. | |
| 2022/0104896 A1 | 4/2022 | Shelton, IV et al. | |
| 2022/0104897 A1 | 4/2022 | Shelton, IV et al. | |
| 2022/0104911 A1 | 4/2022 | Shelton, IV et al. | |
| 2022/0151704 A1 | 5/2022 | Nikou | |
| 2022/0155910 A1 | 5/2022 | Jeong | |
| 2022/0261056 A1 | 8/2022 | Motoi et al. | |
| 2022/0313338 A1 | 10/2022 | Carroll et al. | |
| 2022/0313341 A1 | 10/2022 | Wiener et al. | |
| 2022/0313342 A1 | 10/2022 | Leuck et al. | |
| 2022/0313357 A1 | 10/2022 | Geresy et al. | |
| 2022/0313369 A1 | 10/2022 | Oberkircher et al. | |
| 2022/0313370 A1 | 10/2022 | Morgan et al. | |
| 2022/0313371 A1 | 10/2022 | Morgan et al. | |
| 2022/0313372 A1 | 10/2022 | Herman et al. | |
| 2022/0313373 A1 | 10/2022 | Morgan et al. | |
| 2022/0317750 A1 | 10/2022 | Jayme et al. | |
| 2022/0317751 A1 | 10/2022 | Samuel et al. | |
| 2022/0319685 A1 | 10/2022 | Vachon et al. | |
| 2022/0319693 A1 | 10/2022 | Oberkircher et al. | |
| 2022/0321059 A1 | 10/2022 | Samuel et al. | |
| 2022/0322523 A1 | 10/2022 | Jayme et al. | |
| 2022/0331013 A1 | 10/2022 | Shelton, IV et al. | |
| 2022/0331047 A1 | 10/2022 | Shelton, IV et al. | |
| 2022/0331048 A1 | 10/2022 | Shelton, IV et al. | |
| 2022/0331049 A1 | 10/2022 | Shelton, IV et al. | |
| 2022/0331050 A1 | 10/2022 | Shelton, IV et al. | |
| 2022/0331051 A1 | 10/2022 | Shelton, IV et al. | |
| 2022/0331052 A1 | 10/2022 | Shelton, IV et al. | |
| 2022/0331053 A1 | 10/2022 | Kimball et al. | |
| 2022/0331054 A1 | 10/2022 | Kimball et al. | |
| 2022/0331056 A1 | 10/2022 | Shelton, IV et al. | |
| 2022/0334787 A1 | 10/2022 | Jogan et al. | |
| 2022/0335604 A1 | 10/2022 | Vanosdoll et al. | |
| 2022/0335660 A1 | 10/2022 | Shelton, IV et al. | |
| 2022/0335696 A1 | 10/2022 | Shelton, IV et al. | |
| 2022/0336078 A1 | 10/2022 | Wise et al. | |
| 2022/0336097 A1 | 10/2022 | Shelton, IV et al. | |
| 2022/0337891 A1 | 10/2022 | Burnley et al. | |
| 2022/0338049 A1 | 10/2022 | Ross et al. | |
| 2023/0038130 A1 | 2/2023 | Cvetko et al. | |
| 2023/0039037 A1 | 2/2023 | Henderson et al. | |
| 2023/0069787 A1 | 3/2023 | Henderson et al. | |
| 2023/0072423 A1 | 3/2023 | Osborn et al. | |
| 2023/0346446 A1 | 11/2023 | Henderson et al. | |

FOREIGN PATENT DOCUMENTS

| | | | |
|---|---|---|---|
| EP | 0929263 B1 | 7/1999 | |
| EP | 1006892 B1 | 6/2009 | |
| EP | 2942023 A2 | 11/2015 | |
| JP | S635457 A | 1/1988 | |
| JP | H8280706 A | 10/1996 | |
| JP | H1069453 A | 3/1998 | |
| JP | 2000089850 A | 3/2000 | |
| JP | 2001029353 A | 2/2001 | |
| JP | 2001128993 A | 5/2001 | |
| JP | 2002336194 A | 11/2002 | |
| JP | 2006303167 A | 11/2006 | |
| JP | 2007174666 A | 7/2007 | |
| JP | 2009291308 A | 12/2009 | |
| JP | 2010063883 A | 3/2010 | |
| JP | 2011182849 A | 9/2011 | |
| JP | 2012210294 A | 11/2012 | |
| JP | 2014210052 A | 11/2014 | |
| JP | 2017003905 A | 1/2017 | |
| KR | 20110081018 A | 7/2011 | |
| WO | WO-0112089 A1 | 2/2001 | |
| WO | WO-2008053485 A1 | 5/2008 | |
| WO | 2010073732 A1 | 7/2010 | |
| WO | WO-2014031800 A1 | 2/2014 | |
| WO | WO-2014071184 A1 | 5/2014 | |
| WO | WO-2015047693 A1 | 4/2015 | |
| WO | WO-2017058617 | 4/2017 | |
| WO | WO-2018116247 A1 | 6/2018 | |
| WO | WO-2019215354 A1 | 11/2019 | |
| WO | 2021055590 A1 | 3/2021 | |
| WO | WO-2021044136 A1 | 3/2021 | |

OTHER PUBLICATIONS

IEEE Std 802.Mar. 2012 (Revision of IEEE Std 802.3.2008, published Dec. 28, 2012.

"ATM-MPLS Network Interworking Version 2.0, af-aic-0178.001" ATM Standard, The ATM Forum Technical Committe, published Aug. 2003.

"Bowa ARC 400" Oct. 30, 2018, posted at bowa-medical.com, [site visited Aug. 6, 2021], https://www.bowa-medical.com/tradepro/shopru/artikel/allgemein/BOWA_BRO_11181_ARC400_V2.1_2018_10_30_EN.pdf (Year: 2018).

"Electrosurgical Generator ECONT-0201.3" Mar. 18, 2018, posted at contact-endoscopy.com, [site visited Aug. 6, 2021], https://contact-endoscopy.com/electrosurgical-system (Year: 2018).

Li et al., "Wearable Energy Harvesters Generating Electricity From Low-Frequency Human Limb Movement," Microsystems & Nanoengineering (2018), vol. 4(24), 13 pages.

Qian, et al., "A Review of Augmented Reality in Robotic-Assisted Surgery", IEEE Transactions on Medical Robotics and Bionics, IEEE, vol. 2, No. 1, pp. 1-16, Feb. 2020.

Yu et al., "Skin-Integrated Wireless Haptic Interfaces for Virtual and Augmented Reality," Nature, vol. 575, pp. 473-479, Nov. 21, 2019.

Zhu et al. "Haptic-feedback smart glove as a creative human-machine interface (HMI) for virtual/augmented reality applications," Sci. Adv, vol. 6, No. 19, May 8, 2020.

"Road Vehicles—Functional Safety—Part 1: Vocabulary", International Organization for Standardization, Edition 2, 2018, 41 pages.

International Search Report and Written Opinion received for PCT Application No. PCT/IB2022/052805 mailed on Sep. 14, 2022, 18 pages.

International Search Report and Written Opinion received for PCT Application No. PCT/IB2022/052831 mailed on Sep. 29, 2022, 28 pages.

(56)                References Cited

OTHER PUBLICATIONS

Invitation to Pay Additional Fees received for PCT Application No. PCT/IB2022/052805 mailed on Jun. 28, 2022, 10 pages.
Invitation to Pay Additional Fees received for PCT Application No. PCT/IB2022/052831 mailed on Jun. 21, 2022, 12 pages.

* cited by examiner

INTELLIGENT DATA PORTS FOR MODULAR ENERGY SYSTEMS

BACKGROUND

The present disclosure relates to various surgical systems, including modular electrosurgical and/or ultrasonic surgical systems. Operating rooms (ORs) are in need of streamlined capital solutions because ORs are a tangled web of cords, devices, and people due to the number of different devices that are needed to complete each surgical procedure. This is a reality of every OR in every market throughout the globe. Capital equipment is a major offender in creating clutter within ORs because most capital equipment performs one task or job, and each type of capital equipment requires unique techniques or methods to use and has a unique user interface. Accordingly, there are unmet consumer needs for capital equipment and other surgical technology to be consolidated in order to decrease the equipment footprint within the OR, streamline the equipment's interfaces, and improve surgical staff efficiency during a surgical procedure by reducing the number of devices that surgical staff members need to interact with.

A long-life-cycle modular energy system requires support for future accessories and technologies. To support such future accessories, the modular energy system requires an interface configured to support a wide variety of such future accessories. Such interfaces require a flexible and extensible port for coupling accessories to the modular energy system to provide a variety of functionality that facilitate support for a wide range of use cases and potential future accessories. Providing serial functionality for use by the accessories presents potential challenges related to cybersecurity, system reliability, and system power budgeting. Controlling such accessories remotely may include commanding the remote system to power up or power down while the remote system may be in a limited functionality operational state (such as "powered down"). The present disclosure provides one or more circuits and methods to resolve such future accessory functionality for modular energy systems.

SUMMARY

In one aspect, the present disclosure provides an accessory circuit for a modular energy system. The accessory circuit comprises an accessory port configured to receive an accessory; a power supply; a processor; an isolation barrier configured to electrically isolate the processor and the power supply from the accessory port; a flexible serial communication interface coupled between the processor and the accessory port, the flexible serial communication interface configured to support multiple communication protocols; and a presence detection circuit coupled between the accessory port and the processor. The presence detection circuit is configured to detect presence of an accessory connected to the accessory port.

In another aspect, the present disclosure provides a flexible serial bus power configuration circuit for a modular energy system. The flexible serial bus power configuration circuit comprises a processor system; a serial bus hub coupled to the processor system; at least two serial bus power controllers, wherein each of the at least two serial bus controllers is independently coupled to the processor system; and a serial bus port configurable in a first or second mode, the serial bus port configured to independently receive a serial bus device, wherein the serial bus hub is coupled to the serial bus port, and wherein one of the at least two serial bus power controllers is coupled to the serial bus port configured in a first mode, and wherein another of the at least two serial bus power controllers is coupled to the serial bus port configured in a second mode. The processor system is configured to individually control each of the at least two serial bus power controllers to control power applied to the serial bus port.

In yet another aspect, the present disclosure provides a remote power control interface for a modular energy system. The remote power control interface comprises a master system comprising at least one driver/buffer circuit and one input circuit; and a slave system located remotely from the master system, the slave system comprising at least one driver/buffer circuit and at least one input circuit. The master is configured to enable and disable the slave system.

FIGURES

The various aspects described herein, both as to organization and methods of operation, together with further objects and advantages thereof, may best be understood by reference to the following description, taken in conjunction with the accompanying drawings as follows.

Corresponding reference characters indicate corresponding parts throughout the several views. The exemplifications set out herein illustrate various disclosed aspects, in one form, and such exemplifications are not to be construed as limiting the scope thereof in any manner.

DESCRIPTION

Figure 1:
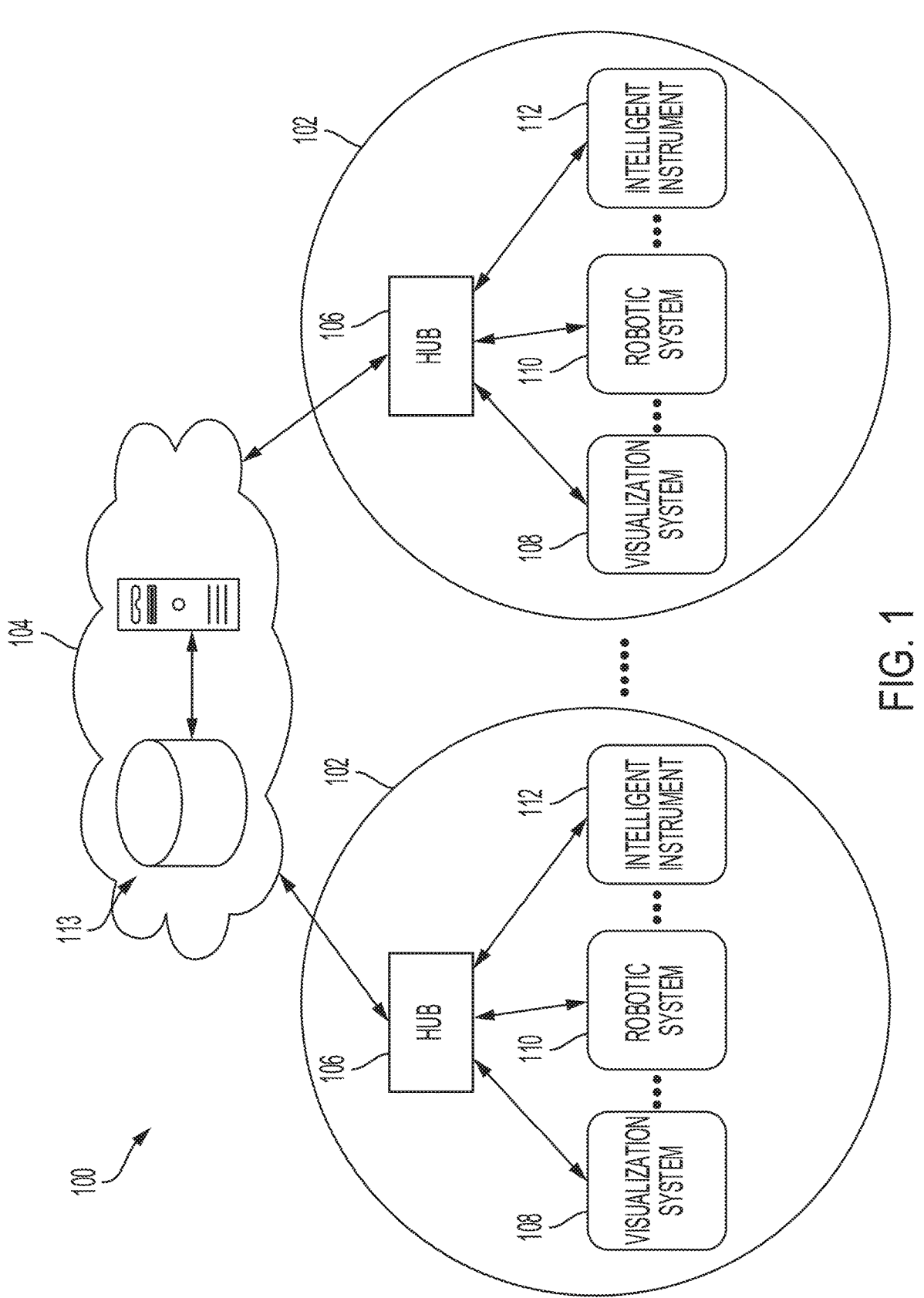
FIG. 1 is a block diagram of a computer-implemented interactive surgical system, in accordance with at least one aspect of the present disclosure.

Applicant of the present application owns the following U.S. Patent Applications filed Mar. 30, 2021, the disclosure of each of which is herein incorporated by reference in its entirety:

U.S. patent application Ser. No. 17/217,394, titled METHOD FOR MECHANICAL PACKAGING FOR MODULAR ENERGY SYSTEM, now U.S. Patent Application Publication No. 2022/0322523;

U.S. patent application Ser. No. 17/217,402, titled BACKPLANE CONNECTOR ATTACHMENT MECHANISM FOR MODULAR ENERGY SYSTEM, now U.S. Patent Application Publication No. 2022/0317750;

U.S. Patent Application Ser. No. 17/217,436, titled BEZEL WITH LIGHT BLOCKING FEATURES FOR MODULAR ENERGY SYSTEM, now U.S. Pat. No. 11,857,252;

U.S. patent application Ser. No. 17/217,446, titled HEADER FOR MODULAR ENERGY SYSTEM, now U.S. Patent Application Publication No. 2022/0313342;

U.S. patent application Ser. No. 17/217,403, titled SURGICAL PROCEDURALIZATION VIA MODULAR ENERGY SYSTEM, now U.S. Patent Application Publication No. 2022/0313341;

U.S. patent application Ser. No. 17/217,424, titled METHOD FOR ENERGY DELIVERY FOR MODULAR ENERGY SYSTEM, now U.S. Patent Application Publication No. 2022/0317751;

U.S. Patent Application Ser. No. 17/217,439, titled MODULAR ENERGY SYSTEM WITH DUAL AMPLIFIERS AND TECHNIQUES FOR UPDATING PARAMETERS THEREOF, now U.S. Patent Application Publication No. 2022/0321059;

U.S. patent application Ser. No. 17/217,471, titled MODULAR ENERGY SYSTEM WITH MULTI-EN-

5

ERGY PORT SPLITTER FOR MULTIPLE ENERGY DEVICES, now U.S. Patent Application Publication No. 2022/0313373;

U.S. patent application Ser. No. 17/217,385, titled METHOD FOR INTELLIGENT INSTRUMENTS FOR MODULAR ENERGY SYSTEM, now U.S. Patent Application Publication No. 2022/0313369;

U.S. patent application Ser. No. 17/217,392, titled RADIO FREQUENCY IDENTIFICATION TOKEN FOR WIRELESS SURGICAL INSTRUMENTS, now U.S. Patent Application Publication No. 2022/0319693;

U.S. patent application Ser. No. 17/217,405, titled METHOD FOR SYSTEM ARCHITECTURE FOR MODULAR ENERGY SYSTEM, now U.S. Patent Application Publication No. 2022/0313370;

U.S. patent application Ser. No. 17/217,423, titled USER INTERFACE MITIGATION TECHNIQUES FOR MODULAR ENERGY SYSTEMS, now U.S. Patent Application Publication No. 2022/0313371;

U.S. patent application Ser. No. 17/217,429, titled ENERGY DELIVERY MITIGATIONS FOR MODULAR ENERGY SYSTEMS, now U.S. Patent Application Publication No. 2022/0313338;

U.S. patent application Ser. No. 17/217,449, titled ARCHITECTURE FOR MODULAR ENERGY SYSTEM, now U.S. Patent Application Publication No. 2022/0313372; and U.S. patent application Ser. No. 17/217,461, titled MODULAR ENERGY SYSTEM WITH HARDWARE MITIGATED COMMUNICATION, now U.S. Patent Application Publication No. 2022/0319685.

Applicant of the present application owns the following U.S. Patent Applications filed Mar. 30, 2021, the disclosure of each of which is herein incorporated by reference in its entirety:

U.S. patent application Ser. No. 16,562,144, title METHOD FOR CONTROLLING A MODULAR ENERGY SYSTEM USER INTERFACE, now U.S. Patent Application Publication No. 2020/0078106;

U.S. patent application Ser. No. 16/562,151, titled PASSIVE HEADER MODULE FOR A MODULAR ENERGY SYSTEM, now U.S. Patent Application Publication No. 2020/0078110;

U.S. patent application Ser. No. 16/562,157, titled CONSOLIDATED USER INTERFACE FOR MODULAR ENERGY SYSTEM, now U.S. Patent Application Publication No. 2020/0081585;

U.S. patent application Ser. No. 16/562,159, titled AUDIO TONE CONSTRUCTION FOR AN ENERGY MODULE OF A MODULAR ENERGY SYSTEM, now U.S. Patent Application Publication No. 2020/0314569;

U.S. patent application Ser. No. 16/562,163, titled ADAPTABLY CONNECTABLE AND REASSIGNABLE SYSTEM ACCESSORIES FOR MODULAR ENERGY SYSTEM, now U.S. Patent Application Publication No. 2020/0078111;

U.S. patent application Ser. No. 16/562,123, titled METHOD FOR CONSTRUCTING AND USING A MODULAR SURGICAL ENERGY SYSTEM WITH MULTIPLE DEVICES, now U.S. Patent Application Publication No. 2020/0100830;

U.S. patent application Ser. No. 16/562,135, titled METHOD FOR CONTROLLING AN ENERGY MODULE OUTPUT, now U.S. Patent Application Publication No. 2020/0078076;

U.S. patent application Ser. No. 16/562,180, titled ENERGY MODULE FOR DRIVING MULTIPLE ENERGY MODALITIES, now U.S. Patent Application Publication No. 2020/0078080;

U.S. patent application Ser. No. 16/562,184, titled GROUNDING ARRANGEMENT OF ENERGY MODULES, now U.S. Patent Application Publication No. 2020/0078081;

U.S. patent application Ser. No. 16/562,188, titled BACKPLANE CONNECTOR DESIGN TO CONNECT STACKED ENERGY MODULES, now U.S. Patent Application Publication No. 2020/0078116;

U.S. patent application Ser. No. 16/562,195, titled ENERGY MODULE FOR DRIVING MULTIPLE ENERGY MODALITIES THROUGH A PORT, now U.S. Patent Application Publication No. 2020/0078117;

U.S. patent application Ser. No. 16/562,202, titled SURGICAL INSTRUMENT UTILIZING DRIVE SIGNAL TO POWER SECONDARY FUNCTION, now U.S. Patent Application Publication No. 2020/0078082;

U.S. patent application Ser. No. 16/562,142, titled METHOD FOR ENERGY DISTRIBUTION IN A SURGICAL MODULAR ENERGY SYSTEM, now U.S. Patent Application Publication No. 2020/0078070;

U.S. patent application Ser. No. 16/562,169, titled Surgical Modular energy system with A segmented backplane, now U.S. Patent Application Publication No. 2020/0078112;

U.S. patent application Ser. No. 16/562,185, titled Surgical Modular energy system with footer module, now U.S. Patent Application Publication No. 2020/0078115;

U.S. patent application Ser. No. 16/562,203, titled Power and Communication mitigation arrangement for modular surgical energy system, now U.S. Patent Application Publication No. 2020/0078118;

U.S. patent application Ser. No. 16/562,212, titled MODULAR SURGICAL ENERGY SYSTEM WITH MODULE POSITIONAL AWARENESS SENSING WITH VOLTAGE DETECTION, now U.S. Patent Application Publication No. 2020/0078119;

U.S. patent application Ser. No. 16/562,234, titled MODULAR SURGICAL ENERGY SYSTEM WITH MODULE POSITIONAL AWARENESS SENSING WITH TIME COUNTER, now U.S. Patent Application Publication No. 2020/0305945;

U.S. patent application Ser. No. 16/562,243, titled MODULAR SURGICAL ENERGY SYSTEM WITH MODULE POSITIONAL AWARENESS WITH DIGITAL LOGIC, now U.S. Patent Application Publication No. 2020/0078120;

U.S. patent application Ser. No. 16/562,125, titled METHOD FOR COMMUNICATING BETWEEN MODULES AND DEVICES IN A MODULAR SURGICAL SYSTEM, now U.S. Patent Application Publication No. 2020/0100825;

U.S. patent application Ser. No. 16/562,137, titled FLEXIBLE HAND-SWITCH CIRCUIT, now U.S. Patent Application Publication No. 2020/0106220;

U.S. patent application Ser. No. 16/562,143, titled FIRST AND SECOND COMMUNICATION PROTOCOL ARRANGEMENT FOR DRIVING PRIMARY AND SECONDARY DEVICES THROUGH A SINGLE PORT, now U.S. Patent Application Publication No. 2020/0090808;

U.S. patent application Ser. No. 16/562,148, titled FLEX-IBLE NEUTRAL ELECTRODE, now U.S. Patent Application Publication No. 2020/0078077;

U.S. patent application Ser. No. 16/562,154, titled SMART RETURN PAD SENSING THROUGH MODULATION OF NEAR FIELD COMMUNICA-TION AND CONTACT QUALITY MONITORING SIGNALS, now U.S. Patent Application Publication No. 2020/0078089;

U.S. patent application Ser. No. 16/562,162, titled AUTO-MATIC ULTRASONIC ENERGY ACTIVATION CIRCUIT DESIGN FOR MODULAR SURGICAL SYSTEMS, now U.S. Patent Application Publication No. 2020/0305924;

U.S. patent application Ser. No. 16/562,167, titled COORDINATED ENERGY OUTPUTS OF SEPA-RATE BUT CONNECTED MODULES, now U.S. Patent Application Publication No. 2020/0078078;

U.S. patent application Ser. No. 16/562,170, titled MAN-AGING SIMULTANEOUS MONOPOLAR OUT-PUTS USING DUTY CYCLE AND SYNCHRONI-ZATION, now U.S. Patent Application Publication No. 2020/0078079;

U.S. patent application Ser. No. 16/562,172, titled PORT PRESENCE DETECTION SYSTEM FOR MODU-LAR ENERGY SYSTEM, now U.S. Patent Applica-tion Publication No. 2020/0078113;

U.S. patent application Ser. No. 16/562,175, titled INSTRUMENT TRACKING ARRANGEMENT BASED ON REAL TIME CLOCK INFORMATION, now U.S. Patent Application Publication No. 2020/0078071;

U.S. patent application Ser. No. 16/562,177, titled REGIONAL LOCATION TRACKING OF COMPO-NENTS OF A MODULAR ENERGY SYSTEM, now U.S. Patent Application Publication No. 2020/0078114;

U.S. Design Patent Application Serial No. 29/704,610, titled ENERGY MODULE;

U.S. Design Patent Application Serial No. 29/704,614, titled ENERGY MODULE MONOPOLAR PORT WITH FOURTH SOCKET AMONG THREE OTHER SOCKETS;

U.S. Design Patent Application Serial No. 29/704,616, titled BACKPLANE CONNECTOR FOR ENERGY MODULE; and U.S. Design Patent Application Serial No. 29/704,617, titled ALERT SCREEN FOR ENERGY MODULE.

Applicant of the present application owns the following U.S. Patent Provisional Applications filed Mar. 29, 2019, the disclosure of each of which is herein incorporated by reference in its entirety:

U.S. Provisional Patent Application Ser. No. 62/826,584, titled MODULAR SURGICAL PLATFORM ELEC-TRICAL ARCHITECTURE;

U.S. Provisional Patent Application Ser. No. 62/826,587, titled MODULAR ENERGY SYSTEM CONNECTIV-ITY;

U.S. Provisional Patent Application Ser. No. 62/826,588, titled MODULAR ENERGY SYSTEM INSTRU-MENT COMMUNICATION TECHNIQUES; and U.S. Provisional Patent Application Ser. No. 62/826,592, titled MODULAR ENERGY DELIVERY SYSTEM.

Applicant of the present application owns the following U.S. Patent Provisional Application filed Sep. 7, 2018, the disclosure of each of which is herein incorporated by reference in its entirety:

U.S. Provisional Patent Application Ser. No. 62/728,480, titled MODULAR ENERGY SYSTEM AND USER INTERFACE.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expres-sions of aspects, and/or examples, can be combined with any one or more of the other following-described aspects, expressions of aspects and/or examples.

Various aspects are directed to improved ultrasonic sur-gical devices, electrosurgical devices and generators for use therewith. Aspects of the ultrasonic surgical devices can be configured for transecting and/or coagulating tissue during surgical procedures, for example. Aspects of the electrosur-gical devices can be configured for transecting, coagulating, scaling, welding and/or desiccating tissue during surgical procedures, for example.

Surgical System Hardware

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communi-cate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 2:
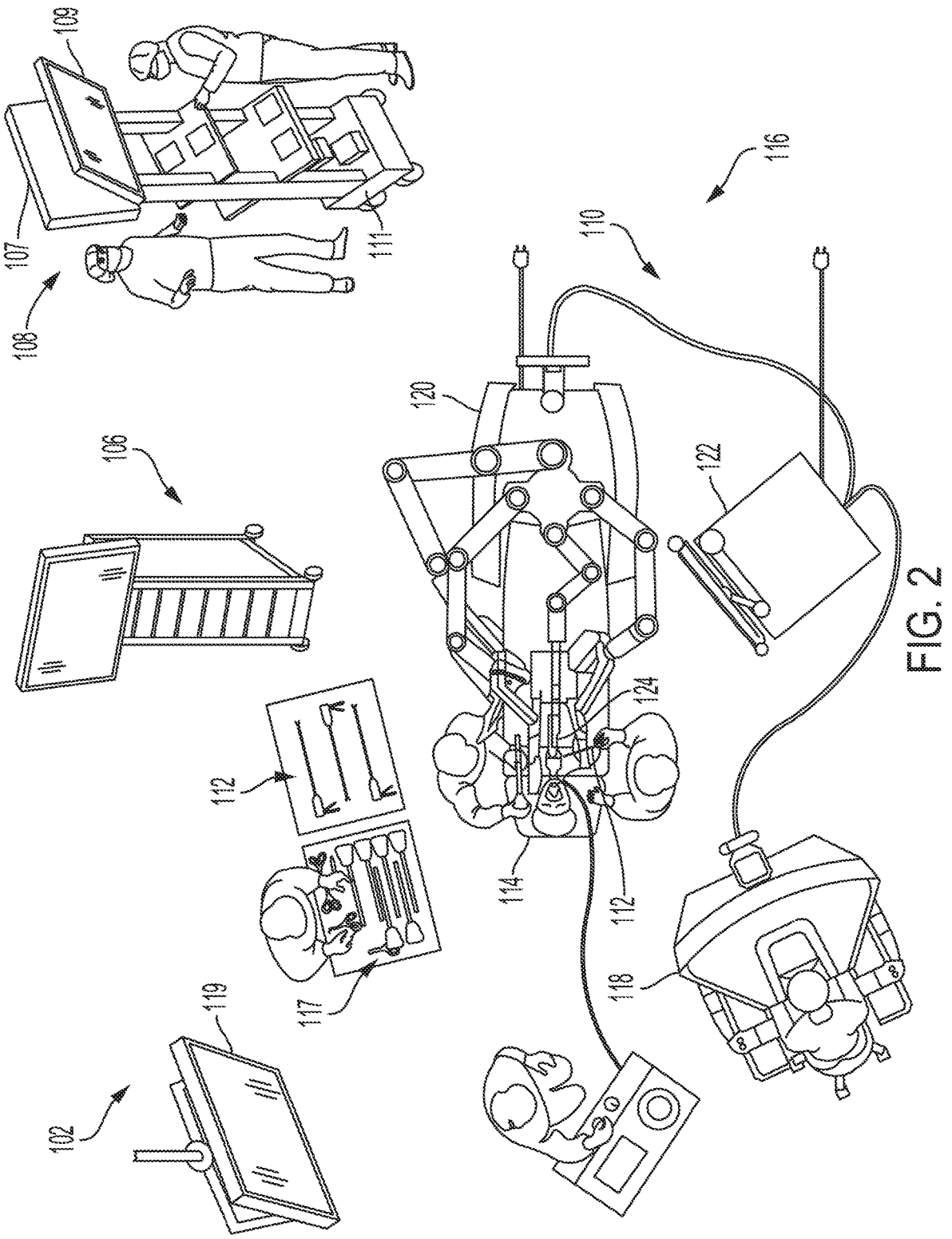
FIG. 2 is a surgical system being used to perform a surgical procedure in an operating room, in accordance with at least one aspect of the present disclosure.

FIG. 2 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading SURGICAL INSTRUMENT HARDWARE and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Figure 3:
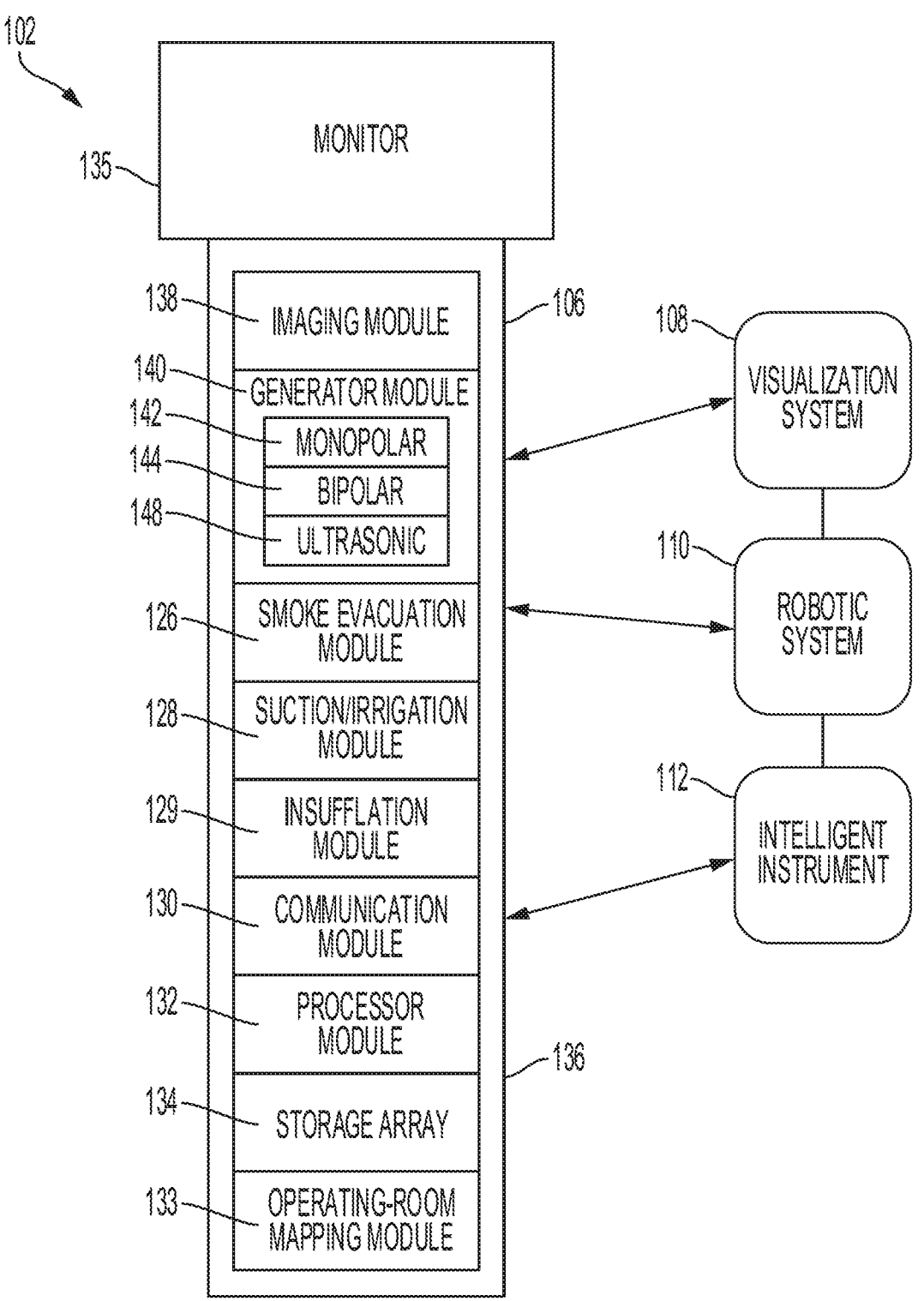
FIG. 3 is a surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. In some aspects, the visualization system 108 may be a separable piece of equipment. In alternative aspects, the visualization system 108 could be contained within the hub 106 as a functional module. The hub 106 includes a hub display 135, an imaging module 138, a generator module 140, a communication module 130, a processor module 132, a storage array 134, and an operating room mapping module 133. In certain aspects, as illustrated in FIG. 3, the hub 106 further includes a smoke evacuation module 126, a suction/irrigation module 128, and/or an insufflation module 129. In certain aspects, any of the modules in the hub 106 may be combined with each other into a single module.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes one or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts. In one aspect, the first energy-generator module is slidably movable into an electrical engagement with the power and data contacts and wherein the first energy-generator module is slidably movable out of the electrical engagement with the first power and data contacts. In an alternative aspect, the first energy-generator module is stackably movable into an electrical engagement with the power and data contacts and wherein the first energy-generator module is stackably movable out of the electrical engagement with the first power and data contacts.

Further to the above, the modular surgical enclosure also includes a second energy-generator module configured to generate a second energy, either the same or different than the first energy, for application to the tissue, and a second docking station comprising a second docking port that includes second data and power contacts. In one aspect, the second energy-generator module is slidably movable into an electrical engagement with the power and data contacts, and wherein the second energy-generator module is slidably movable out of the electrical engagement with the second power and data contacts. In an alternative aspect, the second energy-generator module is stackably movable into an electrical engagement with the power and data contacts, and wherein the second energy-generator module is stackably movable out of the electrical engagement with the second power and data contacts.

In addition, the modular surgical enclosure also includes a communication bus between the first docking port and the second docking port, configured to facilitate communication between the first energy-generator module and the second energy-generator module.

Referring to FIG. 3, aspects of the present disclosure are presented for a hub modular enclosure 136 that allows the modular integration of a generator module 140, a smoke evacuation module 126, a suction/irrigation module 128, and an insufflation module 129. The hub modular enclosure 136 further facilitates interactive communication between the modules 140, 126, 128, 129. The generator module 140 can be a generator module with integrated monopolar, bipolar, and ultrasonic components supported in a single housing unit slidably insertable into the hub modular enclosure 136. The generator module 140 can be configured to connect to a monopolar device 142, a bipolar device 144, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128, 129 and interactive communication therebetween.

Generator Hardware

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions—all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; a SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIG. 3, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Figure 4:
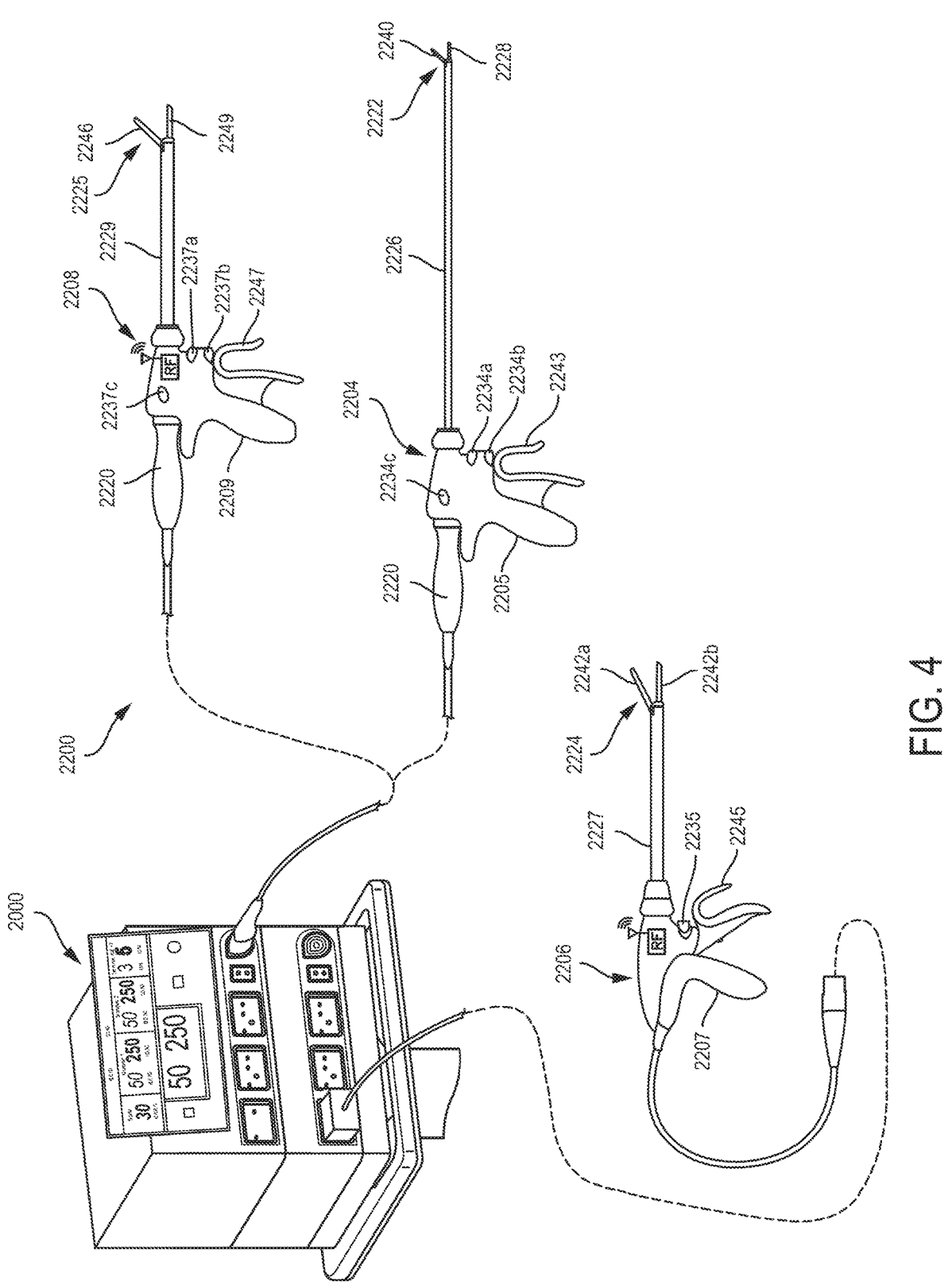
FIG. 4 is a surgical system comprising a generator and various surgical instruments usable therewith, in accordance with at least one aspect of the present disclosure.

FIG. 4 illustrates one form of a surgical system 2200 comprising a modular energy system 2000 and various surgical instruments 2204, 2206, 2208 usable therewith, where the surgical instrument 2204 is an ultrasonic surgical instrument, the surgical instrument 2206 is an RF electrosurgical instrument, and the multifunction surgical instrument 2208 is a combination ultrasonic/RF electrosurgical instrument. The modular energy system 2000 is configurable for use with a variety of surgical instruments. According to various forms, the modular energy system 2000 may be configurable for use with different surgical instruments of different types including, for example, ultrasonic surgical instruments 2204, RF electrosurgical instruments 2206, and multifunction surgical instruments 2208 that integrate RF and ultrasonic energies delivered individually or simultaneously from the modular energy system 2000. Although in the form of FIG. 4 the modular energy system 2000 is shown separate from the surgical instruments 2204, 2206, 2208 in one form, the modular energy system 2000 may be formed integrally with any of the surgical instruments 2204, 2206, 2208 to form a unitary surgical system. The modular energy system 2000 may be configured for wired or wireless communication.

The modular energy system 2000 is configured to drive multiple surgical instruments 2204, 2206, 2208. The first surgical instrument is an ultrasonic surgical instrument 2204 and comprises a handpiece 2205 (HP), an ultrasonic transducer 2220, a shaft 2226, and an end effector 2222. The end effector 2222 comprises an ultrasonic blade 2228 acoustically coupled to the ultrasonic transducer 2220 and a clamp arm 2240. The handpiece 2205 comprises a trigger 2243 to operate the clamp arm 2240 and a combination of the toggle buttons 2234*a*, 2234*b*, 2234*c* to energize and drive the ultrasonic blade 2228 or other function. The toggle buttons 2234*a*, 2234*b*, 2234*c* can be configured to energize the ultrasonic transducer 2220 with the modular energy system 2000.

The modular energy system 2000 also is configured to drive a second surgical instrument 2206. The second surgical instrument 2206 is an RF electrosurgical instrument and comprises a handpiece 2207 (HP), a shaft 2227, and an end effector 2224. The end effector 2224 comprises electrodes in clamp arms 2242*a*, 2242*b* and return through an electrical conductor portion of the shaft 2227. The electrodes are coupled to and energized by a bipolar energy source within the modular energy system 2000. The handpiece 2207 comprises a trigger 2245 to operate the clamp arms 2242*a*, 2242*b* and an energy button 2235 to actuate an energy switch to energize the electrodes in the end effector 2224.

The modular energy system 2000 also is configured to drive a multifunction surgical instrument 2208. The multifunction surgical instrument 2208 comprises a handpiece 2209 (HP), a shaft 2229, and an end effector 2225. The end effector 2225 comprises an ultrasonic blade 2249 and a clamp arm 2246. The ultrasonic blade 2249 is acoustically coupled to the ultrasonic transducer 2220. The ultrasonic transducer 2220 may be separable from or integral to the handpiece 2209. The handpiece 2209 comprises a trigger 2247 to operate the clamp arm 2246 and a combination of the toggle buttons 2237*a*, 2237*b*, 2237*c* to energize and drive the ultrasonic blade 2249 or other function. The toggle buttons 2237*a*, 2237*b*, 2237*c* can be configured to energize the ultrasonic transducer 2220 with the modular energy system 2000 and energize the ultrasonic blade 2249 with a bipolar energy source also contained within the modular energy system 2000.

The modular energy system 2000 is configurable for use with a variety of surgical instruments. According to various forms, the modular energy system 2000 may be configurable for use with different surgical instruments of different types including, for example, the ultrasonic surgical instrument 2204, the RF electrosurgical instrument 2206, and the multifunction surgical instrument 2208 that integrates RF and ultrasonic energies delivered individually or simultaneously from the modular energy system 2000. Although in the form of FIG. 4 the modular energy system 2000 is shown separate from the surgical instruments 2204, 2206, 2208, in another form the modular energy system 2000 may be formed integrally with any one of the surgical instruments 2204, 2206, 2208 to form a unitary surgical system. Further aspects of generators for digitally generating electrical signal waveforms and surgical instruments are described in U.S. Patent Application Publication No. 2017/0086914, which is herein incorporated by reference in its entirety.

Situational Awareness

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control the modular device incorrectly or sub optimally given the particular context-free sensed data. For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

Figure 5:
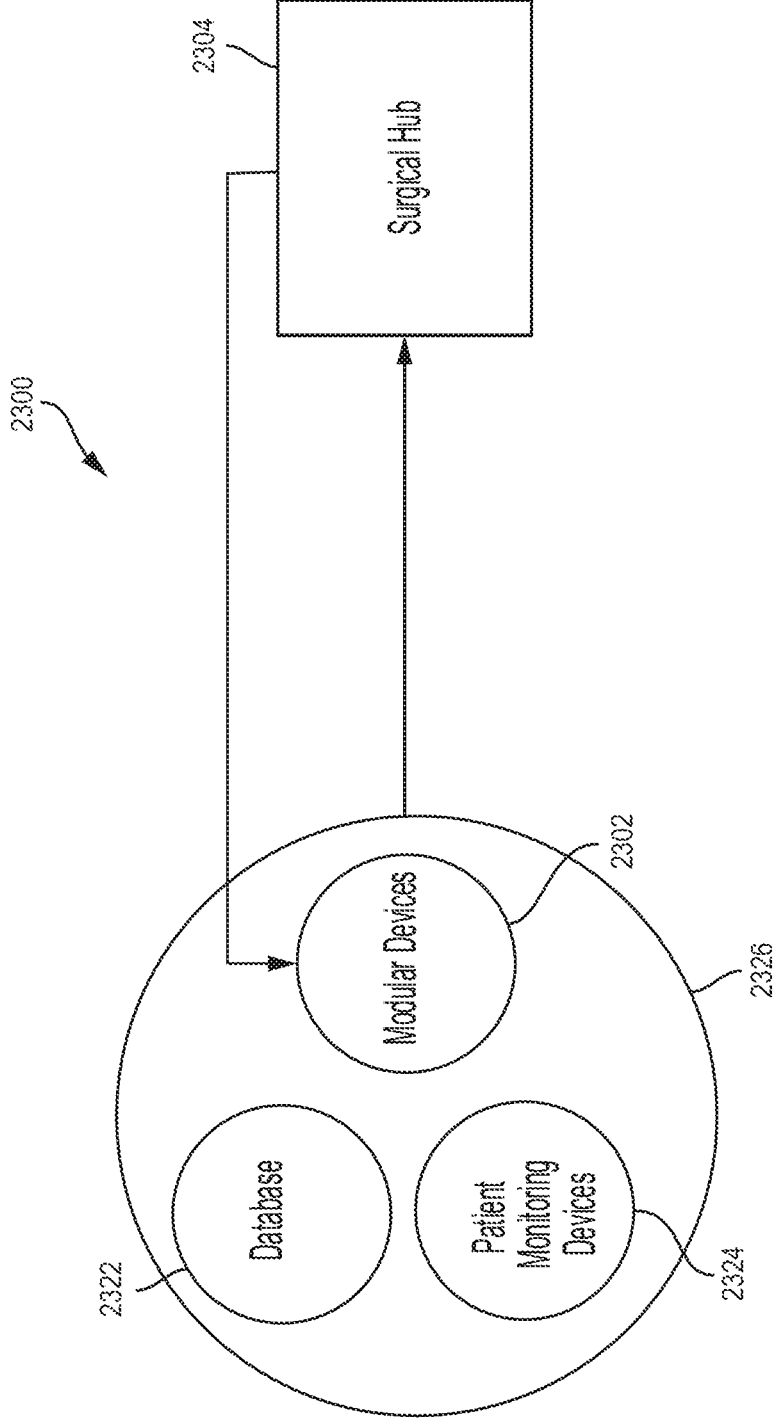
FIG. 5 is a diagram of a situationally aware surgical system, in accordance with at least one aspect of the present disclosure.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 5 illustrates a diagram of a situationally aware surgical system 2300, in accordance with at least one aspect of the present disclosure. In some exemplifications, the data sources 2326 include, for example, the modular devices 2302 (which can include sensors configured to detect parameters associated with the patient and/or the modular device itself), databases 2322 (e.g., an EMR database containing patient records), and patient monitoring devices 2324 (e.g., a blood pressure (BP) monitor and an electrocardiography (EKG) monitor). The surgical hub 2304 can be configured to derive the contextual information pertaining to the surgical procedure from the data based upon, for example, the particular combination(s) of received data or the particular order in which the data is received from the data sources 2326. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 2304 to derive or infer information related to the surgical procedure from received data can be referred to as "situational awareness." In one exemplification, the surgical hub 2304 can incorporate a situational awareness system, which is the hardware and/or programming associated with the surgical hub 2304 that derives contextual information pertaining to the surgical procedure from the received data.

The situational awareness system of the surgical hub 2304 can be configured to derive the contextual information from the data received from the data sources 2326 in a variety of different ways. In one exemplification, the situational awareness system includes a pattern recognition system, or machine learning system (e.g., an artificial neural network), that has been trained on training data to correlate various inputs (e.g., data from databases 2322, patient monitoring devices 2324, and/or modular devices 2302) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 2302. In one exemplification, the contextual information received by the situational awareness system of the surgical hub 2304 is associated with a particular control adjustment or set of control adjustments for one or more modular devices 2302. In another exemplification, the situational awareness system includes a further machine learning system, lookup table, or other such system, which generates or retrieves one or more control adjustments for one or more modular devices 2302 when provided the contextual information as input.

A surgical hub 2304 incorporating a situational awareness system provides a number of benefits for the surgical system 2300. One benefit includes improving the interpretation of sensed and collected data, which would in turn improve the processing accuracy and/or the usage of the data during the course of a surgical procedure. To return to a previous example, a situationally aware surgical hub 2304 could determine what type of tissue was being operated on; therefore, when an unexpectedly high force to close the surgical instrument's end effector is detected, the situationally aware surgical hub 2304 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 2304 could infer whether a surgical procedure being performed is a thoracic or an abdominal procedure, allowing the surgical hub 2304 to determine whether the tissue clamped by an end effector of the surgical stapling and cutting instrument is lung (for a thoracic procedure) or stomach (for an abdominal procedure) tissue. The surgical hub 2304 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 2304 could determine whether the surgical site is under pressure (by determining that the surgical procedure is utilizing insufflation) and determine the procedure type. As a procedure type is generally performed in a specific body cavity, the surgical hub 2304 could then control the motor rate of the smoke evacuator appropriately for the body cavity being operated in. Thus, a situationally aware surgical hub 2304 could provide a consistent amount of smoke evacuation for both thoracic and abdominal procedures.

As yet another example, the type of procedure being performed can affect the optimal energy level at which an ultrasonic surgical instrument or radio frequency (RF) electrosurgical instrument operates. Arthroscopic procedures, for example, require higher energy levels because the end effector of the ultrasonic surgical instrument or RF electrosurgical instrument is immersed in fluid. A situationally aware surgical hub 2304 could determine whether the surgical procedure is an arthroscopic procedure. The surgical hub 2304 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 2304 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 2304 can be configured to adjust the energy level for the ultrasonic surgical instrument or RF electrosurgical instrument throughout the course of a surgical procedure, rather than just on a procedure-by-procedure basis. A situationally aware surgical hub 2304 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 2326 to improve the conclusions that the surgical hub 2304 draws from one data source 2326. A situationally aware surgical hub 2304 could augment data that it receives from the modular devices 2302 with contextual information that it has built up regarding the surgical procedure from other data sources 2326. For example, a situationally aware surgical hub 2304 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 2304 can be further configured to compare a physiologic measurement (e.g., blood pressure sensed by a BP monitor communicably connected to the surgical hub 2304) with the visual or image data of hemostasis (e.g., from a medical imaging device 124 (FIG. 2) communicably coupled to the surgical hub 2304) to make a determination on the integrity of the staple line or tissue weld. In other words, the situational awareness system of the surgical hub 2304 can consider the physiological measurement data to provide additional context in analyzing the visualization data. The additional context can be useful when the visualization data may be inconclusive or incomplete on its own.

Another benefit includes proactively and automatically controlling the paired modular devices 2302 according to the particular step of the surgical procedure that is being performed to reduce the number of times that medical personnel are required to interact with or control the surgical system 2300 during the course of a surgical procedure. For example, a situationally aware surgical hub 2304 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 2304 could determine whether the current or subsequent step of the surgical procedure requires a different view or degree of magnification on the display according to the feature(s) at the surgical site that the surgeon is expected to need to view. The surgical hub 2304 could then proactively change the displayed view (supplied by, e.g., a medical imaging device for the visualization system 108) accordingly so that the display automatically adjusts throughout the surgical procedure.

As yet another example, a situationally aware surgical hub 2304 could determine which step of the surgical procedure is being performed or will subsequently be performed and whether particular data or comparisons between data will be required for that step of the surgical procedure. The surgical hub 2304 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 2304 could determine whether the operating theater is setup properly or optimally for the surgical procedure to be performed. The surgical hub 2304 can be configured to determine the type of surgical procedure being performed, retrieve the corresponding checklists, product location, or setup needs (e.g., from a memory), and then compare the current operating theater layout to the standard layout for the type of surgical procedure that the surgical hub 2304 determines is being performed. In one exemplification, the surgical hub 2304 can be configured to compare the list of items for the procedure (scanned by a scanner, for example) and/or a list of devices paired with the surgical hub 2304 to a recommended or anticipated manifest of items and/or devices for the given surgical procedure. If there are any discontinuities between the lists, the surgical hub 2304 can be configured to provide an alert indicating that a particular modular device 2302, patient monitoring device 2324, and/or other surgical item is missing. In one exemplification, the surgical hub 2304 can be configured to determine the relative distance or position of the modular devices 2302 and patient monitoring devices 2324 via proximity sensors, for example. The surgical hub 2304 can compare the relative positions of the devices to a recommended or anticipated layout for the particular surgical procedure. If there are any discontinuities between the layouts, the surgical hub 2304 can be configured to provide an alert indicating that the current layout for the surgical procedure deviates from the recommended layout.

As another example, a situationally aware surgical hub 2304 could determine whether the surgeon (or other medical personnel) was making an error or otherwise deviating from the expected course of action during the course of a surgical procedure. For example, the surgical hub 2304 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 2304 determined is being performed. In one exemplification, the surgical hub 2304 can be configured to provide an alert indicating that an unexpected action is being performed or an unexpected device is being utilized at the particular step in the surgical procedure.

Overall, the situational awareness system for the surgical hub 2304 improves surgical procedure outcomes by adjusting the surgical instruments (and other modular devices 2302) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 2302 in the surgical theater according to the specific context of the procedure.

Modular Energy System

ORs everywhere in the world are a tangled web of cords, devices, and people due to the amount of equipment required to perform surgical procedures. Surgical capital equipment tends to be a major contributor to this issue because most surgical capital equipment performs a single, specialized task. Due to their specialized nature and the surgeons' needs to utilize multiple different types of devices during the course of a single surgical procedure, an OR may be forced to be stocked with two or even more pieces of surgical capital equipment, such as energy generators. Each of these pieces of surgical capital equipment must be individually plugged into a power source and may be connected to one or more other devices that are being passed between OR personnel, creating a tangle of cords that must be navigated. Another issue faced in modern ORs is that each of these specialized pieces of surgical capital equipment has its own user interface and must be independently controlled from the other pieces of equipment within the OR. This creates complexity in properly controlling multiple different devices in connection with each other and forces users to be trained on and memorize different types of user interfaces (which may further change based upon the task or surgical procedure being performed, in addition to changing between each piece of capital equipment). This cumbersome, complex process can necessitate the need for even more individuals to be present within the OR and can create danger if multiple devices are not properly controlled in tandem with each other. Therefore, consolidating surgical capital equipment technology into singular systems that are able to flexibly address surgeons' needs to reduce the footprint of surgical capital equipment within ORs would simplify the user experience, reduce the amount of clutter in ORs, and prevent difficulties and dangers associated with simultaneously controlling multiple pieces of capital equipment. Further, making such systems expandable or customizable would allow for new technology to be conveniently incorporated into existing surgical systems, obviating the need to replace entire surgical systems or for OR personnel to learn new user interfaces or equipment controls with each new technology.

As described in FIGS. 1-3, a surgical hub 106 can be configured to interchangeably receive a variety of modules, which can in turn interface with surgical devices (e.g., a surgical instrument or a smoke evacuator) or provide various other functions (e.g., communications). In one aspect, a surgical hub 106 can be embodied as a modular energy system 2000, which is illustrated in connection with FIGS. 6-12. The modular energy system 2000 can include a variety of different modules 2001 that are connectable together in a stacked configuration. In one aspect, the modules 2001 can be both physically and communicably coupled together when stacked or otherwise connected together into a singular assembly. Further, the modules 2001 can be interchangeably connectable together in different combinations or arrangements. In one aspect, each of the modules 2001 can include a consistent or universal array of connectors disposed along their upper and lower surfaces, thereby allowing any module 2001 to be connected to another module 2001 in any arrangement (except that, in some aspects, a particular module type, such as the header module 2002, can be configured to serve as the uppermost module within the stack, for example). In an alternative aspect, the modular energy system 2000 can include a housing that is configured to receive and retain the modules 2001, as is shown in FIG. 3. The modular energy system 2000 can also include a variety of different components or accessories that are also connectable to or otherwise associatable with the modules 2001. In another aspect, the modular energy system 2000 can be embodied as a generator module 140 (FIG. 3) of a surgical hub 106. In yet another aspect, the modular energy system 2000 can be a distinct system from a surgical hub 106. In such aspects, the modular energy system 2000 can be communicably couplable to a surgical hub 206 for transmitting and/or receiving data therebetween.

Figure 6:
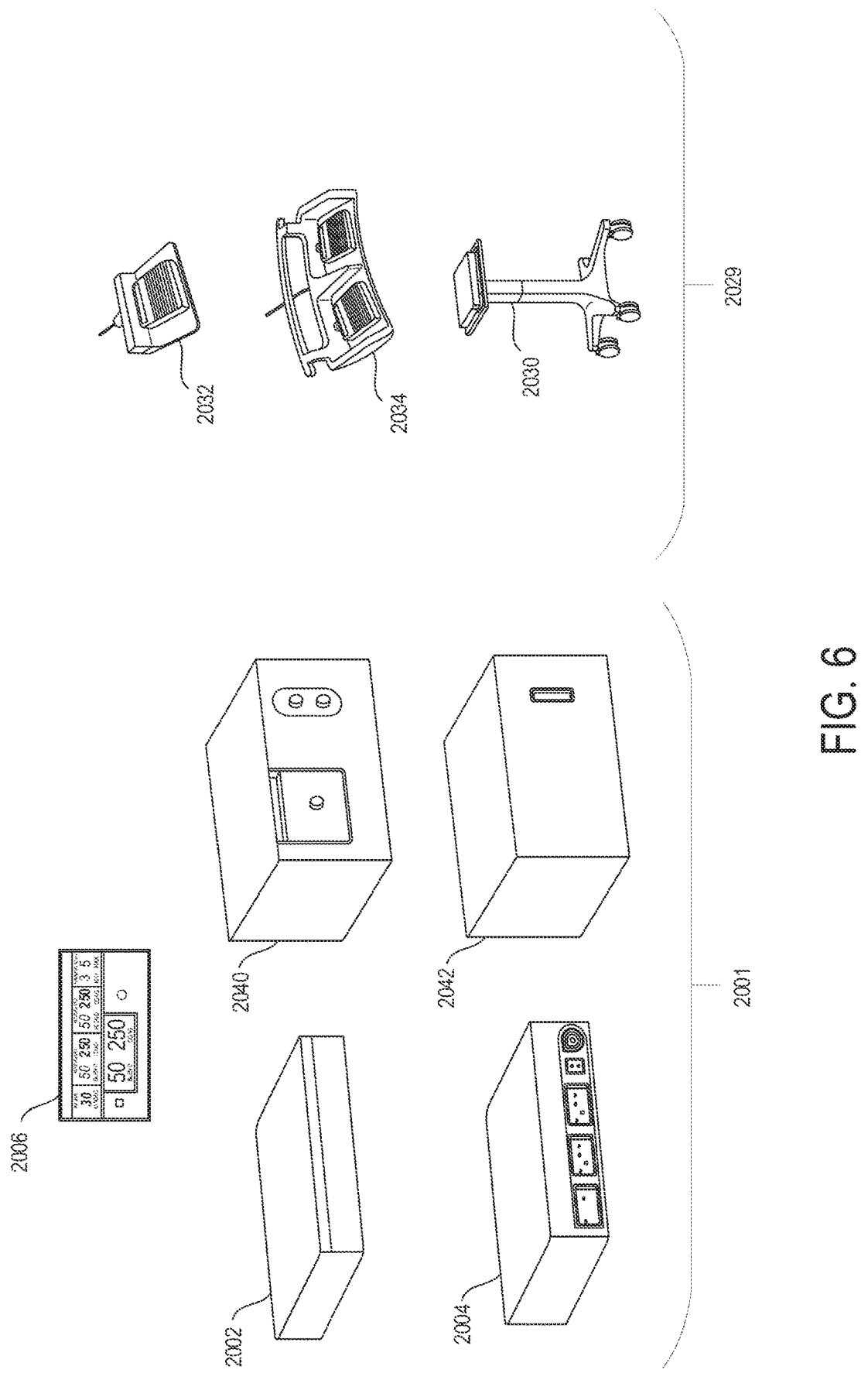
FIG. 6 is a diagram of various modules and other components that are combinable to customize modular energy systems, in accordance with at least one aspect of the present disclosure.

The modular energy system 2000 can be assembled from a variety of different modules 2001, some examples of which are illustrated in FIG. 6. Each of the different types of modules 2001 can provide different functionality, thereby allowing the modular energy system 2000 to be assembled into different configurations to customize the functions and capabilities of the modular energy system 2000 by customizing the modules 2001 that are included in each modular energy system 2000. The modules 2001 of the modular energy system 2000 can include, for example, a header module 2002 (which can include a display screen 2006), an energy module 2004, a technology module 2040, and a visualization module 2042. In the depicted aspect, the header module 2002 is configured to serve as the top or uppermost module within the modular energy system stack and can thus lack connectors along its top surface. In another aspect, the header module 2002 can be configured to be positioned at the bottom or the lowermost module within the modular energy system stack and can thus lack connectors along its bottom surface. In yet another aspect, the header module 2002 can be configured to be positioned at an intermediate position within the modular energy system stack and can thus include connectors along both its bottom and top surfaces. The header module 2002 can be configured to control the system-wide settings of each module 2001 and component connected thereto through physical controls 2011 thereon and/or a graphical user interface (GUI) 2008 rendered on the display screen 2006. Such settings could include the activation of the modular energy system 2000, the volume of alerts, the footswitch settings, the settings icons, the appearance or configuration of the user interface, the surgeon profile logged into the modular energy system 2000, and/or the type of surgical procedure being performed. The header module 2002 can also be configured to provide communications, processing, and/or power for the modules 2001 that are connected to the header module 2002. The energy module 2004, which can also be referred to as a generator module 140 (FIG. 3), can be configured to generate one or multiple energy modalities for driving electrosurgical and/or ultrasonic surgical instruments connected thereto. The technology module 2040 can be configured to provide additional or expanded control algorithms (e.g., electrosurgical or ultrasonic control algorithms for controlling the energy output of the energy module 2004). The visualization module 2042 can be configured to interface with visualization devices (i.e., scopes) and accordingly provide increased visualization capabilities.

The modular energy system 2000 can further include a variety of accessories 2029 that are connectable to the modules 2001 for controlling the functions thereof or that are otherwise configured to work on conjunction with the modular energy system 2000. The accessories 2029 can include, for example, a single-pedal footswitch 2032, a dual-pedal footswitch 2034, and a cart 2030 for supporting the modular energy system 2000 thereon. The footswitches 2032,2034 can be configured to control the activation or function of particular energy modalities output by the energy module 2004, for example.

By utilizing modular components, the depicted modular energy system 2000 provides a surgical platform that grows with the availability of technology and is customizable to the needs of the facility and/or surgeons. Further, the modular energy system 2000 supports combo devices (e.g., dual electrosurgical and ultrasonic energy generators) and supports software-driven algorithms for customized tissue effects. Still further, the surgical system architecture reduces the capital footprint by combining multiple technologies critical for surgery into a single system.

The various modular components utilizable in connection with the modular energy system 2000 can include monopolar energy generators, bipolar energy generators, dual electrosurgical/ultrasonic energy generators, display screens, and various other modules and/or other components, some of which are also described above in connection with FIGS. 1-3.

Figure 7B:
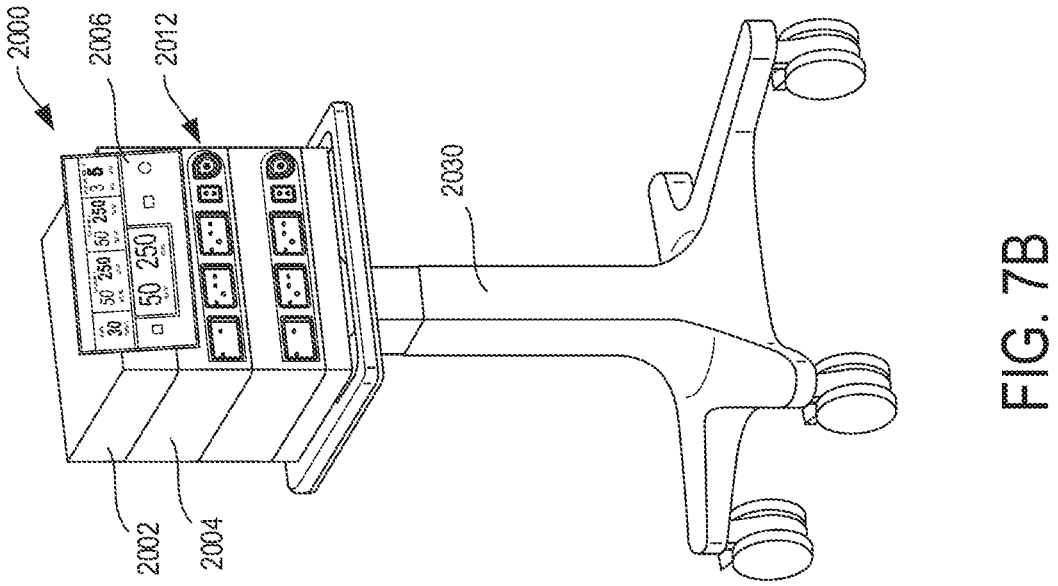
FIG. 7B is the modular energy system shown in FIG. 7A mounted to a cart, in accordance with at least one aspect of the present disclosure.
Figure 7A:
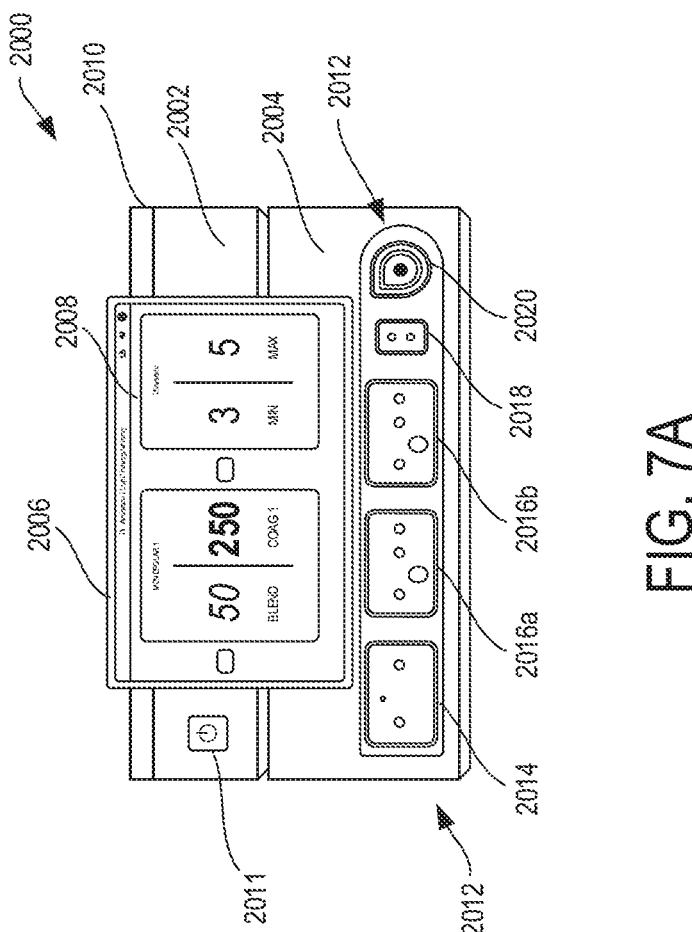
FIG. 7A is a first illustrative modular energy system configuration including a header module and a display screen that renders a graphical user interface (GUI) for relaying information regarding modules connected to the header module, in accordance with at least one aspect of the present disclosure.
Figure 11:
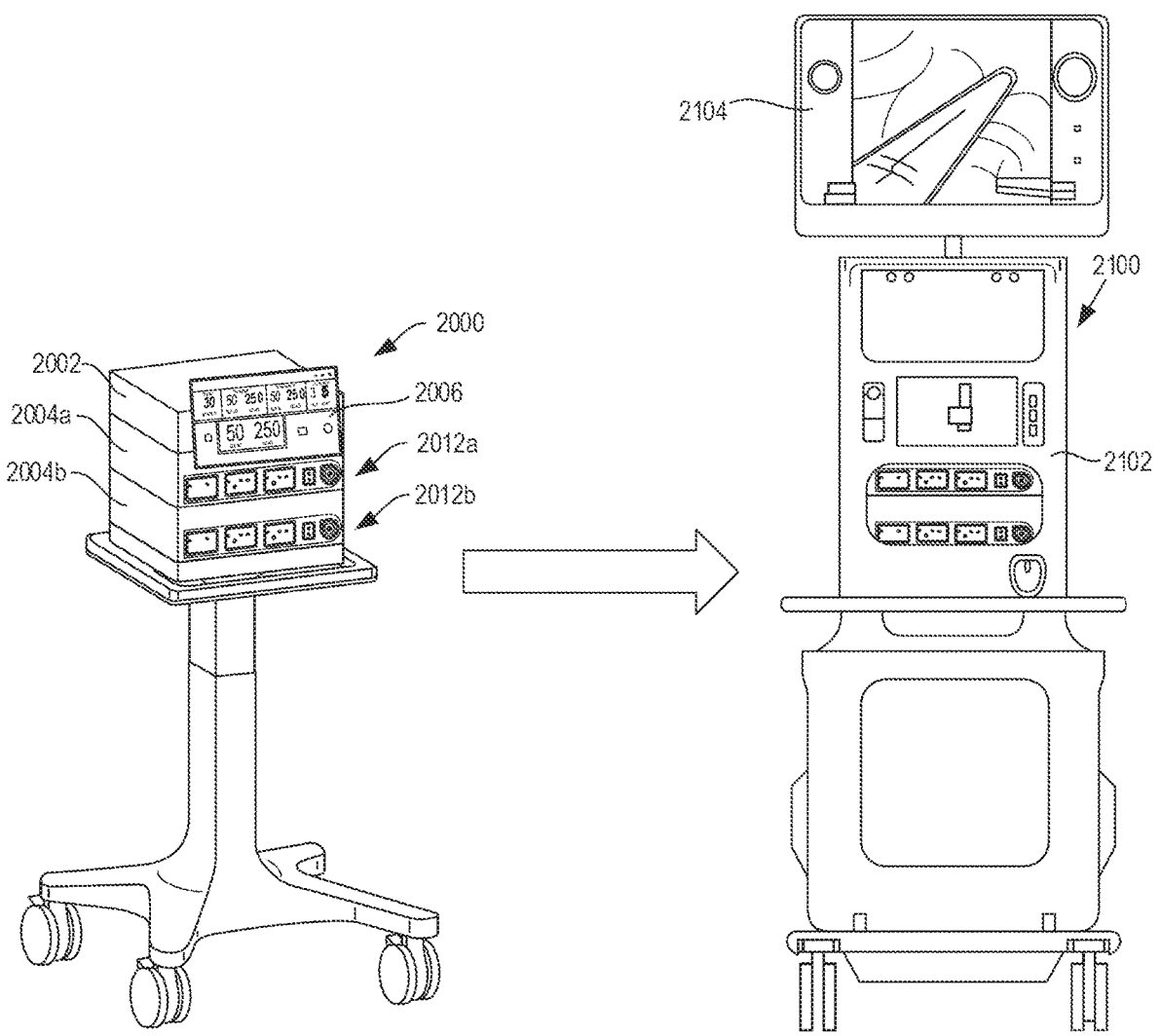
FIG. 11 is a diagram of a modular energy system including communicably connectable surgical platforms, in accordance with at least one aspect of the present disclosure.

Referring now to FIG. 7A, the header module 2002 can, in some aspects, include a display screen 2006 that renders a GUI 2008 for relaying information regarding the modules 2001 connected to the header module 2002. In some aspects, the GUI 2008 of the display screen 2006 can provide a consolidated point of control of all of the modules 2001 making up the particular configuration of the modular energy system 2000. Various aspects of the GUI 2008 are discussed in fuller detail below in connection with FIG. 12. In alternative aspects, the header module 2002 can lack the display screen 2006 or the display screen 2006 can be detachably connected to the housing 2010 of the header module 2002. In such aspects, the header module 2002 can be communicably couplable to an external system that is configured to display the information generated by the modules 2001 of the modular energy system 2000. For example, in robotic surgical applications, the modular energy system 2000 can be communicably couplable to a robotic cart or robotic control console, which is configured to display the information generated by the modular energy system 2000 to the operator of the robotic surgical system. As another example, the modular energy system 2000 can be communicably couplable to a mobile display that can be carried or secured to a surgical staff member for viewing thereby. In yet another example, the modular energy system 2000 can be communicably couplable to a surgical hub 2100 or another computer system that can include a display 2104, as is illustrated in FIG. 11. In aspects utilizing a user interface that is separate from or otherwise distinct from the modular energy system 2000, the user interface can be wirelessly connectable with the modular energy system 2000 as a whole or one or more modules 2001 thereof such that the user interface can display information from the connected modules 2001 thereon.

Referring still to FIG. 7A, the energy module 2004 can include a port assembly 2012 including a number of different ports configured to deliver different energy modalities to corresponding surgical instruments that are connectable thereto. In the particular aspect illustrated in FIGS. 6-12, the port assembly 2012 includes a bipolar port 2014, a first monopolar port 2016a, a second monopolar port 2016b, a neutral electrode port 2018 (to which a monopolar return pad is connectable), and a combination energy port 2020. However, this particular combination of ports is simply provided for illustrative purposes and alternative combinations of ports and/or energy modalities may be possible for the port assembly 2012.

As noted above, the modular energy system 2000 can be assembled into different configurations. Further, the different configurations of the modular energy system 2000 can also be utilizable for different surgical procedure types and/or different tasks. For example, FIGS. 7A and 7B illustrate a first illustrative configuration of the modular energy system 2000 including a header module 2002 (including a display screen 2006) and an energy module 2004 connected together. Such a configuration can be suitable for laparoscopic and open surgical procedures, for example.

Figure 8A:
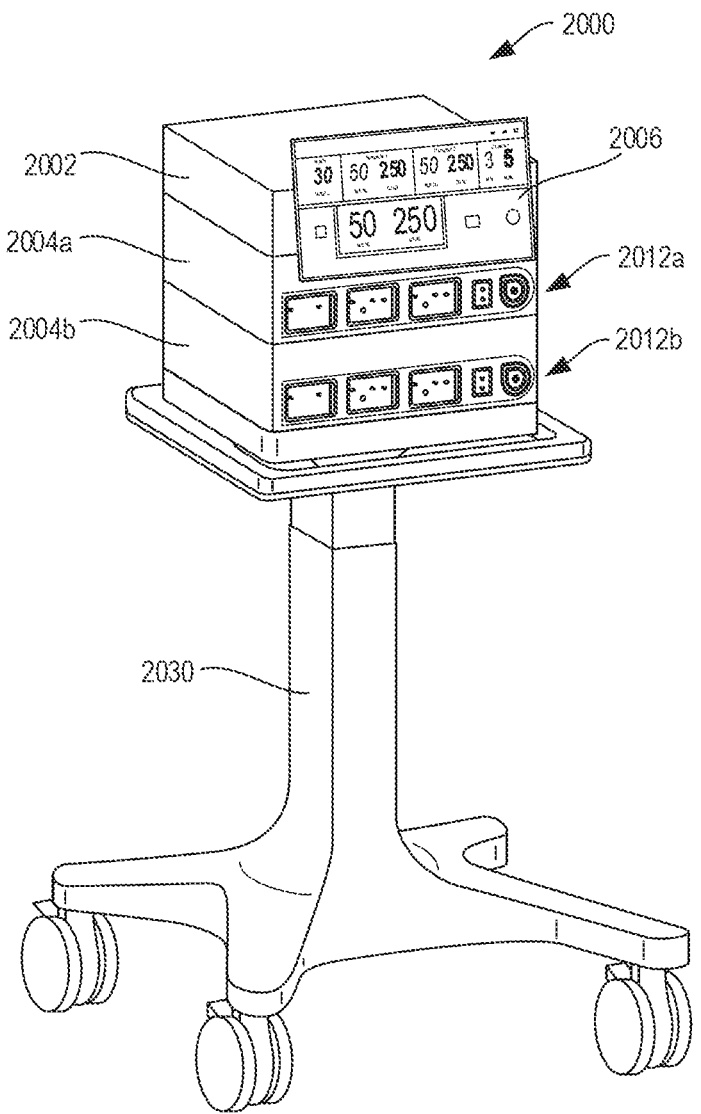
FIG. 8A is a second illustrative modular energy system configuration including a header module, a display screen, an energy module, and an expanded energy module connected together and mounted to a cart, in accordance with at least one aspect of the present disclosure.
Figure 8B:
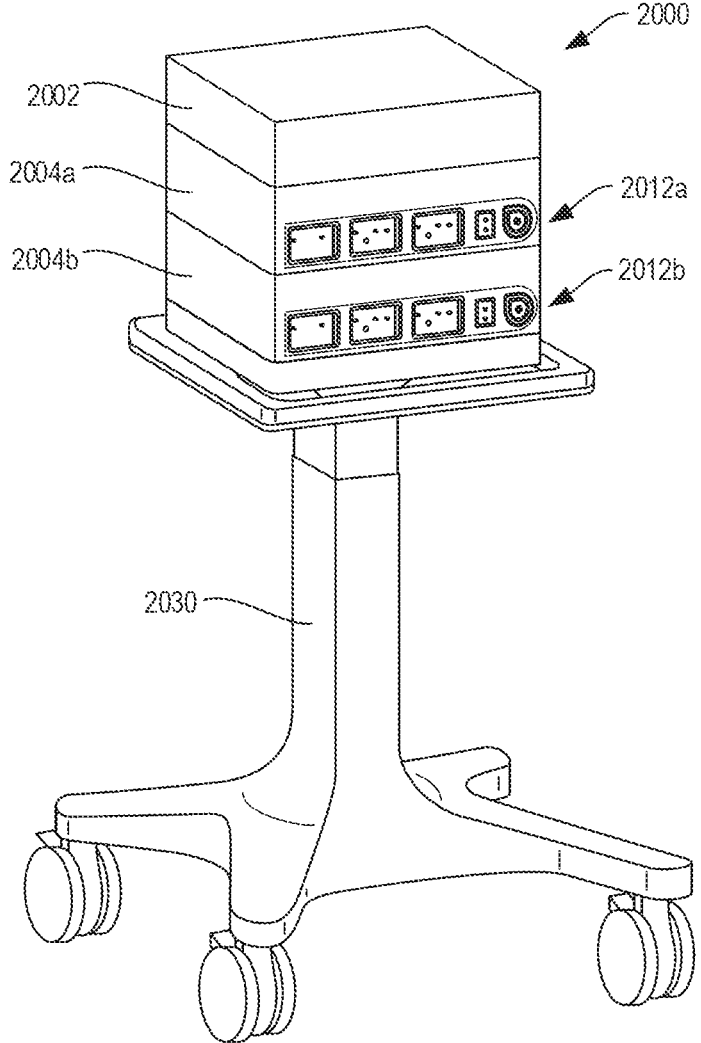
FIG. 8B is a third illustrative modular energy system configuration that is similar to the second configuration shown in FIG. 7A, except that the header module lacks a display screen, in accordance with at least one aspect of the present disclosure.

FIG. 8A illustrates a second illustrative configuration of the modular energy system 2000 including a header module 2002 (including a display screen 2006), a first energy module 2004a, and a second energy module 2004b connected together. By stacking two energy modules 2004a, 2004b, the modular energy system 2000 can provide a pair of port assemblies 2012a, 2012b for expanding the array of energy modalities deliverable by the modular energy system 2000 from the first configuration. The second configuration of the modular energy system 2000 can accordingly accommodate more than one bipolar/monopolar electrosurgical instrument, more than two bipolar/monopolar electrosurgical instruments, and so on. Such a configuration can be suitable for particularly complex laparoscopic and open surgical procedures. FIG. 8B illustrates a third illustrative configuration that is similar to the second configuration, except that the header module 2002 lacks a display screen 2006. This configuration can be suitable for robotic surgical applications or mobile display applications, as noted above.

Figure 9:
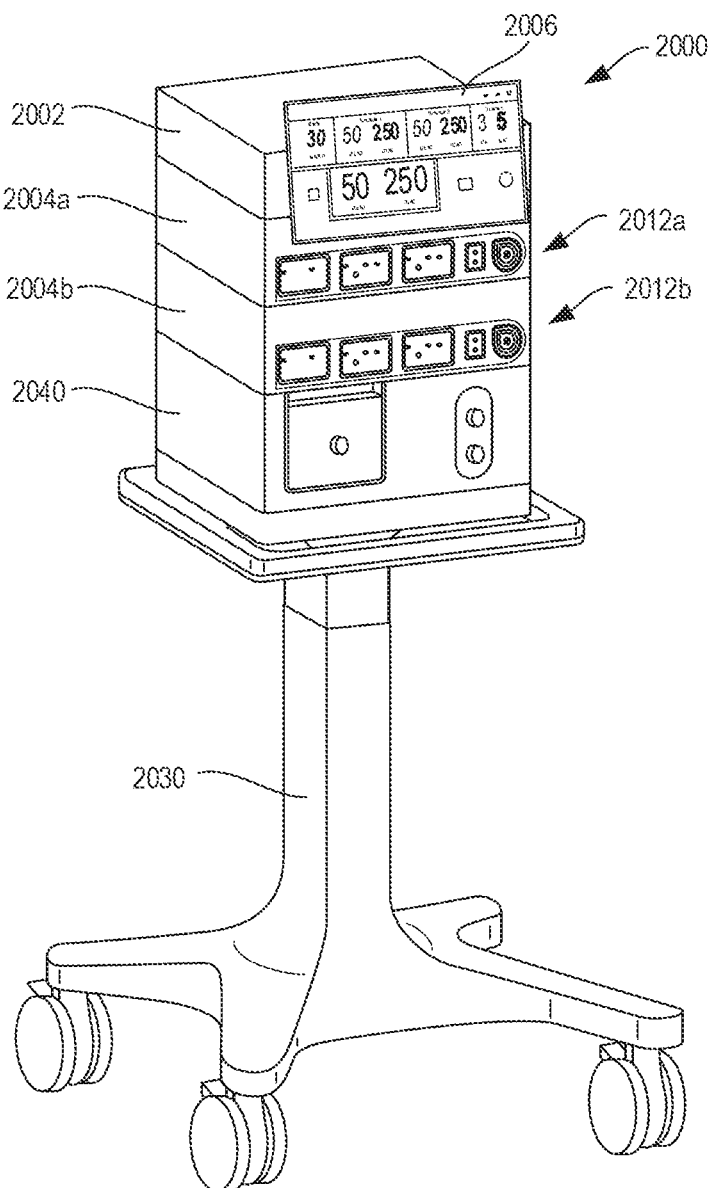
FIG. 9 is a fourth illustrative modular energy system configuration including a header module, a display screen, an energy module, an expanded energy module, and a technology module connected together and mounted to a cart, in accordance with at least one aspect of the present disclosure.

FIG. 9 illustrates a fourth illustrative configuration of the modular energy system 2000 including a header module 2002 (including a display screen 2006), a first energy module 2004a, a second energy module 2004b, and a technology module 2040 connected together. Such a configuration can be suitable for surgical applications where particularly complex or computation-intensive control algorithms are required. Alternatively, the technology module 2040 can be a newly released module that supplements or expands the capabilities of previously released modules (such as the energy module 2004).

Figure 10:
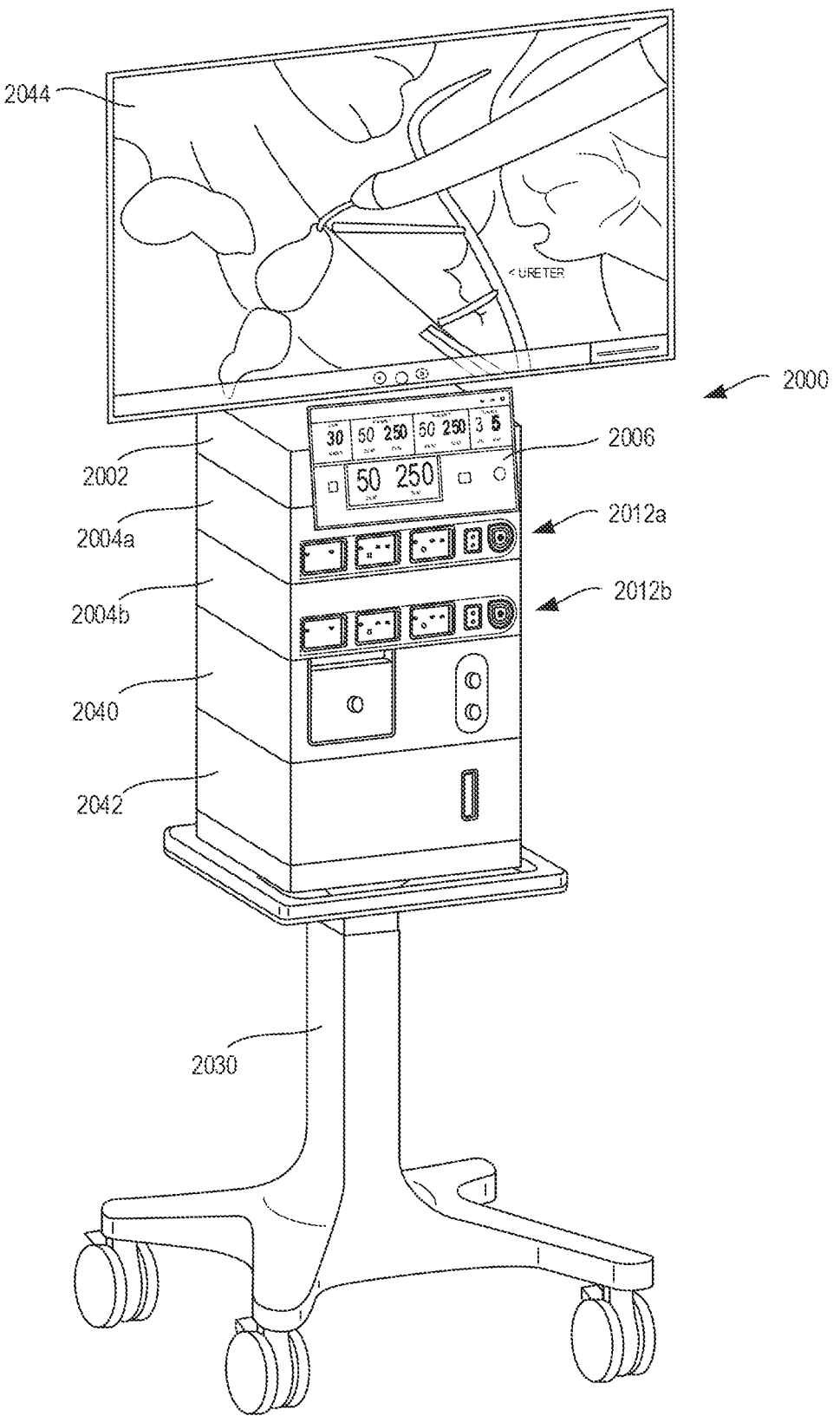
FIG. 10 is a fifth illustrative modular energy system configuration including a header module, a display screen, an energy module, an expanded energy module, a technology module, and a visualization module connected together and mounted to a cart, in accordance with at least one aspect of the present disclosure.

FIG. 10 illustrates a fifth illustrative configuration of the modular energy system 2000 including a header module 2002 (including a display screen 2006), a first energy module 2004a, a second energy module 2004b, a technology module 2040, and a visualization module 2042 connected together. Such a configuration can be suitable for endoscopic procedures by providing a dedicated surgical display 2044 for relaying the video feed from the scope coupled to the visualization module 2042. It should be noted that the configurations illustrated in FIGS. 7A-11 and described above are provided simply to illustrate the various concepts of the modular energy system 2000 and should not be interpreted to limit the modular energy system 2000 to the particular aforementioned configurations.

As noted above, the modular energy system 2000 can be communicably couplable to an external system, such as a surgical hub 2100 as illustrated in FIG. 11. Such external systems can include a display screen 2104 for displaying a visual feed from an endoscope (or a camera or another such visualization device) and/or data from the modular energy system 2000. Such external systems can also include a computer system 2102 for performing calculations or otherwise analyzing data generated or provided by the modular energy system 2000, controlling the functions or modes of the modular energy system 2000, and/or relaying data to a cloud computing system or another computer system. Such external systems could also coordinate actions between multiple modular energy systems 2000 and/or other surgical systems (e.g., a visualization system 108 and/or a robotic system 110 as described in connection with FIGS. 1 and 2).

Figure 12:
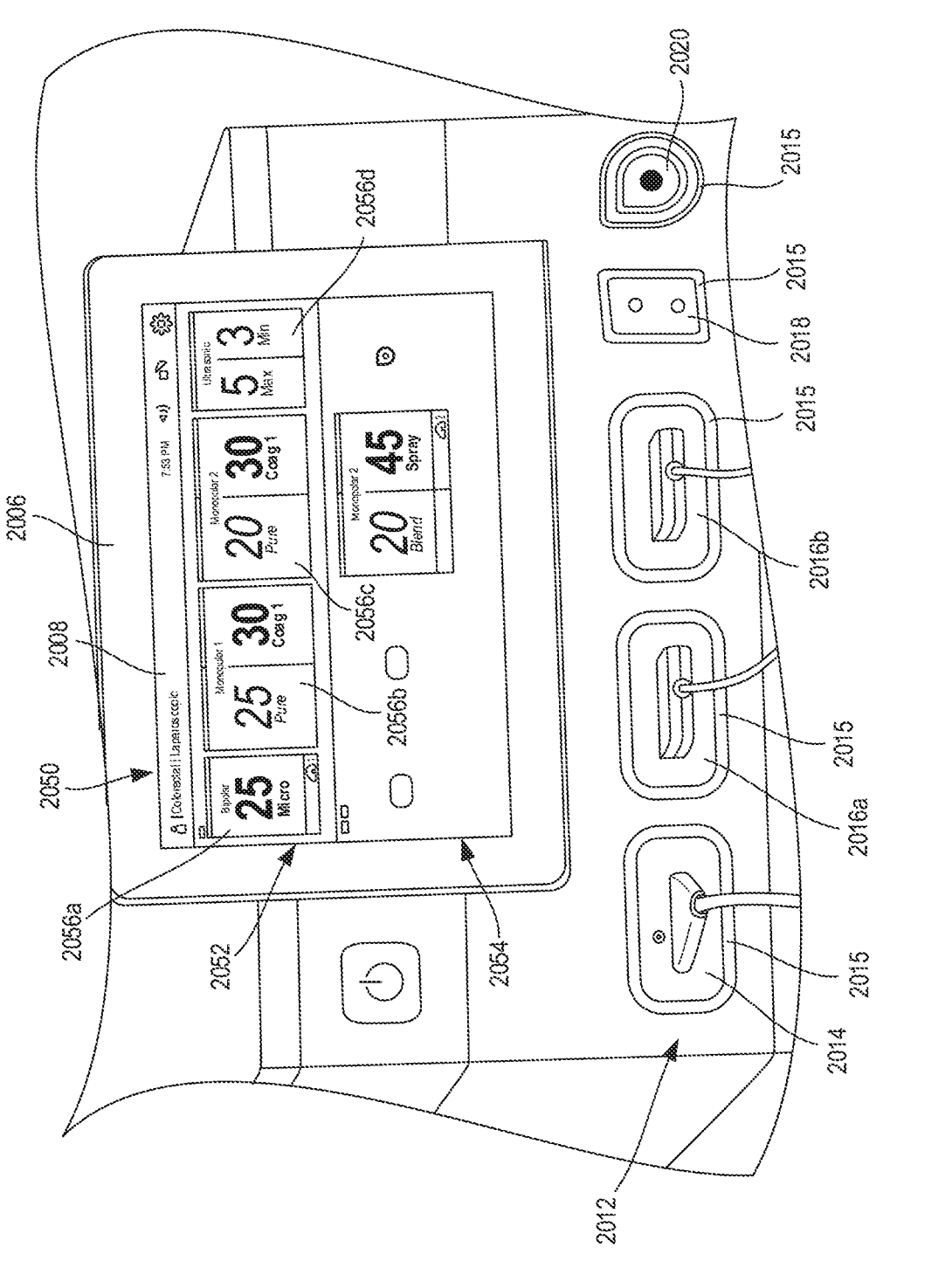
FIG. 12 is a perspective view of a header module of a modular energy system including a user interface, in accordance with at least one aspect of the present disclosure.

Referring now to FIG. 12, in some aspects, the header module 2002 can include or support a display 2006 configured for displaying a GUI 2008, as noted above. The display screen 2006 can include a touchscreen for receiving input from users in addition to displaying information. The controls displayed on the GUI 2008 can correspond to the module(s) 2001 that are connected to the header module 2002. In some aspects, different portions or areas of the GUI 2008 can correspond to particular modules 2001. For example, a first portion or area of the GUI 2008 can correspond to a first module and a second portion or area of the GUI 2008 can correspond to a second module. As different and/or additional modules 2001 are connected to the modular energy system stack, the GUI 2008 can adjust to accommodate the different and/or additional controls for each newly added module 2001 or remove controls for each module 2001 that is removed. Each portion of the display corresponding to a particular module connected to the header module 2002 can display controls, data, user prompts, and/or other information corresponding to that module. For example, in FIG. 12, a first or upper portion 2052 of the depicted GUI 2008 displays controls and data associated with an energy module 2004 that is connected to the header module 2002. In particular, the first portion 2052 of the GUI 2008 for the energy module 2004 provides first widget 2056a corresponding to the bipolar port 2014, a second widget 2056b corresponding to the first monopolar port 2016a, a third widget 2056c corresponding to the second monopolar port 2016b, and a fourth widget 2056d corresponding to the combination energy port 2020. Each of these widgets 2056a-d provides data related to its corresponding port of the port assembly 2012 and controls for controlling the modes and other features of the energy modality delivered by the energy module 2004 through the respective port of the port assembly 2012. For example, the widgets 2056a-d can be configured to display the power level of the surgical instrument connected to the respective port, change the operational mode of the surgical instrument connected to the respective port (e.g., change a surgical instrument from a first power level to a second power level and/or change a monopolar surgical instrument from a "spray" mode to a "blend" mode), and so on.

In one aspect, the header module 2002 can include various physical controls 2011 in addition to or in lieu of the GUI 2008. Such physical controls 2011 can include, for example, a power button that controls the application of power to each module 2001 that is connected to the header module 2002 in the modular energy system 2000. Alternatively, the power button can be displayed as part of the GUI 2008. Therefore, the header module 2002 can serve as a single point of contact and obviate the need to individually activate and deactivate each individual module 2001 from which the modular energy system 2000 is constructed.

In one aspect, the header module 2002 can display still images, videos, animations, and/or information associated with the surgical modules 2001 of which the modular energy system 2000 is constructed or the surgical devices that are communicably coupled to the modular energy system 2000. The still images and/or videos displayed by the header module 2002 can be received from an endoscope or another visualization device that is communicably coupled to the modular energy system 2000. The animations and/or information of the GUI 2008 can be overlaid on or displayed adjacent to the images or video feed.

In one aspect, the modules 2001 other than the header module 2002 can be configured to likewise relay information to users. For example, the energy module 2004 can include light assemblies 2015 disposed about each of the ports of the port assembly 2012. The light assemblies 2015 can be configured to relay information to the user regarding the port according to their color or state (e.g., flashing). For example, the light assemblies 2015 can change from a first color to a second color when a plug is fully seated within the respective port. In one aspect, the color or state of the light assemblies 2015 can be controlled by the header module 2002. For example, the header module 2002 can cause the light assembly 2015 of each port to display a color corresponding to the color display for the port on the GUI 2008.

Figure 13:
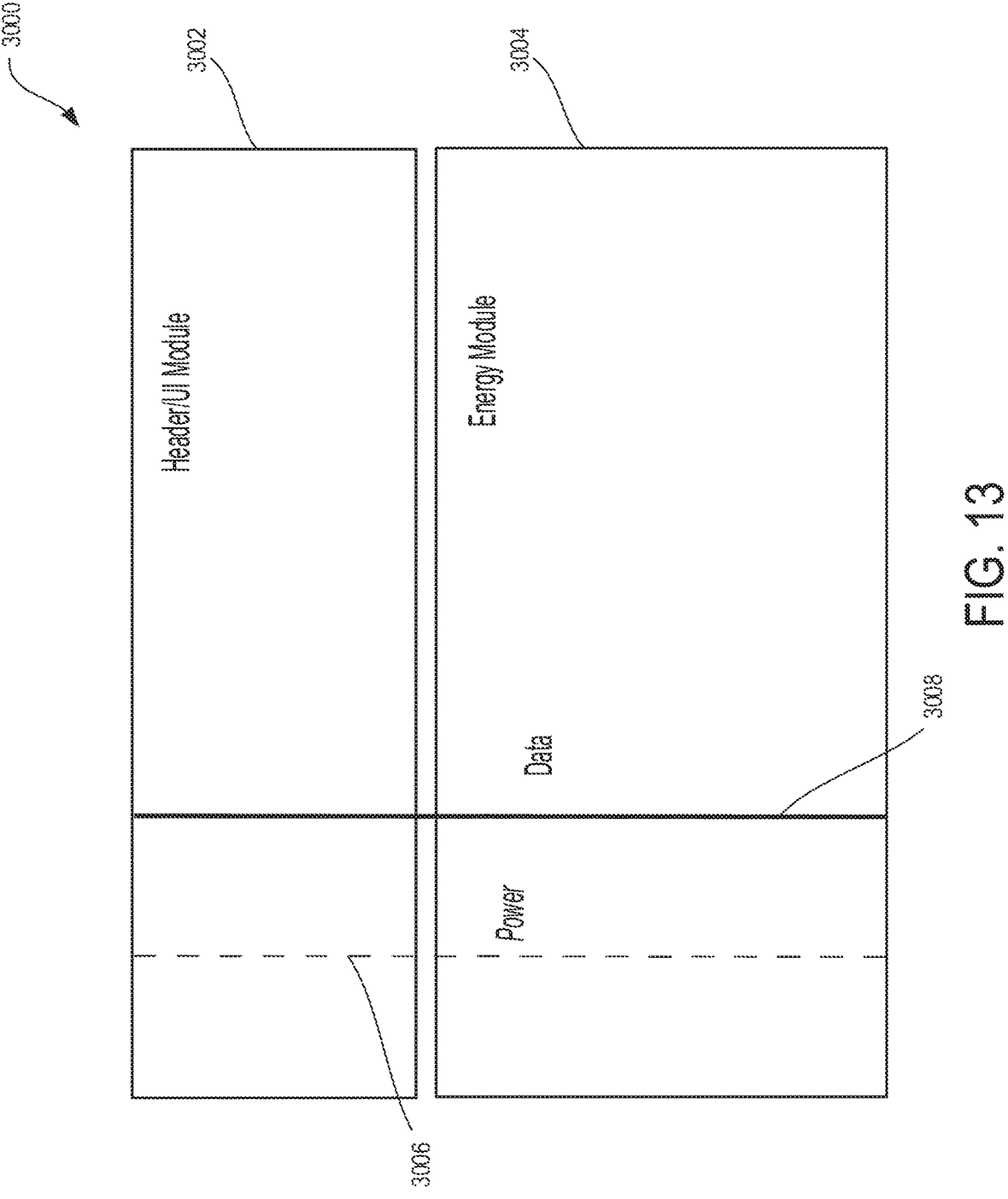
FIG. 13 is a block diagram of a stand-alone hub configuration of a modular energy system, in accordance with at least one aspect of the present disclosure.
Figure 14:
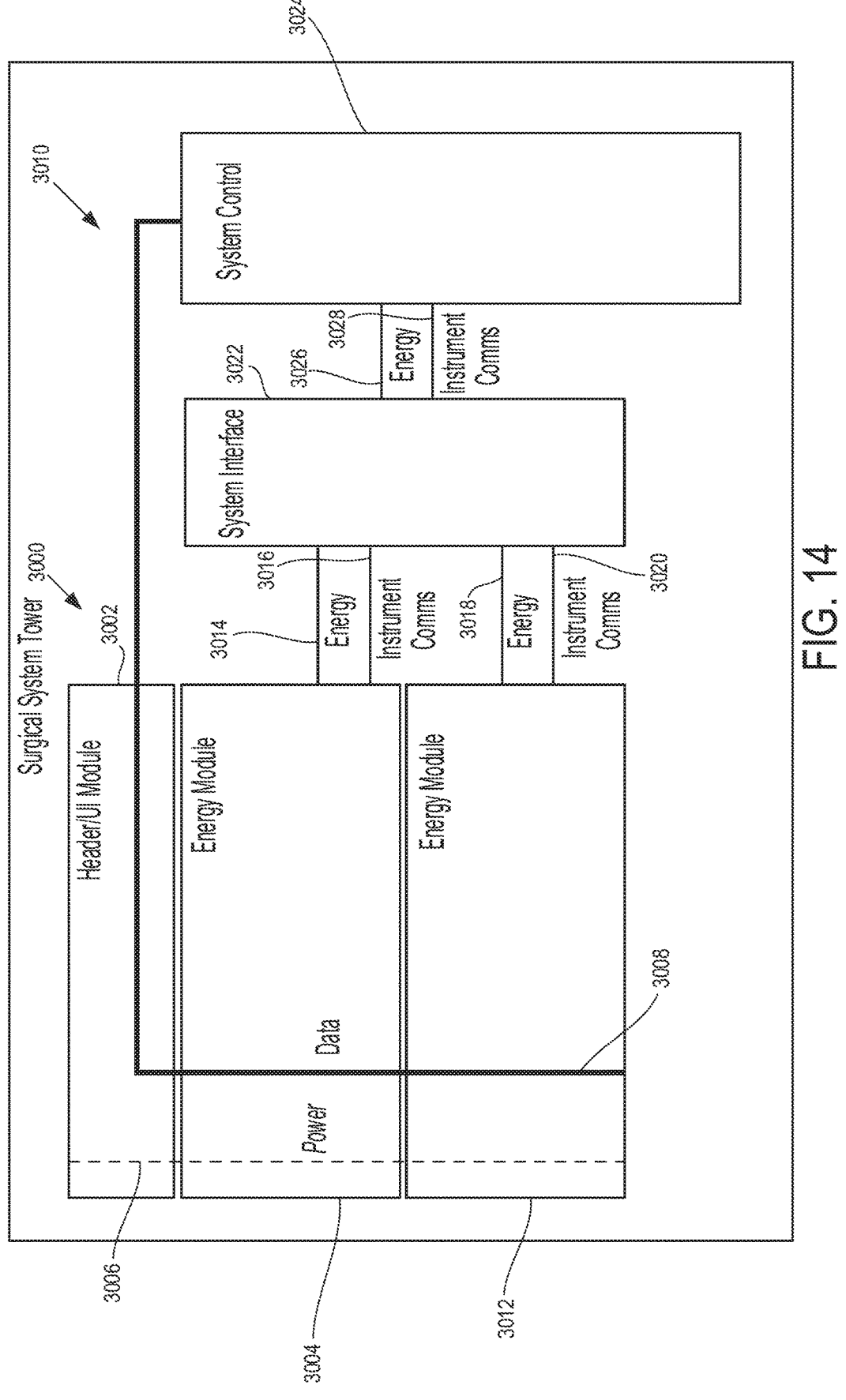
FIG. 14 is a block diagram of a hub configuration of a modular energy system integrated with a surgical control system, in accordance with at least one aspect of the present disclosure.

FIG. 13 is a block diagram of a stand-alone hub configuration of a modular energy system 3000, in accordance with at least one aspect of the present disclosure and FIG. 14 is a block diagram of a hub configuration of a modular energy system 3000 integrated with a surgical control system 3010, in accordance with at least one aspect of the present disclosure. As depicted in FIGS. 13 and 14, the modular energy system 3000 can be either utilized as stand-alone units or integrated with a surgical control system 3010 that controls and/or receives data from one or more surgical hub units. In the examples illustrated in FIGS. 13 and 14, the integrated header/UI module 3002 of the modular energy system 3000 includes a header module and a UI module integrated together as a singular module. In other aspects, the header module and the UI module can be provided as separate components that are communicatively coupled though a data bus 3008.

As illustrated in FIG. 13, an example of a stand-alone modular energy system 3000 includes an integrated header module/user interface (UI) module 3002 coupled to an energy module 3004. Power and data are transmitted between the integrated header/UI module 3002 and the energy module 3004 through a power interface 3006 and a data interface 3008. For example, the integrated header/UI module 3002 can transmit various commands to the energy module 3004 through the data interface 3008. Such commands can be based on user inputs from the UI. As a further example, power may be transmitted to the energy module 3004 through the power interface 3006.

In FIG. 14, a surgical hub configuration includes a modular energy system 3000 integrated with a control system 3010 and an interface system 3022 for managing, among other things, data and power transmission to and/or from the modular energy system 3000. The modular energy system depicted in FIG. 14 includes an integrated header module/UI module 3002, a first energy module 3004, and a second energy module 3012. In one example, a data transmission pathway is established between the system control unit 3024 of the control system 3010 and the second energy module 3012 through the first energy module 3004 and the header/

UI module 3002 through a data interface 3008. In addition, a power pathway extends between the integrated header/UI module 3002 and the second energy module 3012 through the first energy module 3004 through a power interface 3006. In other words, in one aspect, the first energy module 3004 is configured to function as a power and data interface between the second energy module 3012 and the integrated header/UI module 3002 through the power interface 3006 and the data interface 3008. This arrangement allows the modular energy system 3000 to expand by seamlessly connecting additional energy modules to energy modules 3004, 3012 that are already connected to the integrated header/UI module 3002 without the need for dedicated power and energy interfaces within the integrated header/UI module 3002.

The system control unit 3024, which may be referred to herein as a control circuit, control logic, microprocessor, microcontroller, logic, or FPGA, or various combinations thereof, is coupled to the system interface 3022 via energy interface 3026 and instrument communication interface 3028. The system interface 3022 is coupled to the first energy module 3004 via a first energy interface 3014 and a first instrument communication interface 3016. The system interface 3022 is coupled to the second energy module 3012 via a second energy interface 3018 and a second instrument communication interface 3020. As additional modules, such as additional energy modules, are stacked in the modular energy system 3000, additional energy and communications interfaces are provided between the system interface 3022 and the additional modules.

The energy modules 3004, 3012 are connectable to a hub and can be configured to generate electrosurgical energy (e.g., bipolar or monopolar), ultrasonic energy, or a combination thereof (referred to herein as an "advanced energy" module) for a variety of energy surgical instruments. Generally, the energy modules 3004, 3012 include hardware/software interfaces, an ultrasonic controller, an advanced energy RF controller, bipolar RF controller, and control algorithms executed by the controller that receives outputs from the controller and controls the operation of the various energy modules 3004, 3012 accordingly. In various aspects of the present disclosure, the controllers described herein may be implemented as a control circuit, control logic, microprocessor, microcontroller, logic, or FPGA, or various combinations thereof.

Figure 15:
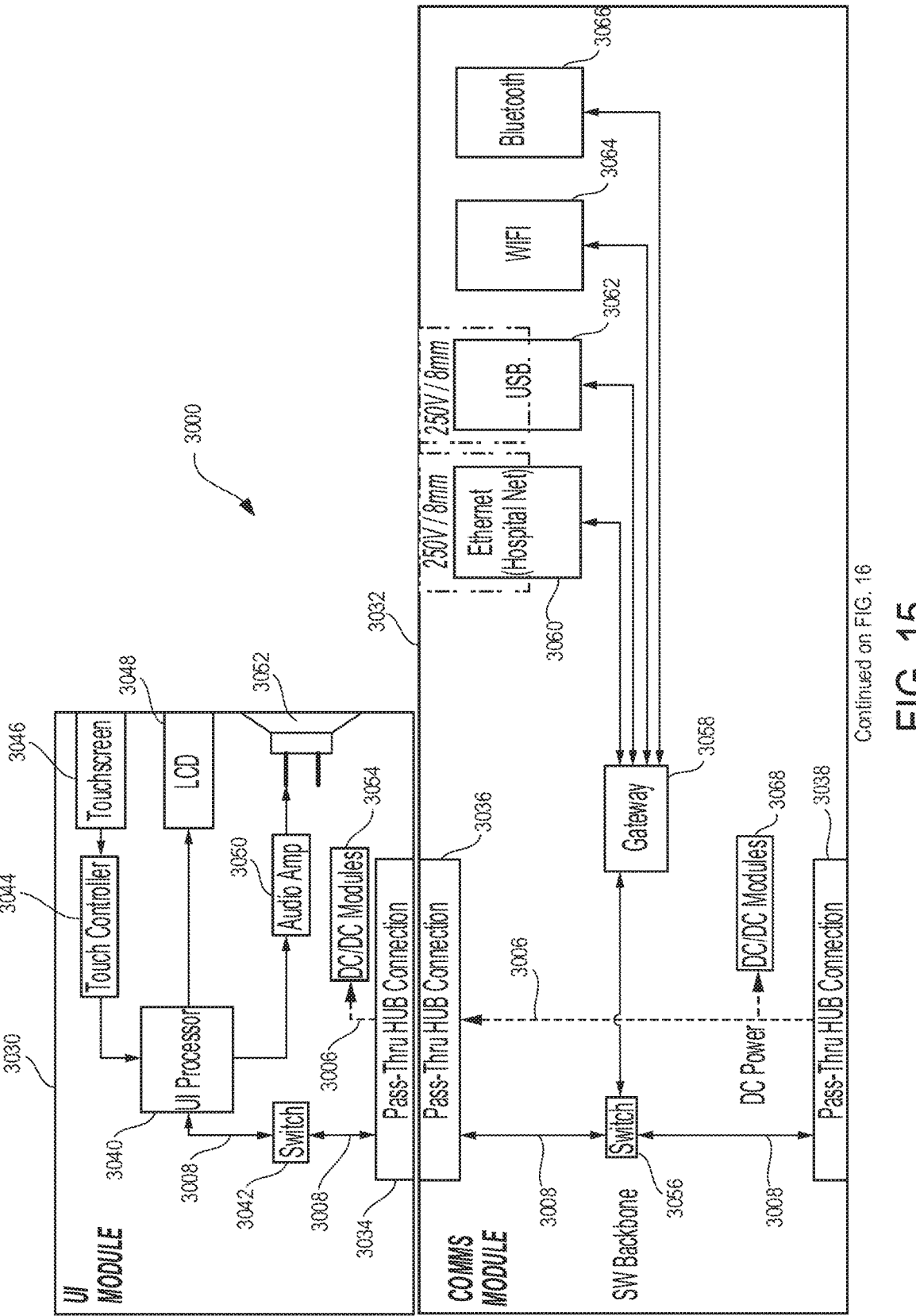
FIG. 15 is a block diagram of a user interface module coupled to a communications module of a modular energy system, in accordance with at least one aspect of the present disclosure.
Figure 16:
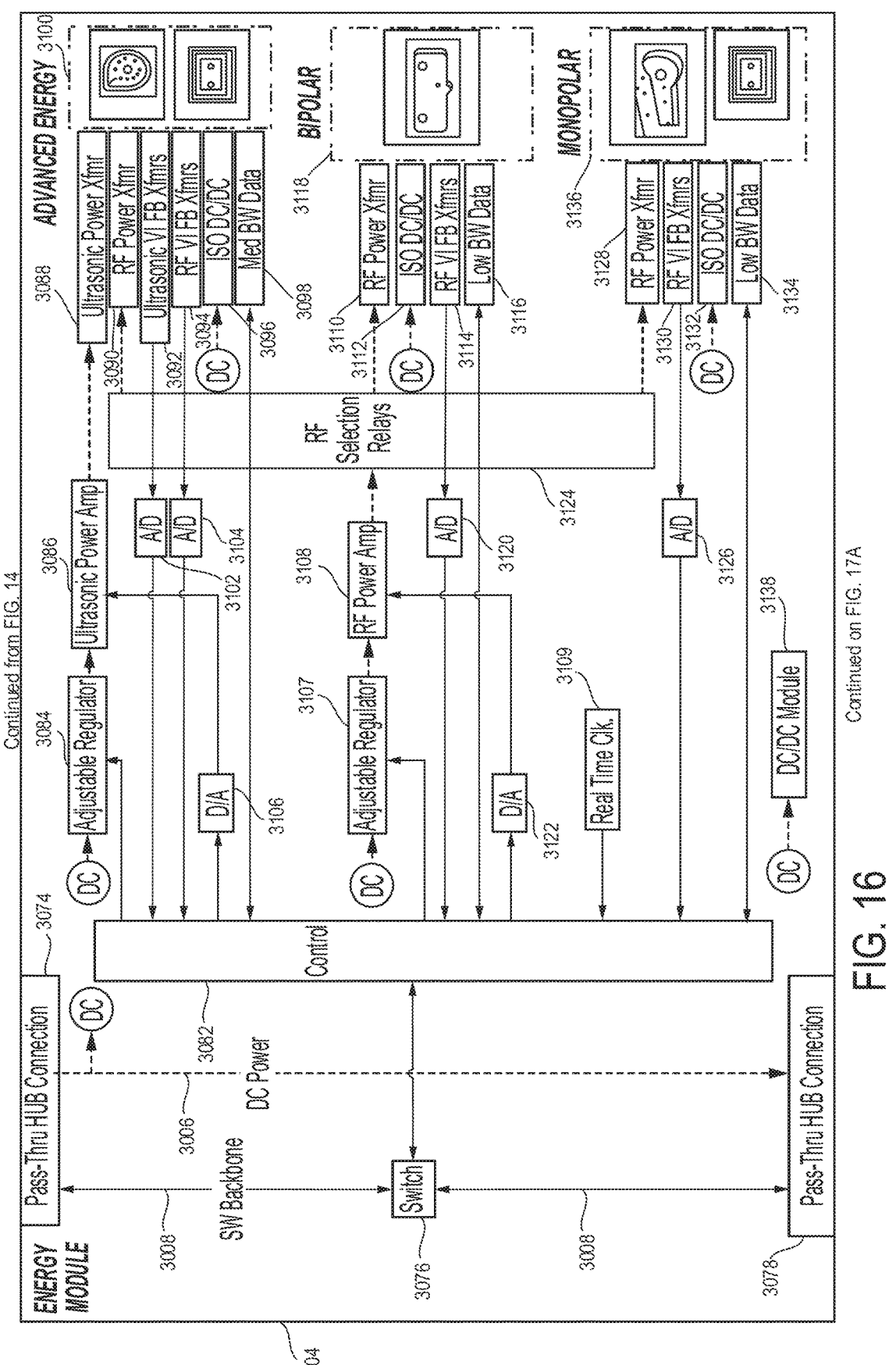
FIG. 16 is a block diagram of an energy module of a modular energy system, in accordance with at least one aspect of the present disclosure.
Figure 17A:
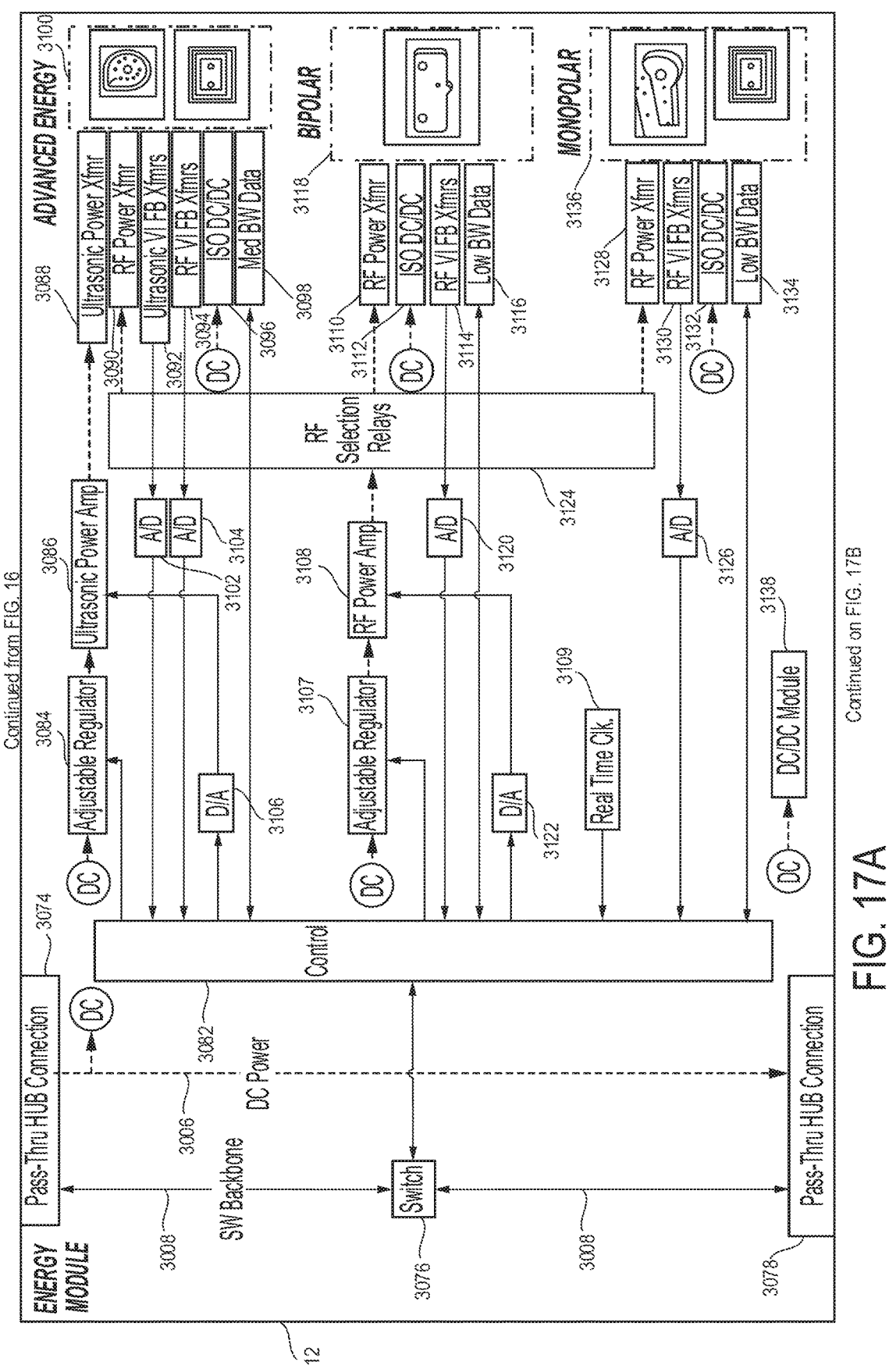
FIGS. 17A and 17B illustrate a block diagram of an energy module coupled to a header module of a modular energy system, in accordance with at least one aspect of the present disclosure.
Figure 17B:
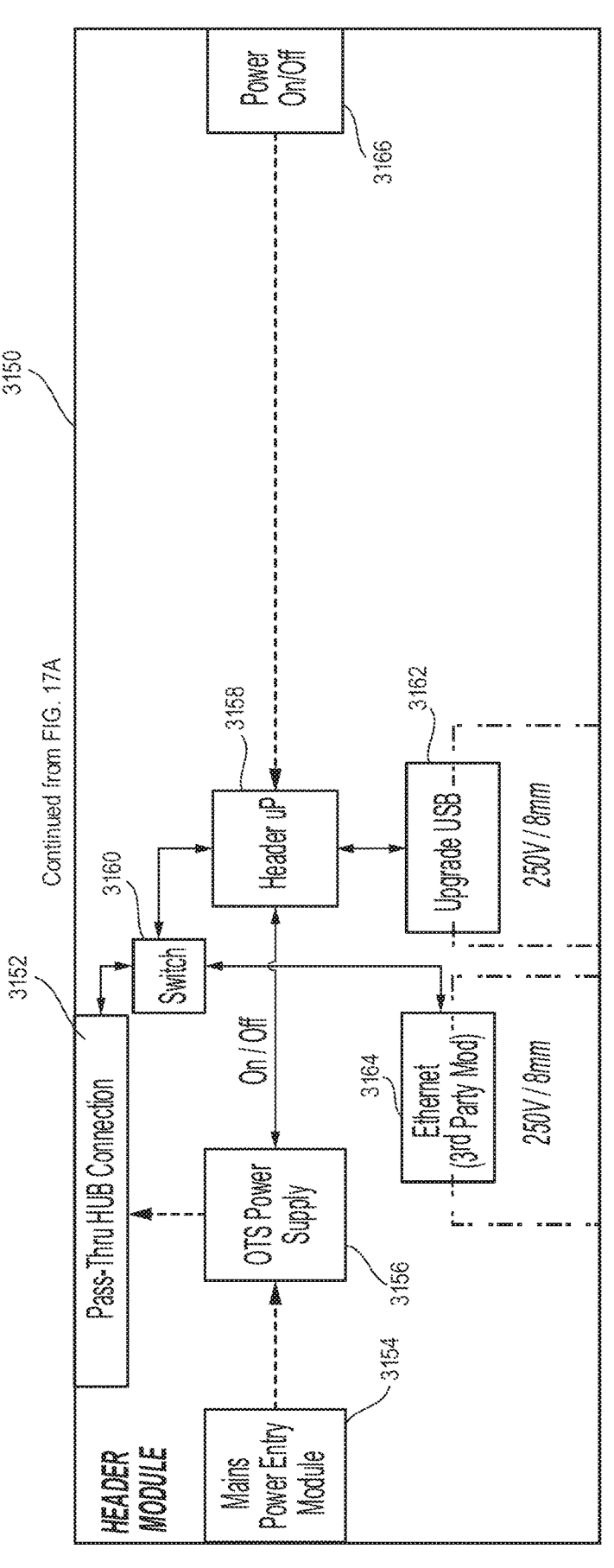

FIGS. 15-17 are block diagrams of various modular energy systems connected together to form a hub, in accordance with at least one aspect of the present disclosure. FIGS. 15-17 depict various diagrams (e.g., circuit or control diagrams) of hub modules. The modular energy system 3000 includes multiple energy modules 3004 (FIG. 16), 3012 (FIG. 17), a header module 3150 (FIG. 17), a UI module 3030 (FIG. 15), and a communications module 3032 (FIG. 15), in accordance with at least one aspect of the present disclosure. The UI module 3030 includes a touch screen 3046 displaying various relevant information and various user controls for controlling one or more parameters of the modular energy system 3000. The UI module 3030 is attached to the top header module 3150, but is separately housed so that it can be manipulated independently of the header module 3150. For example, the UI module 3030 can be picked up by a user and/or reattached to the header module 3150. Additionally, or alternatively, the UI module 3030 can be slightly moved relative to the header module 3150 to adjust its position and/or orientation. For example, the UI module 3030 can be tilted and/or rotated relative to the header module 3150.

In some aspects, the various hub modules can include light piping around the physical ports to communicate instrument status and also connect on-screen elements to corresponding instruments. Light piping is one example of an illumination technique that may be employed to alert a user to a status of a surgical instrument attached/connected to a physical port. In one aspect, illuminating a physical port with a particular light directs a user to connect a surgical instrument to the physical port. In another example, illuminating a physical port with a particular light alerts a user to an error related an existing connection with a surgical instrument.

Turning to FIG. 15, there is shown a block diagram of a user interface (UI) module 3030 coupled to a communications module 3032 via a pass-through hub connector 3034, in accordance with at least one aspect of the present disclosure. The UI module 3030 is provided as a separate component from a header module 3150 (shown in FIG. 17) and may be communicatively coupled to the header module 3150 via a communications module 3032, for example. In one aspect, the UI module 3030 can include a UI processor 3040 that is configured to represent declarative visualizations and behaviors received from other connected modules, as well as perform other centralized UI functionality, such as system configuration (e.g., language selection, module associations, etc.). The UI processor 3040 can be, for example, a processor or system on module (SOM) running a framework such as Qt, .NET WPF, Web server, or similar.

In the illustrated example, the UI module 3030 includes a touchscreen 3046, a liquid crystal display 3048 (LCD), and audio output 3052 (e.g., speaker, buzzer). The UI processor 3040 is configured to receive touchscreen inputs from a touch controller 3044 coupled between the touch screen 3046 and the UI processor 3040. The UI processor 3040 is configured to output visual information to the LCD display 3048 and to output audio information the audio output 3052 via an audio amplifier 3050. The UI processor 3040 is configured to interface to the communications module 3032 via a switch 3042 coupled to the pass-through hub connector 3034 to receive, process, and forward data from the source device to the destination device and control data communication therebetween. DC power is supplied to the UI module 3030 via DC/DC converter modules 3054. The DC power is passed through the pass-through hub connector 3034 to the communications module 3032 through the power bus 3006. Data is passed through the pass-through hub connector 3034 to the communications module 3032 through the data bus 3008. Switches 3042, 3056 receive, process, and forward data from the source device to the destination device.

Continuing with FIG. 15, the communications module 3032, as well as various surgical hubs and/or surgical systems can include a gateway 3058 that is configured to shuttle select traffic (i.e., data) between two disparate networks (e.g., an internal network and/or a hospital network) that are running different protocols. The communications module 3032 includes a first pass-through hub connector 3036 to couple the communications module 3032 to other modules. In the illustrated example, the communications module 3032 is coupled to the UI module 3030. The communications module 3032 is configured to couple to other modules (e.g., energy modules) via a second pass-through hub connector 3038 to couple the communications module 3032 to other modules via a switch 3056 disposed between the first and second pass-through hub connectors 3036, 3038 to receive, process, and forward data from the source device to the destination device and control data communication therebetween. The switch 3056 also is coupled to a gateway 3058 to communicate information between external communications ports and the UI module 3030 and other connected modules. The gateway 3058 may be coupled to various communications modules such as, for example, an Ethernet module 3060 to communicate to a hospital or other local network, a universal serial bus (USB) module 3062, a WiFi module 3064, and a Bluetooth module 3066, among others. The communications modules may be physical boards located within the communications module 3032 or may be a port to couple to remote communications boards.

Figure 18A:
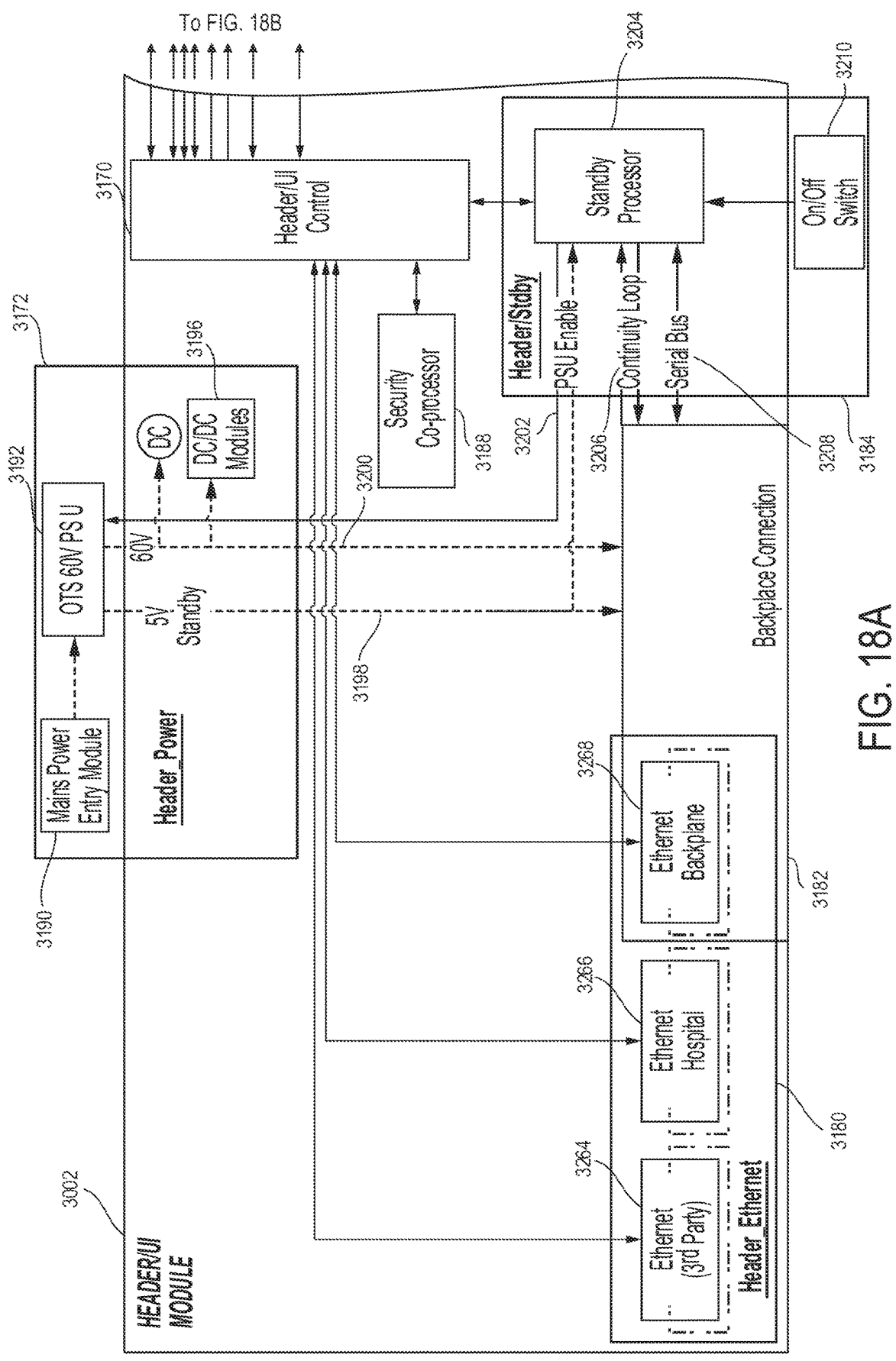
FIGS. 18A and 18B illustrate a block diagram of a header/user interface (UI) module of a modular energy system for a hub, such as the header module depicted in FIG. 15, in accordance with at least one aspect of the present disclosure.
Figure 18B:
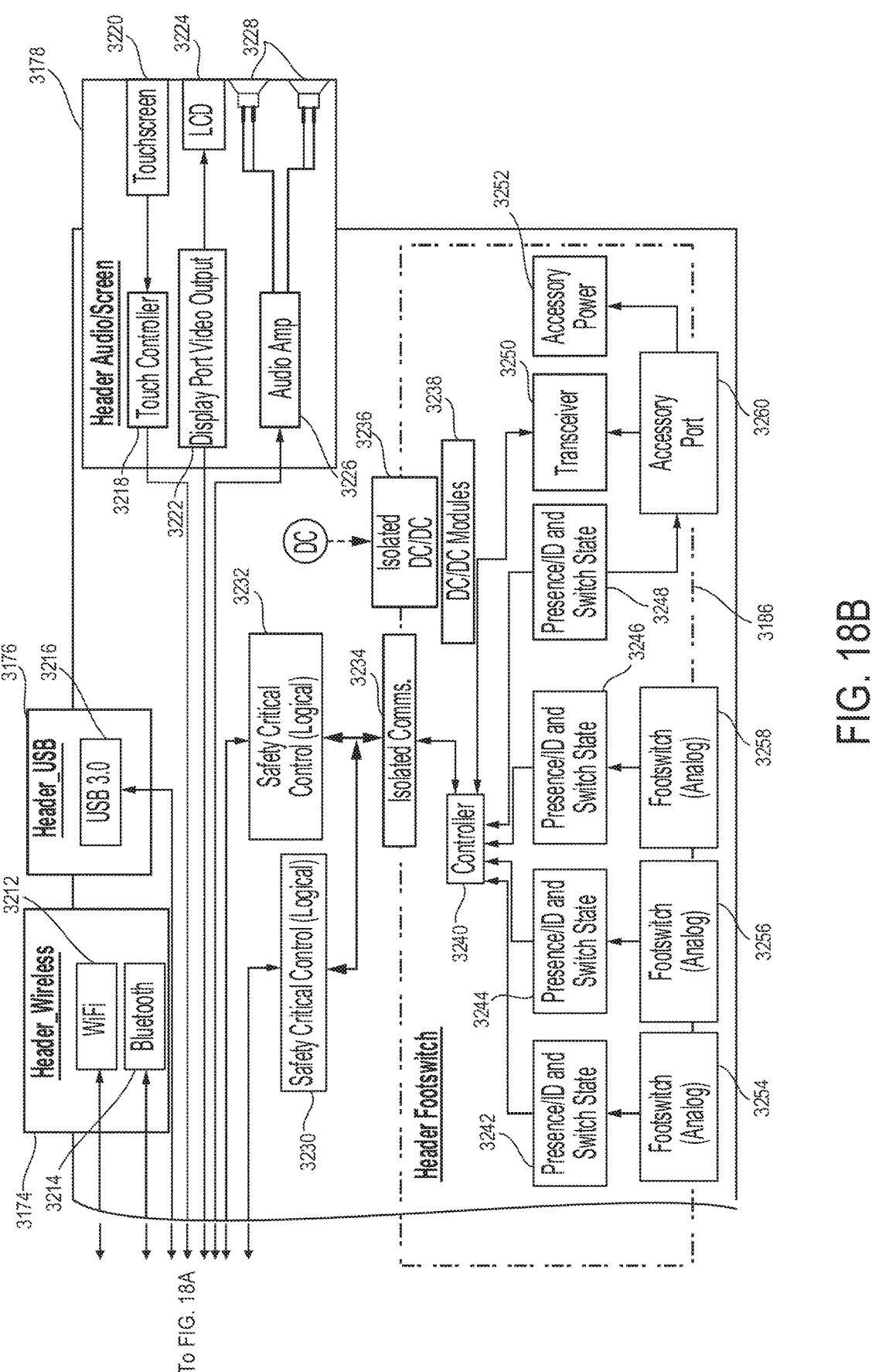

In some aspects, all of the modules (i.e., detachable hardware) are controlled by a single UI module 3030 that is disposed on or integral to a header module. FIG. 17 shows a stand alone header module 3150 to which the UI module 3030 can be attached. FIGS. 13, 14, and 18 show an integrated header/UI Module 3002. Returning now to FIG. 15, in various aspects, by consolidating all of the modules into a single, responsive UI module 3002, the system provides a simpler way to control and monitor multiple pieces of equipment at once. This approach drastically reduces footprint and complexity in an operating room (OR).

Turning to FIG. 16, there is shown a block diagram of an energy module 3004, in accordance with at least one aspect of the present disclosure. The communications module 3032 (FIG. 15) is coupled to the energy module 3004 via the second pass-through hub connector 3038 of the communications module 3032 and a first pass-through hub connector 3074 of the energy module 3004. The energy module 3004 may be coupled to other modules, such as a second energy module 3012 shown in FIG. 17, via a second pass-through hub connector 3078. Turning back to FIG. 16, a switch 3076 disposed between the first and second pass-through hub connectors 3074, 3078 receives, processes, and forwards data from the source device to the destination device and controls data communication therebetween. Data is received and transmitted through the data bus 3008. The energy module 3032 includes a controller 3082 to control various communications and processing functions of the energy module 3004.

DC power is received and transmitted by the energy module 3004 through the power bus 3006. The power bus 3006 is coupled to DC/DC converter modules 3138 to supply power to adjustable regulators 3084, 3107 and isolated DC/DC converter ports 3096, 3112, 3132.

In one aspect, the energy module 3004 can include an ultrasonic wideband amplifier 3086, which in one aspect may be a linear class H amplifier that is capable of generating arbitrary waveforms and drive harmonic transducers at low total harmonic distortion (THD) levels. The ultrasonic wideband amplifier 3086 is fed by a buck adjustable regulator 3084 to maximize efficiency and controlled by the controller 3082, which may be implemented as a digital signal processor (DSP) via a direct digital synthesizer (DDS), for example. The DDS can either be embedded in the DSP or implemented in the field-programmable gate array (FPGA), for example. The controller 3082 controls the ultrasonic wideband amplifier 3086 via a digital-to-analog converter 3106 (DAC). The output of the ultrasonic wideband amplifier 3086 is fed to an ultrasonic power transformer 3088, which is coupled to an ultrasonic energy output portion of an advanced energy receptacle 3100. Ultrasonic voltage (V) and current (I) feedback (FB) signals, which may be employed to compute ultrasonic impedance, are fed back to the controller 3082 via an ultrasonic VI FB transformer 3092 through an input portion of the advanced energy receptacle 3100. The ultrasonic voltage and current feedback signals are routed back to the controller 3082 through an analog-to-digital converter 3102 (A/D). Also coupled to the controller 3082 through the advanced energy receptacle 3100 is the isolated DC/DC converter port 3096, which receives DC power from the power bus 3006, and a medium bandwidth data port 3098.

In one aspect, the energy module 3004 can include a wideband RF power amplifier 3108, which in one aspect may be a linear class H amplifier that is capable of generating arbitrary waveforms and drive RF loads at a range of output frequencies. The wideband RF power amplifier 3108 is fed by an adjustable buck regulator 3107 to maximize efficiency and controlled by the controller 3082, which may be implemented as DSP via a DDS. The DDS can either be embedded in the DSP or implemented in the FPGA, for example. The controller 3082 controls the wideband RF amplifier 3086 via a DAC 3122. The output of the wideband RF power amplifier 3108 can be fed through RF selection relays 3124. The RF selection relays 3124 are configured to receive and selectively transmit the output signal of the wideband RF power amplifier 3108 to various other components of the energy module 3004. In one aspect, the output signal of the wideband RF power amplifier 3108 can be fed through RF selection relays 3124 to an RF power transformer 3110, which is coupled to an RF output portion of a bipolar RF energy receptacle 3118. Bipolar RF voltage (V) and current (I) feedback (FB) signals, which may be employed to compute RF impedance, are fed back to the controller 3082 via an RF VI FB transformer 3114 through an input portion of the bipolar RF energy receptacle 3118. The RF voltage and current feedback signals are routed back to the controller 3082 through an A/D 3120. Also coupled to the controller 3082 through the bipolar RF energy receptacle 3118 is the isolated DC/DC converter port 3112, which receives DC power from the power bus 3006, and a low bandwidth data port 3116.

As described above, in one aspect, the energy module 3004 can include RF selection relays 3124 driven by the controller 3082 (e.g., FPGA) at rated coil current for actuation and can also be set to a lower hold-current via pulse-width modulation (PWM) to limit steady-state power dissipation. Switching of the RF selection relays 3124 is achieved with force guided (safety) relays and the status of the contact state is sensed by the controller 3082 as a mitigation for any single fault conditions. In one aspect, the RF selection relays 3124 are configured to be in a first state, where an output RF signal received from an RF source, such as the wideband RF power amplifier 3108, is transmitted to a first component of the energy module 3004, such as the RF power transformer 3110 of the bipolar energy receptacle 3118. In a second aspect, the RF selection relays 3124 are configured to be in a second state, where an output RF signal received from an RF source, such as the wideband RF power amplifier 3108, is transmitted to a second component, such as an RF power transformer 3128 of a monopolar energy receptacle 3136, described in more detail below. In a general aspect, the RF selection relays 3124 are configured to be driven by the controller 3082 to switch between a plurality of states, such as the first state and the second state, to transmit the output RF signal received from the RF power amplifier 3108 between different energy receptacles of the energy module 3004.

As described above, the output of the wideband RF power amplifier 3108 can also fed through the RF selection relays 3124 to the wideband RF power transformer 3128 of the RF monopolar receptacle 3136. Monopolar RF voltage (V) and current (I) feedback (FB) signals, which may be employed to compute RF impedance, are fed back to the controller 3082 via an RF VI FB transformer 3130 through an input portion of the monopolar RF energy receptacle 3136. The RF voltage and current feedback signals are routed back to the controller 3082 through an A/D 3126. Also coupled to the controller 3082 through the monopolar RF energy receptacle 3136 is the isolated DC/DC converter port 3132, which receives DC power from the power bus 3006, and a low bandwidth data port 3134.

The output of the wideband RF power amplifier 3108 can also fed through the RF selection relays 3124 to the wideband RF power transformer 3090 of the advanced energy receptacle 3100. RF voltage (V) and current (I) feedback (FB) signals, which may be employed to compute RF impedance, are fed back to the controller 3082 via an RF VI FB transformer 3094 through an input portion of the advanced energy receptacle 3100. The RF voltage and current feedback signals are routed back to the controller 3082 through an A/D 3104.

FIG. 17 is a block diagram of a second energy module 3012 coupled to a header module 3150, in accordance with at least one aspect of the present disclosure. The first energy module 3004 shown in FIG. 16 is coupled to the second energy module 3012 shown in FIG. 17 by coupling the second pass-through hub connector 3078 of the first energy module 3004 to a first pass-through hub connector 3074 of the second energy module 3012. In one aspect, the second energy module 3012 can a similar energy module to the first energy module 3004, as is illustrated in FIG. 17. In another aspect, the second energy module 2012 can be a different energy module compared to the first energy module, such as an energy module illustrated in FIG. 19, described in more detail. The addition of the second energy module 3012 to the first energy module 3004 adds functionality to the modular energy system 3000.

The second energy module 3012 is coupled to the header module 3150 by connecting the pass-through hub connector 3078 to the pass-through hub connector 3152 of the header module 3150. In one aspect, the header module 3150 can include a header processor 3158 that is configured to manage a power button function 3166, software upgrades through the upgrade USB module 3162, system time management, and gateway to external networks (i.e., hospital or the cloud) via an Ethernet module 3164 that may be running different protocols. Data is received by the header module 3150 through the pass-through hub connector 3152. The header processor 3158 also is coupled to a switch 3160 to receive, process, and forward data from the source device to the destination device and control data communication therebetween. The header processor 3158 also is coupled to an OTS power supply 3156 coupled to a mains power entry module 3154.

FIG. 18 is a block diagram of a header/user interface (UI) module 3002 for a hub, such as the header module depicted in FIG. 15, in accordance with at least one aspect of the present disclosure. The header/UI module 3002 includes a header power module 3172, a header wireless module 3174, a header USB module 3176, a header audio/screen module 3178, a header network module 3180 (e.g., Ethernet), a backplane connector 3182, a header standby processor module 3184, and a header footswitch module 3186. These functional modules interact to provide the header/UI 3002 functionality. A header/UI controller 3170 controls each of the functional modules and the communication therebetween including safety critical control logic modules 3230, 3232 coupled between the header/UI controller 3170 and an isolated communications module 3234 coupled to the header footswitch module 3186. A security co-processor 3188 is coupled to the header/UI controller 3170.

The header power module 3172 includes a mains power entry module 3190 coupled to an OTS power supply unit 3192 (PSU). Low voltage direct current (e.g., 5V) standby power is supplied to the header/UI module 3002 and other modules through a low voltage power bus 3198 from the OTS PSU 3192. High voltage direct current (e.g., 60V) is supplied to the header/UI module 3002 through a high voltage bus 3200 from the OTS PSU 3192. The high voltage DC supplies DC/DC converter modules 3196 as well as isolated DC/DC converter modules 3236. A standby processor 3204 of the header/standby module 3184 provides a PSU/enable signal 3202 to the OTS PSU 3192.

The header wireless module 3174 includes a WiFi module 3212 and a Bluetooth module 3214. Both the WiFi module 3212 and the Bluetooth module 3214 are coupled to the header/UI controller 3170. The Bluetooth module 3214 is used to connect devices without using cables and the Wi-Fi module 3212 provides high-speed access to networks such as the Internet and can be employed to create a wireless network that can link multiple devices such as, for examples, multiple energy modules or other modules and surgical instruments, among other devices located in the operating room. Bluetooth is a wireless technology standard that is used to exchange data over short distances, such as, less than 30 feet.

The header USB module 3176 includes a USB port 3216 coupled to the header/UI controller 3170. The USB module 3176 provides a standard cable connection interface for modules and other electronics devices over short-distance digital data communications. The USB module 3176 allows modules comprising USB devices to be connected to each other with and transfer digital data over USB cables.

The header audio/screen module 3178 includes a touch-screen 3220 coupled to a touch controller 3218. The touch controller 3218 is coupled to the header/UI controller 3170 to read inputs from the touchscreen 3220. The header/UI controller 3170 drives an LCD display 3224 through a display/port video output signal 3222. The header/UI controller 3170 is coupled to an audio amplifier 3226 to drive one or more speakers 3228.

In one aspect, the header/UI module 3002 provides a touchscreen 3220 user interface configured to control modules connected to one control or header module 3002 in a modular energy system 3000. The touchscreen 3220 can be used to maintain a single point of access for the user to adjust all modules connected within the modular energy system 3000. Additional hardware modules (e.g., a smoke evacuation module) can appear at the bottom of the user interface LCD display 3224 when they become connected to the header/UI module 3002, and can disappear from the user interface LCD display 3224 when they are disconnected from the header/UI module 3002.

Further, the user touchscreen 3220 can provide access to the settings of modules attached to the modular energy system 3000. Further, the user interface LCD display 3224 arrangement can be configured to change according to the number and types of modules that are connected to the header/UI module 3002. For example, a first user interface can be displayed on the LCD display 3224 for a first application where one energy module and one smoke evacuation module are connected to the header/UI module 3002, and a second user interface can be displayed on the LCD display 3224 for a second application where two energy modules are connected to the header/UI module 3002.

Further, the user interface can alter its display on the LCD display 3224 as modules are connected and disconnected from the modular energy system 3000.

In one aspect, the header/UI module 3002 provides a user interface LCD display 3224 configured to display on the LCD display coloring corresponds to the port lighting. In one aspect, the coloring of the instrument panel and the LED light around its corresponding port will be the same or otherwise correspond with each other. Each color can, for example, convey a unique meaning. This way, the user will be able to quickly assess which instrument the indication is referring to and the nature of the indication. Further, indications regarding an instrument can be represented by the changing of color of the LED light lined around its corresponding port and the coloring of its module. Still further, the message on screen and hardware/software port alignment can also serve to convey that an action must be taken on the hardware, not on the interface. In various aspects, all other instruments can be used while alerts are occurring on other instruments. This allows the user to be able to quickly assess which instrument the indication is referring to and the nature of the indication.

In one aspect, the header/UI module 3002 provides a user interface screen configured to display on the LCD display 3224 to present procedure options to a user. In one aspect, the user interface can be configured to present the user with a series of options (which can be arranged, e.g., from broad to specific). After each selection is made, the modular energy system 3000 presents the next level until all selections are complete. These settings could be managed locally and transferred via a secondary means (such as a USB thumb drive). Alternatively, the settings could be managed via a portal and automatically distributed to all connected systems in the hospital.

The procedure options can include, for example, a list of factory preset options categorized by specialty, procedure, and type of procedure. Upon completing a user selection, the header module can be configured to set any connected instruments to factory-preset settings for that specific procedure. The procedure options can also include, for example, a list of surgeons, then subsequently, the specialty, procedure, and type. Once a user completes a selection, the system may suggest the surgeon's preferred instruments and set those instrument's settings according to the surgeon's preference (i.e., a profile associated with each surgeon storing the surgeon's preferences).

In one aspect, the header/UI module 3002 provides a user interface screen configured to display on the LCD display 3224 critical instrument settings. In one aspect, each instrument panel displayed on the LCD display 3224 of the user interface corresponds, in placement and content, to the instruments plugged into the modular energy system 3000. When a user taps on a panel, it can expand to reveal additional settings and options for that specific instrument and the rest of the screen can, for example, darken or otherwise be de-emphasized.

In one aspect, the header/UI module 3002 provides an instrument settings panel of the user interface configured to comprise/display controls that are unique to an instrument and allow the user to increase or decrease the intensity of its output, toggle certain functions, pair it with system accessories like a footswitch connected to header footswitch module 3186, access advanced instrument settings, and find additional information about the instrument. In one aspect, the user can tap/select an "Advanced Settings" control to expand the advanced settings drawer displayed on the user interface LCD display 3224. In one aspect, the user can then tap/select an icon at the top right-hand corner of the instrument settings panel or tap anywhere outside of the panel and the panel will scale back down to its original state. In these aspects, the user interface is configured to display on the LCD display 3224 only the most critical instrument settings, such as power level and power mode, on the ready/home screen for each instrument panel. This is to maximize the size and readability of the system from a distance. In some aspects, the panels and the settings within can be scaled proportionally to the number of instruments connected to the system to further improve readability. As more instruments are connected, the panels scale to accommodate a greater amount of information.

The header network module 3180 includes a plurality of network interfaces 3264, 3266, 3268 (e.g., Ethernet) to network the header/UI module 3002 to other modules of the modular energy system 3000. In the illustrated example, one network interface 3264 may be a 3rd party network interface, another network interface 3266 may be a hospital network interface, and yet another network interface 3268 may be located on the backplane network interface connector 3182.

The header standby processor module 3184 includes a standby processor 3204 coupled to an On/Off switch 3210. The standby processor 3204 conducts an electrical continuity test by checking to see if electrical current flows in a continuity loop 3206. The continuity test is performed by placing a small voltage across the continuity loop 3206. A serial bus 3208 couples the standby processor 3204 to the backplane connector 3182.

The header footswitch module 3186 includes a controller 3240 coupled to a plurality of analog footswitch ports 3254, 3256, 3258 through a plurality of corresponding presence/ID and switch state modules 3242, 3244, 3246, respectively. The controller 3240 also is coupled to an accessory port 3260 via a presence/ID and switch state module 3248 and a transceiver module 3250. The accessory port 3260 is powered by an accessory power module 3252. The controller 3240 is coupled to header/UI controller 3170 via an isolated communication module 3234 and first and second safety critical control modules 3230, 3232. The header footswitch module 3186 also includes DC/DC converter modules 3238.

In one aspect, the header/UI module 3002 provides a user interface screen configured to display on the LCD display 3224 for controlling a footswitch connected to any one of the analog footswitch ports 3254, 3256, 3258. In some aspects, when the user plugs in a non hand-activated instrument into any one of the analog footswitch ports 3254, 3256, 3258, the instrument panel appears with a warning icon next to the footswitch icon. The instrument settings can be, for example, greyed out, as the instrument cannot be activated without a footswitch.

When the user plugs in a footswitch into any one of the analog footswitch ports 3254, 3256, 3258, a pop-up appears indicating that a footswitch has been assigned to that instrument. The footswitch icon indicates that a footswitch has been plugged in and assigned to the instrument. The user can then tap/select on that icon to assign, reassign, unassign, or otherwise change the settings associated with that footswitch. In these aspects, the system is configured to automatically assign footswitches to non hand-activated instruments using logic, which can further assign single or double-pedal footswitches to the appropriate instrument. If the user wants to assign/reassign footswitches manually there are two flows that can be utilized.

In one aspect, the header/UI module 3002 provides a global footswitch button. Once the user taps on the global footswitch icon (located in the upper right of the user interface LCD display 3224), the footswitch assignment overlay appears and the contents in the instrument modules dim. A (e.g., photo-realistic) representation of each attached footswitch (dual or single-pedal) appears on the bottom if unassigned to an instrument or on the corresponding instrument panel. Accordingly, the user can drag and drop these illustrations into, and out of, the boxed icons in the footswitch assignment overlay to assign, unassign, and reassign footswitches to their respective instruments.

In one aspect, the header/UI module 3002 provides a user interface screen displayed on the LCD display 3224 indicating footswitch auto-assignment, in accordance with at least one aspect of the present disclosure. As discussed above, the modular energy system 3000 can be configured to auto-assign a footswitch to an instrument that does not have hand activation. In some aspects, the header/UI module 3002 can be configured to correlate the colors displayed on the user interface LCD display 3224 to the lights on the modules themselves as means of tracking physical ports with user interface elements.

In one aspect, the header/UI module 3002 may be configured to depict various applications of the user interface with differing number of modules connected to the modular energy system 3000. In various aspects, the overall layout or proportion of the user interface elements displayed on the LCD display 3224 can be based on the number and type of instruments plugged into the header/UI module 3002. These scalable graphics can provide the means to utilize more of the screen for better visualization.

In one aspect, the header/UI module 3002 may be configured to depict a user interface screen on the LCD display 3224 to indicate which ports of the modules connected to the modular energy system 3000 are active. In some aspects, the header/UI module 3002 can be configured to illustrate active versus inactive ports by highlighting active ports and dimming inactive ports. In one aspect, ports can be represented with color when active (e.g., monopolar tissue cut with yellow, monopolar tissue coagulation with blue, bipolar tissue cut with blue, advanced energy tissue cut with warm white, and so on). Further, the displayed color will match the color of the light piping around the ports. The coloring can further indicate that the user cannot change settings of other instruments while an instrument is active. As another example, the header/UI module 3002 can be configured to depict the bipolar, monopolar, and ultrasonic ports of a first energy module as active and the monopolar ports of a second energy module as likewise active.

In one aspect, the header/UI module 3002 can be configured to depict a user interface screen on the LCD display 3224 to display a global settings menu. In one aspect, the header/UI module 3002 can be configured to display a menu on the LCD display 3224 to control global settings across any modules connected to the modular energy system 3000. The global settings menu can be, for example, always displayed in a consistent location (e.g., always available in upper right hand corner of main screen).

In one aspect, the header/UI module 3002 can be configured to depict a user interface screen on the LCD display 3224 configured to prevent changing of settings while a surgical instrument is in use. In one example, the header/UI module 3002 can be configured to prevent settings from being changed via a displayed menu when a connected instrument is active. The user interface screen can include, for example, an area (e.g., the upper left hand corner) that is reserved for indicating instrument activation while a settings menu is open. In one aspect, a user has opened the bipolar settings while monopolar coagulation is active. In one aspect, the settings menu could then be used once the activation is complete. In one aspect, the header/UI module 3002 can be is configured to never overlay any menus or other information over the dedicated area for indicating critical instrument information in order to maintain display of critical information.

In one aspect, the header/UI module 3002 can be configured to depict a user interface screen on the LCD display 3224 configured to display instrument errors. In one aspect, instrument error warnings may be displayed on the instrument panel itself, allowing user to continue to use other instruments while a nurse troubleshoots the error. This allows users to continue the surgery without the need to stop the surgery to debug the instrument.

In one aspect, the header/UI module 3002 can be configured to depict a user interface screen on the LCD display 3224 to display different modes or settings available for various instruments. In various aspects, the header/UI module 3002 can be configured to display settings menus that are appropriate for the type or application of surgical instrument (s) connected to the stack/hub. Each settings menu can provide options for different power levels, energy delivery profiles, and so on that are appropriate for the particular instrument type. In one aspect, the header/UI module 3002 can be configured to display different modes available for bipolar, monopolar cut, and monopolar coagulation applications.

In one aspect, the header/UI module 3002 can be configured to depict a user interface screen on the LCD display 3224 to display pre-selected settings. In one aspect, the header/UI module 3002 can be configured to receive selections for the instrument/device settings before plugging in instruments so that the modular energy system 3000 is ready before the patient enters the operating room. In one aspect, the user can simply click a port and then change the settings for that port. In the depicted aspect, the selected port appears as faded to indicate settings are set, but no instrument is plugged into that port.

Figure 19:
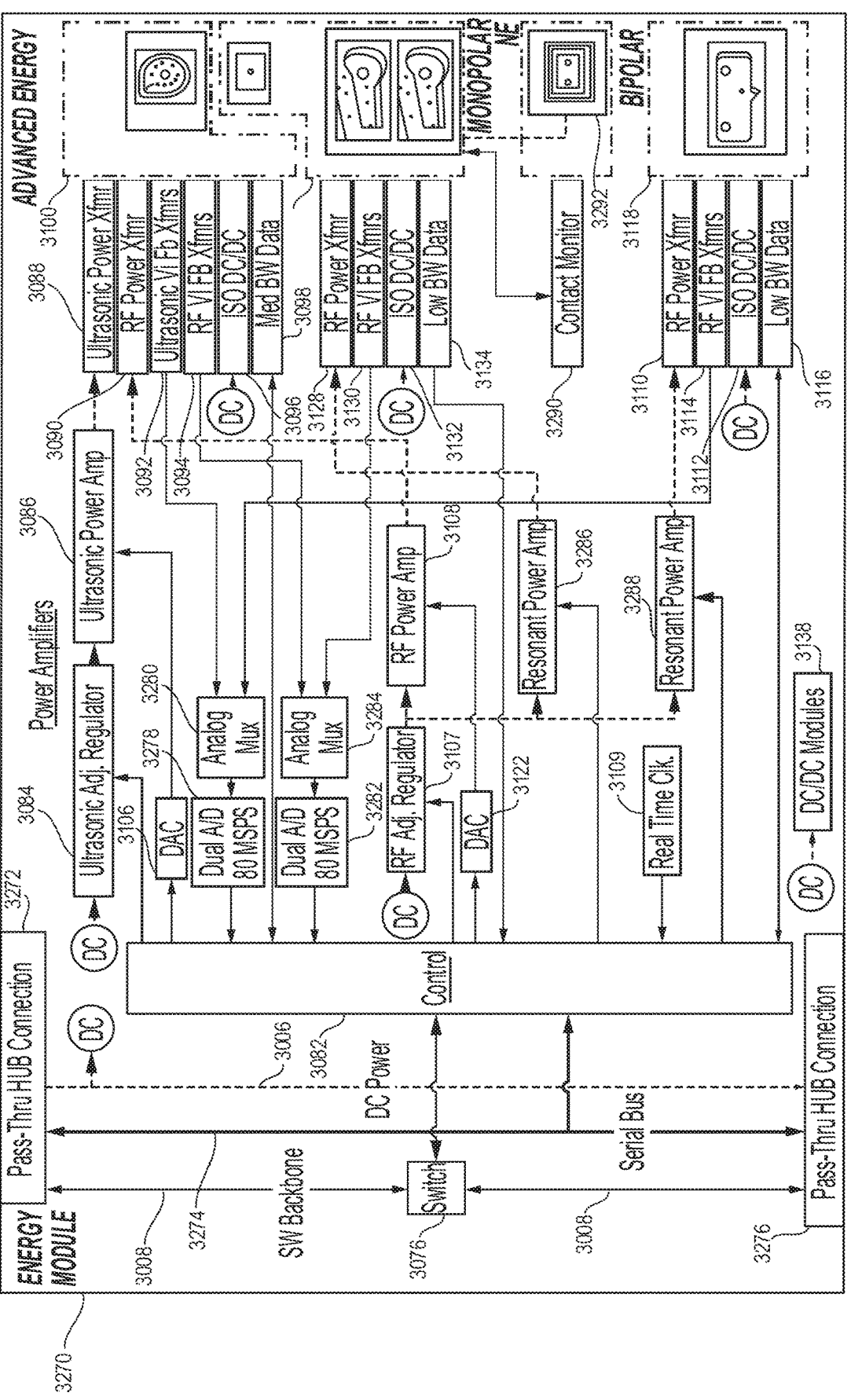
FIG. 19 is a block diagram of an energy module for a hub, such as the energy module depicted in FIGS. 13-18B, in accordance with at least one aspect of the present disclosure.

FIG. 19 is a block diagram of an energy module 3270 for a hub, such as the energy module depicted in FIGS. 13, 14, 16, and 17, in accordance with at least one aspect of the present disclosure. The energy module 3270 is configured to couple to a header module, header/UI module, and other energy modules via the first and second pass-through hub connectors 3272, 3276. A switch 3076 disposed between the first and second pass-through hub connectors 3272, 3276 receives, processes, and forwards data from the source device to the destination device and controls data communication therebetween. Data is received and transmitted through the data bus 3008. The energy module 3270 includes a controller 3082 to control various communications and processing functions of the energy module 3270.

DC power is received and transmitted by the energy module 3270 through the power bus 3006. The power bus 3006 is coupled to the DC/DC converter modules 3138 to supply power to adjustable regulators 3084, 3107 and isolated DC/DC converter ports 3096, 3112, 3132.

In one aspect, the energy module 3270 can include an ultrasonic wideband amplifier 3086, which in one aspect may be a linear class H amplifier that is capable of generating arbitrary waveforms and drive harmonic transducers at low total harmonic distortion (THD) levels. The ultrasonic wideband amplifier 3086 is fed by a buck adjustable regulator 3084 to maximize efficiency and controlled by the controller 3082, which may be implemented as a digital signal processor (DSP) via a direct digital synthesizer (DDS), for example. The DDS can either be embedded in the DSP or implemented in the field-programmable gate array (FPGA), for example. The controller 3082 controls the ultrasonic wideband amplifier 3086 via a digital-to-analog converter 3106 (DAC). The output of the ultrasonic wideband amplifier 3086 is fed to an ultrasonic power transformer 3088, which is coupled to an ultrasonic energy output portion of the advanced energy receptacle 3100. Ultrasonic voltage (V) and current (I) feedback (FB) signals, which may be employed to compute ultrasonic impedance, are fed back to the controller 3082 via an ultrasonic VI FB transformer 3092 through an input portion of the advanced energy receptacle 3100. The ultrasonic voltage and current feedback signals are routed back to the controller 3082 through an analog multiplexer 3280 and a dual analog-to-digital converter 3278 (A/D). In one aspect, the dual A/D 3278 has a sampling rate of 80 MSPS. Also coupled to the controller 3082 through the advanced energy receptacle 3100 is the isolated DC/DC converter port 3096, which receives DC power from the power bus 3006, and a medium bandwidth data port 3098.

In one aspect, the energy module 3270 can include a plurality of wideband RF power amplifiers 3108, 3286, 3288, among others, which in one aspect, each of the wideband RF power amplifiers 3108, 3286, 3288 may be linear class H amplifiers capable of generating arbitrary waveforms and drive RF loads at a range of output frequencies. Each of the wideband RF power amplifiers 3108, 3286, 3288 are fed by an adjustable buck regulator 3107 to maximize efficiency and controlled by the controller 3082, which may be implemented as DSP via a DDS. The DDS can either be embedded in the DSP or implemented in the FPGA, for example. The controller 3082 controls the first wideband RF power amplifier 3108 via a DAC 3122.

Unlike the energy modules 3004, 3012 shown and described in FIGS. 16 and 17, the energy module 3270 does not include RF selection relays configured to receive an RF output signal from the adjustable buck regulator 3107. In addition, unlike the energy modules 3004, 3012 shown and described in FIGS. 16 and 17, the energy module 3270 includes a plurality of wideband RF power amplifiers 3108, 3286, 3288 instead of a single RF power amplifier. In one aspect, the adjustable buck regulator 3107 can switch between a plurality of states, in which the adjustable buck regulator 3107 outputs an output RF signal to one of the plurality of wideband RF power amplifiers 3108, 3286, 3288 connected thereto. The controller 3082 is configured to switch the adjustable buck regulator 3107 between the plurality of states. In a first state, the controller drives the adjustable buck regulator 3107 to output an RF energy signal to the first wideband RF power amplifier 3108. In a second state, the controller drives the adjustable buck regulator 3107 to output an RF energy signal to the second wideband RF power amplifier 3286. In a third state, the controller drives the adjustable buck regulator 3107 to output an RF energy signal to the third wideband RF power amplifier 3288.

The output of the first wideband RF power amplifier 3108 can be fed to an RF power transformer 3090, which is coupled to an RF output portion of an advanced energy receptacle 3100. RF voltage (V) and current (I) feedback (FB) signals, which may be employed to compute RF impedance, are fed back to the controller 3082 via RF VI FB transformers 3094 through an input portion of the advanced energy receptacle 3100. The RF voltage and current feedback signals are routed back to the controller 3082 through the RF VI FB transformers 3094, which are coupled to an analog multiplexer 3284 and a dual A/D 3282 coupled to the controller 3082. In one aspect, the dual A/D 3282 has a sampling rate of 80 MSPS.

The output of the second RF wideband power amplifier 3286 is fed through an RF power transformer 3128 of the RF monopolar receptacle 3136. Monopolar RF voltage (V) and current (I) feedback (FB) signals, which may be employed to compute RF impedance, are fed back to the controller 3082 via RF VI FB transformers 3130 through an input portion of the monopolar RF energy receptacle 3136. The RF voltage and current feedback signals are routed back to the controller 3082 through the analog multiplexer 3284 and the dual A/D 3282. Also coupled to the controller 3082 through the monopolar RF energy receptacle 3136 is the isolated DC/DC converter port 3132, which receives DC power from the power bus 3006, and a low bandwidth data port 3134.

The output of the third RF wideband power amplifier 3288 is fed through an RF power transformer 3110 of a bipolar RF receptacle 3118. Bipolar RF voltage (V) and current (I) feedback (FB) signals, which may be employed to compute RF impedance, are fed back to the controller 3082 via RF VI FB transformers 3114 through an input portion of the bipolar RF energy receptacle 3118. The RF voltage and current feedback signals are routed back to the controller 3082 through the analog multiplexer 3280 and the dual A/D 3278. Also coupled to the controller 3082 through the bipolar RF energy receptacle 3118 is the isolated DC/DC converter port 3112, which receives DC power from the power bus 3006, and a low bandwidth data port 3116.

A contact monitor 3290 is coupled to an NE receptacle 3292. Power is fed to the NE receptacle 3292 from the monopolar receptacle 3136.

In one aspect, with reference to FIGS. 13-19, the modular energy system 3000 can be configured to detect instrument presence in a receptacle 3100, 3118, 3136 via a photo-interrupter, magnetic sensor, or other non-contact sensor integrated into the receptacle 3100, 3118, 3136. This approach prevents the necessity of allocating a dedicated presence pin on the MTD connector to a single purpose and instead allows multi-purpose functionality for MTD signal pins 6-9 while continuously monitoring instrument presence.

In one aspect, with reference to FIGS. 13-19, the modules of the modular energy system 3000 can include an optical link allowing high speed communication (10-50 Mb/s) across the patient isolation boundary. This link would carry device communications, mitigation signals (watchdog, etc.), and low bandwidth run-time data. In some aspects, the optical link(s) will not contain real-time sampled data, which can be done on the non-isolated side.

In one aspect, with reference to FIGS. 13-19, the modules of the modular energy system 3000 can include a multi-function circuit block which can: (i) read presence resistor values via A/D and current source, (ii) communicate with legacy instruments via hand switch Q protocols, (iii) communicate with instruments via local bus 1-Wire protocols, and (iv) communicate with CAN FD-enabled surgical instruments. When a surgical instrument is properly identified by an energy generator module, the relevant pin functions and communications circuits are enabled, while the other unused functions are disabled or disconnected and set to a high impedance state.

In one aspect, with reference to FIGS. 13-19, the modules of the modular energy system 3000 can include a pulse/stimulation/auxiliary amplifier. This is a flexible-use amplifier based on a full-bridge output and incorporates functional isolation. This allows its differential output to be referenced to any output connection on the applied part (except, in some aspects, a monopolar active electrode). The amplifier output can be either small signal linear (pulse/stim) with waveform drive provided by a DAC or a square wave drive at moderate output power for DC applications such as DC motors, illumination, FET drive, etc. The output voltage and current are sensed with functionally isolated voltage and current feedback to provide accurate impedance and power measurements to the FPGA. Paired with a CAN FD-enabled instrument, this output can offer motor/motion control drive, while position or velocity feedback is provided by the CAN FD interface for closed loop control.

As described in greater detail herein, a modular energy system comprises a header module and one or more functional or surgical modules. In various instances, the modular energy system is a modular energy system. In various instances, the surgical modules include energy modules, communication modules, user interface modules; however, the surgical modules are envisioned to be any suitable type of functional or surgical module for use with the modular energy system.

Modular energy system offers many advantages in a surgical procedure, as described above in connection with the modular energy systems 2000 (FIGS. 6-12), 3000 (FIGS. 13-15). However, cable management and setup/teardown time can be a significant deterrent. Various aspects of the present disclosure provide a modular energy system with a single power cable and a single power switch to control startup and shutdown of the entire modular energy system, which obviated the need to individually activate and deactivate each individual module from which the modular energy system is constructed. Also, various aspects of the present disclosure provide a modular energy system with power management schemes that facilitate a safe and, in some instances, concurrent delivery of power to the modules of a modular energy system.

Figure 20:
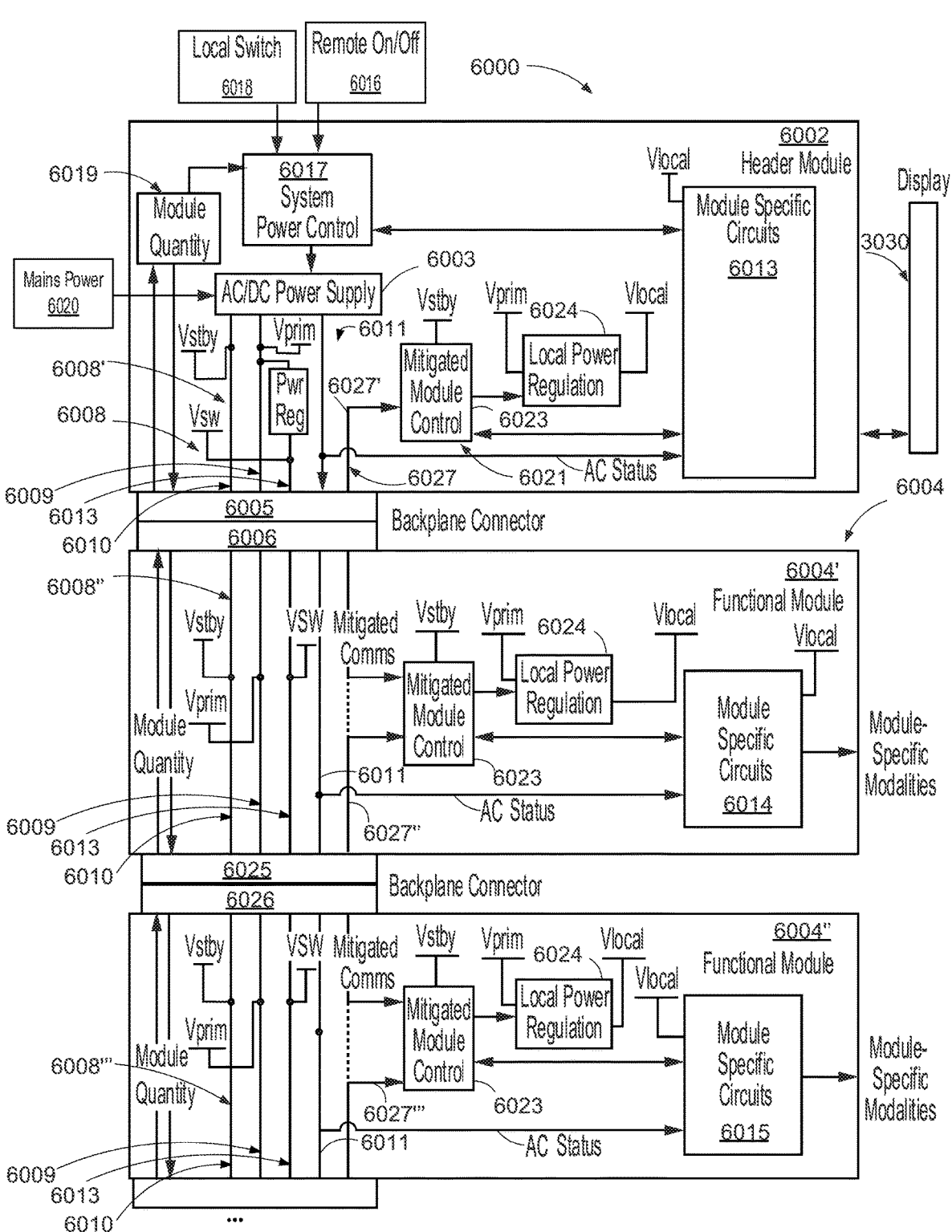
FIG. 20 is a schematic diagram of a modular energy system stack illustrating a power backplane, in accordance with at least one aspect of the present disclosure.

In various aspects, as illustrated in FIG. 20, a modular energy system 6000 that is similar in many respects to the modular energy systems 2000 (FIGS. 6-12), 3000 (FIGS. 13-15). For the sake of brevity, various details of the modular energy system 6000, which are similar to the modular energy system 2000 and/or the modular energy system 3000, are not repeated herein.

The modular energy system 6000 comprises a header module 6002 and an "N" number of surgical modules 6004, where "N" is an integer greater than or equal to one. In various examples, the modular energy system 6000 includes a UI module such as, for example, the UI module 3030 and/or a communication module such as, for example, the communication module 3032. Furthermore, pass-through hub connectors couple individual modules to one another in a stack configuration. In the example of FIG. 20, the header module 6002 is coupled to a surgical module 6004 via pass-through hub connectors 6005, 6006.

The modular energy system 6000 comprises an example power architecture that consists of a single AC/DC power supply 6003 that provides power to all the surgical modules in the stack. The AC/DC power supply 6003 is housed in the header module 6002, and utilizes a power backplane 6008 to distribute power to each module in the stack. The example of FIG. 20 demonstrates three separate power domains on the power backplane 6008: a primary power domain 6009, a standby power domain 6010, and an Ethernet switch power domain 6013.

In the example illustrated in FIG. 20, the power backplane 6008 extends from the header module 6002 through a number of intermediate modules 6004 to a most bottom, or farthest, module in the stack. In various aspects, the power backplane 6008 is configured to deliver power to a surgical module 6004 through one or more other surgical modules 6004 that are ahead of it in the stack. The surgical module 6004 receiving power from the header module 6002 can be coupled to a surgical instrument or tool configured to deliver therapeutic energy to a patient.

The primary power domain 6009 is the primary power source for the functional module-specific circuits 6013, 6014, 6015 of the modules 6002, 6004. It consists of a single voltage rail that is provided to every module. In at least one example, a nominal voltage of 60V can be selected to be higher than the local rails needed by any module, so that the modules can exclusively implement buck regulation, which is generally more efficient than boost regulation.

In various aspects, the primary power domain 6009 is controlled by the header module 6002. In certain instances, as illustrated in FIG. 20, a local power switch 6018 is positioned on the header module 6002. In certain instances, a remote on/off interface 6016 can be configured to control a system power control 6017 on the header module 6002, for example. In at least one example, the remote on/off interface 6016 is configured to transmit pulsed discrete commands (separate commands for On and Off) and a power status telemetry signal. In various instances, the primary power domain 6009 is configured to distribute power to all the modules in the stack configuration following a user-initiated power-up.

Figure 21:
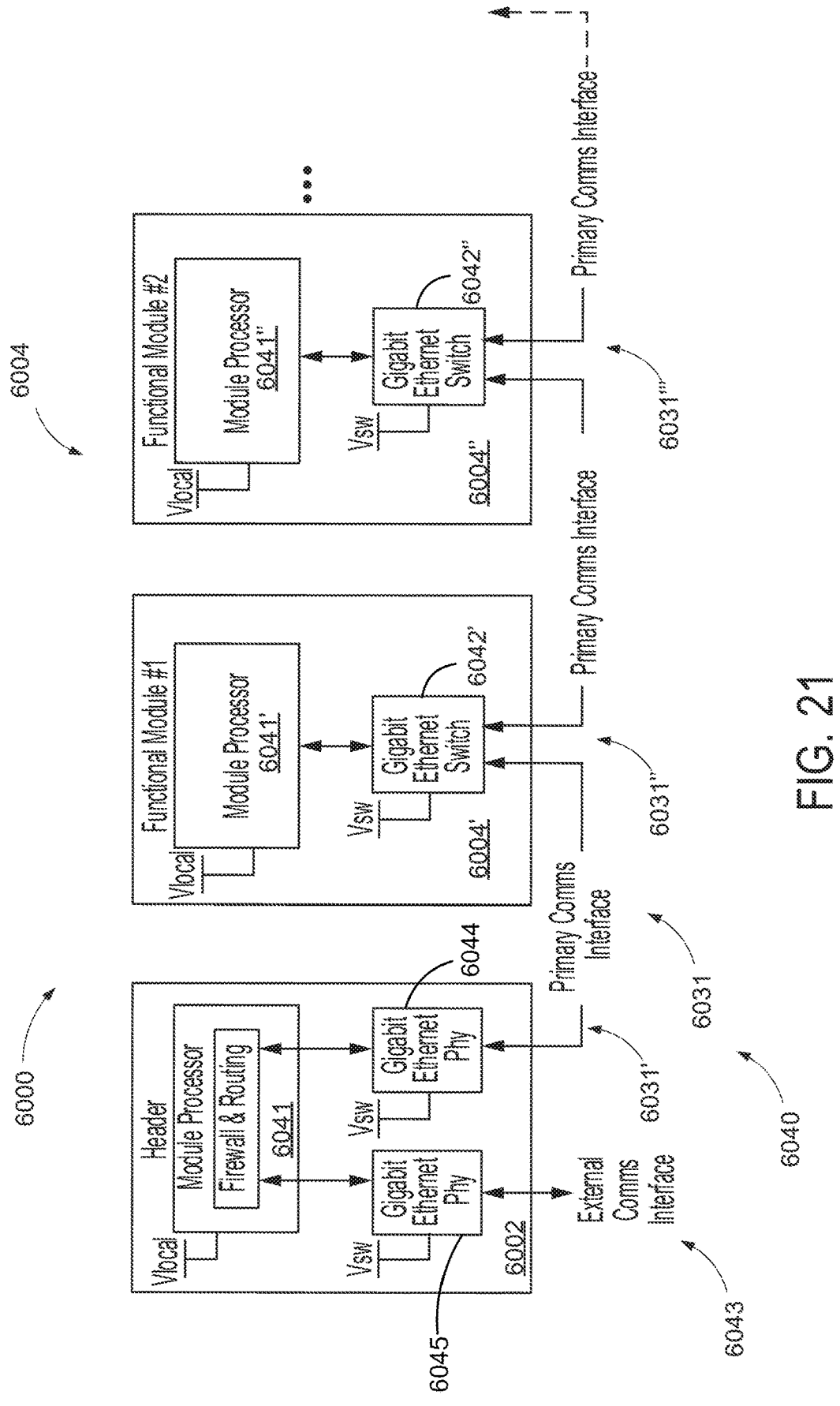
FIG. 21 is a schematic diagram of a modular energy system, in accordance with at least one aspect of the present disclosure.

In various aspects, as illustrated in FIG. 21, the modules of the modular energy system 6000 can be communicably coupled to the header module 6002 and/or to each other via a communication (Serial bus/Ethernet) interface 6040 such that data or other information is shared by and between the modules of which the modular energy system is constructed. An Ethernet switch domain 6013 can be derived from the primary power domain 6009, for example. The Ethernet switch power domain 6013 is segregated into a separate power domain, which is configured to power Ethernet switches within each of the modules in the stack configuration, so that the primary communications interface 6040 will remain alive when local power to a module is removed. In at least one example, the primary communication interface 6040 comprises a 1000BASE-T Ethernet network, where each module represents a node on the network, and each module downstream from the header module 6002 contains a 3-port Ethernet switch for routing traffic to the local module or passing the data up or downstream as appropriate.

Furthermore, in certain examples, the modular energy system 6000 includes secondary, low speed, communication interface between modules for critical, power related functions including module power sequencing and module power status. The secondary communications interface can, for example, be a multi-drop Local Interconnect Network (LIN), where the header module is the master and all downstream modules are slaves.

In various aspects, as illustrated in FIG. 20, a standby power domain 6010 is a separate output from the AC/DC power supply 6003 that is always live when the supply is connected to mains power 6020. The standby power domain 6010 is used by all the modules in the system to power circuitry for a mitigated communications interface, and to control the local power to each module. Further, the standby power domain 6010 is configured to provide power to circuitry that is critical in a standby mode such as, for example, on/off command detection, status LEDs, secondary communication bus, etc.

In various aspects, as illustrated in FIG. 20, the individual surgical modules 6004 lack independent power supplies and, as such, rely on the header module 6002 to supply power in the stack configuration. Only the header module 6002 is directly connected to the mains power 6020. The surgical modules 6004 lack direct connections to the mains power 6020, and can receive power only in the stack configuration. This arrangement improves the safety of the individual surgical modules 6004, and reduces the overall footprint of the modular energy system 6000. This arrangement further reduces the number of cords required for proper operation of the modular energy system 6000, which can reduce clutter and footprint in the operating room.

Accordingly, a surgical instrument connected to surgical modules 6004 of a modular energy system 6000, in the stack configuration, receives therapeutic energy for tissue treatment that is generated by the surgical module 6004 from power delivered to the surgical module 6004 from the AC/DC power supply 6003 of the header module 6002.

In at least one example, while a header module 6002 is assembled in a stack configuration with a first surgical module 6004', energy can flow from the AC/DC power supply 6003 to the first surgical module 6004'. Further, while a header module 6002 is assembled in a stack configuration with a first surgical module 6004' (connected to the header module 6002) and a second surgical module 6004" (connected to the first surgical module 6004'), energy can flow from the AC/DC power supply 6003 to the second surgical module 6004" through the first surgical module 6004'.

The energy generated by the AC/DC power supply 6003 of the header module 6002 is transmitted through a segmented power backplane 6008 defined through the modular energy system 6000. In the example of FIG. 20, the header module 6002 houses a power backplane segment 6008', the first surgical module 6004' houses a power backplane segment 6008", and the second surgical module 6004" houses a power backplane segment 6008". The power backplane segment 6008' is detachably coupled to the power backplane segment 6008" in the stack configuration. Further, the power backplane 6008" is detachably coupled to the power backplane segment 6008"' in the stack configuration. Accordingly, energy flows from the AC/DC power supply 6003 to the power backplane segment 6008', then to the power backplane segment 6008", and then to the power backplane segment 6008"'.

In the example of FIG. 20, the power backplane segment 6008' is detachably connected to the power backplane segment 6008" via pass-through hub connectors 6005, 6006 in the stack configuration. Further, the power backplane segment 6008" is detachably connected to the power backplane segment 6008"' via pass-through hub connectors 6025, 6056 in the stack configuration. In certain instances, removing a surgical module from the stack configuration severs its connection to the power supply 6003. For example, separating the second surgical module 6004" from the first surgical module 6004' disconnects the power backplane segment 6008"' from the power backplane segment 6008". However, the connection between the power backplane segment 6008" and the power backplane segment 6008"' remains intact as long as the header module 6002 and the first surgical module 6004' remain in the stack configuration. Accordingly, energy can still flow to the first surgical module 6004' after disconnecting the second surgical module 6004" through the connection between the header module 6002 and the first surgical module 6004'. Separating connected modules can be achieved, in certain instances, by simply pulling the surgical modules 6004 apart.

In the example of FIG. 20, each of the modules 6002, 6004 includes a mitigated module control 6023. The mitigated module controls 6023 are coupled to corresponding local power regulation modules 6024 that are configured to regulate power based on input from the mitigated module controls 6023. In certain aspects, the mitigated module controls 6023 allow the header module 6002 to independently control the local power regulation modules 6024.

The modular energy system 6000 further includes a mitigated communications interface 6021 that includes a segmented communication backplane 6027 extending between the mitigated module controls 6023. The segmented communication backplane 6027 is similar in many respects to the segmented power backplane 6008. Mitigated Communication between the mitigated module controls 6023 of the header module 6002 and the surgical modules 6004 can be achieved through the segmented communication backplane 6027 defined through the modular energy system 6000. In the example of FIG. 20, the header module 6002 houses a communication backplane segment 6027', the first surgical module 6004' houses a communication backplane segment 6027", and the second surgical module 6004" houses a communication backplane segment 6027'". The communication backplane segment 6027' is detachably coupled to the communication backplane segment 6027" in the stack configuration via the pass-through hub connectors 6005, 6006. Further, the communication backplane 6027" is detachably coupled to the communication backplane segment 6027" in the stack configuration via the pass-through hub connectors 6025, 6026.

Although the example of FIG. 20 depicts a modular energy system 6000 includes a header module 6002 and two surgical modules 6004' 6004", this is not limiting. Modular energy systems with more or less surgical modules are contemplated by the present disclosure. In some aspects, the modular energy system 6000 includes other modules such as, for example, the communications module 3032 (FIG. 15). In some aspects, the header module 6502 supports a display screen such as, for example, the display 2006 (FIG. 7A) that renders a GUI such as, for example, the GUI 2008 for relaying information regarding the modules connected to the header module 6002. As described in greater detail in connection with the example of FIG. 15, in some aspects, the GUI 2008 of the display screen 2006 can provide a consolidated point of control all of the modules making up the particular configuration of a modular energy system.

FIG. 21 depicts a simplified schematic diagram of the modular energy system 6000, which illustrates a primary communications interface 6040 between the header module 6002 and the surgical modules 6004. The primary communications interface 6040 communicably connects module processors 6041, 6041', 6041" of the header module 6002 and the surgical modules 6004. Commands generated by the module processor 6041 of the header module are transmitted downstream to a desired functional surgical module via the primary communications interface 6040. In certain instances, the primary communications interface 6040 is configured to establish a two-way communication pathway between neighboring modules. In other instances, the primary communications interface 6040 is configured to establish a one-way communication pathway between neighboring modules.

Furthermore, the primary communications interface 6040 includes a segmented communication backplane 6031, which is similar in many respects to the segmented power backplane 6008. Communication between the header module 6002 and the surgical modules 6004 can be achieved through the segmented communication backplane 6031 defined through the modular energy system 6000. In the example of FIG. 21, the header module 6002 houses a communication backplane segment 6031', the first surgical module 6004' houses a communication backplane segment 6031", and the second surgical module 6004" houses a communication backplane segment 6031'". The communication backplane segment 6031' is detachably coupled to the communication backplane segment 6031" in the stack configuration via the pass-through hub connectors 6005, 6006. Further, the communication backplane 6031" is detachably coupled to the communication backplane segment 6031" in the stack configuration via the pass-through hub connectors 6025, 6026.

In at least one example, as illustrated in FIG. 21, the primary communications interface 6040 is implemented using the DDS framework running on a Gigabit Ethernet interface. The module processors 6041, 6041', 6041" are connected to Gigabit Ethernet Phy 6044, and Gigabit Ethernet Switches 6042', 6042". In the example of FIG. 21, the segmented communication backplane 6031 connects the Gigabit Ethernet Phy 6044 and the Gigabit Ethernet Switches 6042 of the neighboring modules.

In various aspects, as illustrated in FIG. 21, the header module 6002 includes a separate Gigabit Ethernet Phy 6045 for an external communications interface 6043 with the processor module 6041 of the header module 6002. In at least one example, the processor module 6041 of the header module 6002 handles firewalls and information routing.

Referring to FIG. 20, the AC/DC power supply 6003 may provide an AC Status signal 6011 that indicates a loss of AC power supplied by the AC/DC power supply 6003. The AC status signal 6011 can be provided to all the modules of the modular energy system 6000 via the segmented power backplane 6008 to allow each module as much time as possible for a graceful shutdown, before primary output power is lost. The AC status signal 6011 is received by the module specific circuits 6013, 6014, 6015, for example. In various examples, the system power control 6017 can be configured to detect AC power loss. In at least one example, the AC power loss is detected via one or more suitable sensors.

Referring to FIGS. 20 and 21, to ensure that a local power failure in one of the modules of the modular energy system 6000 does not disable the entire power bus, the primary power input to all modules can be fused or a similar method of current limiting can be used (e-fuse, circuit breaker, etc.). Further, Ethernet switch power is segregated into a separate power domain 6013 so that the primary communications interface 6040 remains alive when local power to a module is removed. In other words, primary power can be removed and/or diverted from a surgical module without losing its ability to communicate with other surgical modules 6004 and/or the header module 6002.

Flexible Power Techniques

Having described a general implementation the header and modules of modular energy systems 2000, 3000, 6000, the disclosure now turns to describe various aspects of other modular energy systems. The other modular energy systems are substantially similar to the modular energy system 2000, the modular energy system 3000, and/or the modular energy system 6000. For the sake of brevity, various details of the other modular energy systems being described in the following sections, which are similar to the modular energy system 2000, the modular energy system 3000, and/or the modular energy system 6000, are not repeated herein. Any aspect of the other modular energy systems described below can be brought into the modular energy system 2000, the modular energy system 3000, or the modular energy system 6000.

The disclosure now turns to various aspects of intelligent data ports for the modular energy system 2000, 3000, 6000. In one aspect, the intelligent data ports include flexible ports for modular energy system 2000, 3000, 6000 accessories. In another aspect, the present disclosure provides a flexible serial communications configuration for the modular energy system 2000, 3000, 6000. In another aspect, the present disclosure provides a remote power control interface for modular energy systems 2000, 3000, 6000.

Flexible Port for Modular Energy System Accessories

Modular energy systems 2000, 3000, 6000 described above require support for interfacing and connecting future accessories and technologies to the modular energy system 2000, 3000, 6000. In one aspect, the present disclosure provides an interface for the modular energy system 2000, 3000, 6000, where the interface is configured to support a wide variety of such future accessories.

In one aspect, the present disclosure provides circuits and associated methods for controlling a flexible and extensible port for coupling accessories to the modular energy system 2000, 3000, 6000. This port, which may be referred to herein as the "Accessory Port" (Acc. Port), provides a variety of functionality that facilitates support for a wide range of applications and potential future accessories.

More particularly, the circuits and associated methods may include one or more of the following aspects. First, a circuit according to one aspect of the present disclosure may include power delivery to the accessory for powering circuitry or features internal to the accessory.

Second, the circuit according to one aspect of the present disclosure includes a current limiter to prevent any accessory from over-burdening the power budget of the modular energy system 2000, 3000, 6000. In another aspect, the current limiter is configured to eliminate risk of damage to the modular energy system 2000, 3000, 6000 in case of a malfunctioning accessory. In another aspect, the current limiter is controllable by a processor onboard the header module 2002, 3002, 6002 or energy module 2004, 3005, 6004 of the modular energy system 2000, 3000, 6000, which allows for power budgeting, cyber security, or fault-recovery techniques, or a combination thereof, among other functions.

Third, the circuit according to one aspect of the present disclosure may include a flexible serial communication interface. In various aspects, the flexible serial communication interface may support the RS232 and RS485 communication protocols, among other communication protocols, for example. It will be appreciated that the RS232 and RS485 communication protocols may be uniquely advantageous over other communication protocols in certain applications. Accordingly, providing a flexible serial communication interface allows for any future needs to be accommodated.

Fourth, the circuit according to one aspect of the present disclosure may include a presence detection circuit or algorithm functionality to detect the presence of an attached accessory or enable the header module 2002, 3002, 6002 or energy module 2004, 3004, 6004 of the modular energy system 2000, 3000, 6000 to detect the presence of an attached accessory. Further, in one aspect, the presence detection circuit or algorithm functionality may be implemented such that the presence configuration of the accessory immediately identifies to the modular energy system 2000, 3000, 6000 which communication mode is required for using the accessory, e.g., RS232 or RS485 communications protocols. This allows for many types of accessories to be used in field applications because the accessory itself determines the required communication protocol.

Fifth, the circuit according to one aspect of the present disclosure may include an isolated domain (similar to footswitch ports, for example) to support both surgeon-accessible and non-surgeon accessible accessories, for example.

Figure 22:
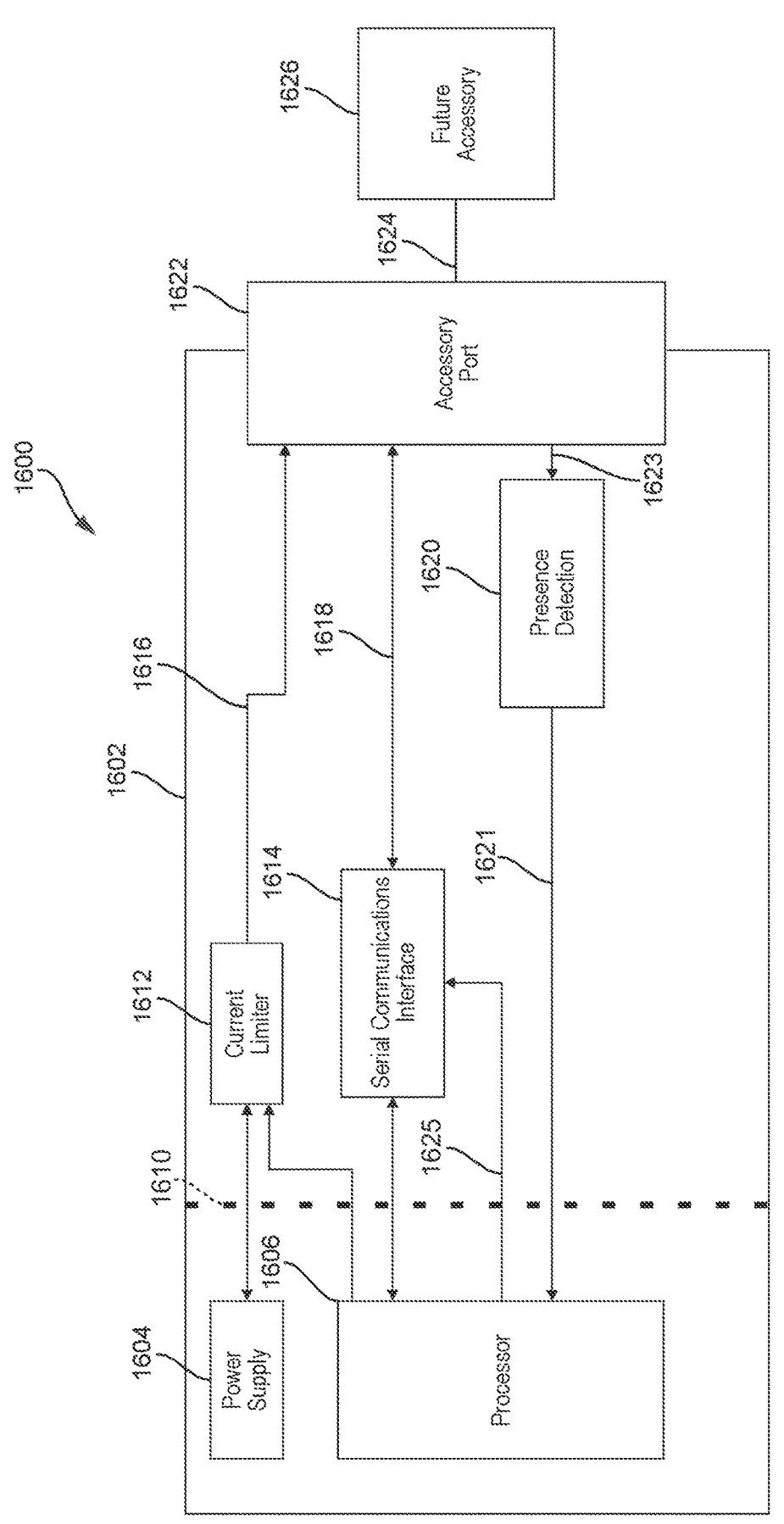
FIG. 22 is a diagram of a modular energy system accessory circuit comprising a flexible accessory port to support an accessory through the output, in accordance with at least one aspect of the present disclosure.

Turning now to the figures, FIG. 22 is a diagram of a modular energy system accessory circuit 1600 comprising a flexible accessory port 1622 to support an accessory 1626 through the interface 1624, in accordance with at least one aspect of the present disclosure. An accessory 1626 may be any electrical circuit or device capable of receiving power from and/or communicating with the modular energy system 2000, 3000, 6000. In the example shown in FIG. 22, the modular energy system 2000, 3000, 6000 accessory circuit 1600 comprises a power supply 1604 and a processor 1606 isolated from the accessory port 1622 and the accessory 1626 by an isolation barrier 1610. The isolation barrier 1610 defines an isolated domain (similar to footswitch ports, for example) to support both surgeon-accessible and non-surgeon accessible accessories 1626, for example. In one aspect, the processor 1606 may be the header processor 3158 as discussed above. In one aspect, the power supply 1604 may be configured to deliver power to the accessory 1626 for powering circuitry or features internal to the accessory 1626.

In one aspect, the power supply 1604 and the processor 1606 are coupled to a current limiter circuit 1612, which is coupled to the accessory port 1622 via output 1616. The current limiter circuit 1612 is configured to prevent the accessory 1626 from over-burdening the power budget of the power supply 1604 of the accessory circuit 1600 or the modular energy system 2000, 3000, 6000. In another aspect, the current limiter circuit 1612 is configured to eliminate risk of damage to the accessory circuit 1600 or the modular energy system 2000, 3000, 6000 in case of a malfunctioning accessory 1626. In another aspect, the current limiter circuit 1612 may be controlled by the onboard processor 1606, which allows for power budgeting, cyber security, or fault-recovery techniques, or combinations thereof, among other functions.

In one aspect, the processor 1606 may be coupled to the accessory port 1622 via a flexible serial communications interface 1614, otherwise referred to as a serial transceiver circuit 1614. In one aspect, the flexible serial communications interface 1614 may support the RS232 and RS485 communication protocols, among other communication protocols, for example, as selected by the processor 1610 via protocol select line 1625. It will be appreciated that the RS232 and RS485 communication protocols may be uniquely advantageous over other communication protocols in certain implementations. Accordingly, providing the flexible serial communications interface 1614 enables the accessory circuit 1600 of the modular energy system 2000, 3000, 6000 to accommodate future communications protocol needs.

In one aspect, the accessory circuit 1600 of the modular energy system 2000, 3000, 6000 comprises a presence detection circuit 1620 or algorithm functionality to detect presence of an accessory 1626 connected to the accessory port 1622 and to enable the modular energy system 2000, 3000, 6000 header module 2002, 3002, 6002 to detect the presence of the accessory. The presence detection circuit 1620 may be coupled to the processor 1606 via line 1621 and to the accessory port 1622 via line 1623. Further, in one aspect, the presence detection 1620 circuit or algorithm functionality may be implemented such that the presence configuration of the accessory 1626 identifies to the accessory circuit 1600 or other components of the modular energy system 2000, 3000, 6000 which communication mode is required for using the accessory 1626. In one aspect, the accessory 1626 may identify (or configure) the serial communications interface 1614 which communications mode is required. This allows for many types of accessories 1626 to be used in field applications because the accessory 1626 itself determines the required communication protocol.

Figure 23:
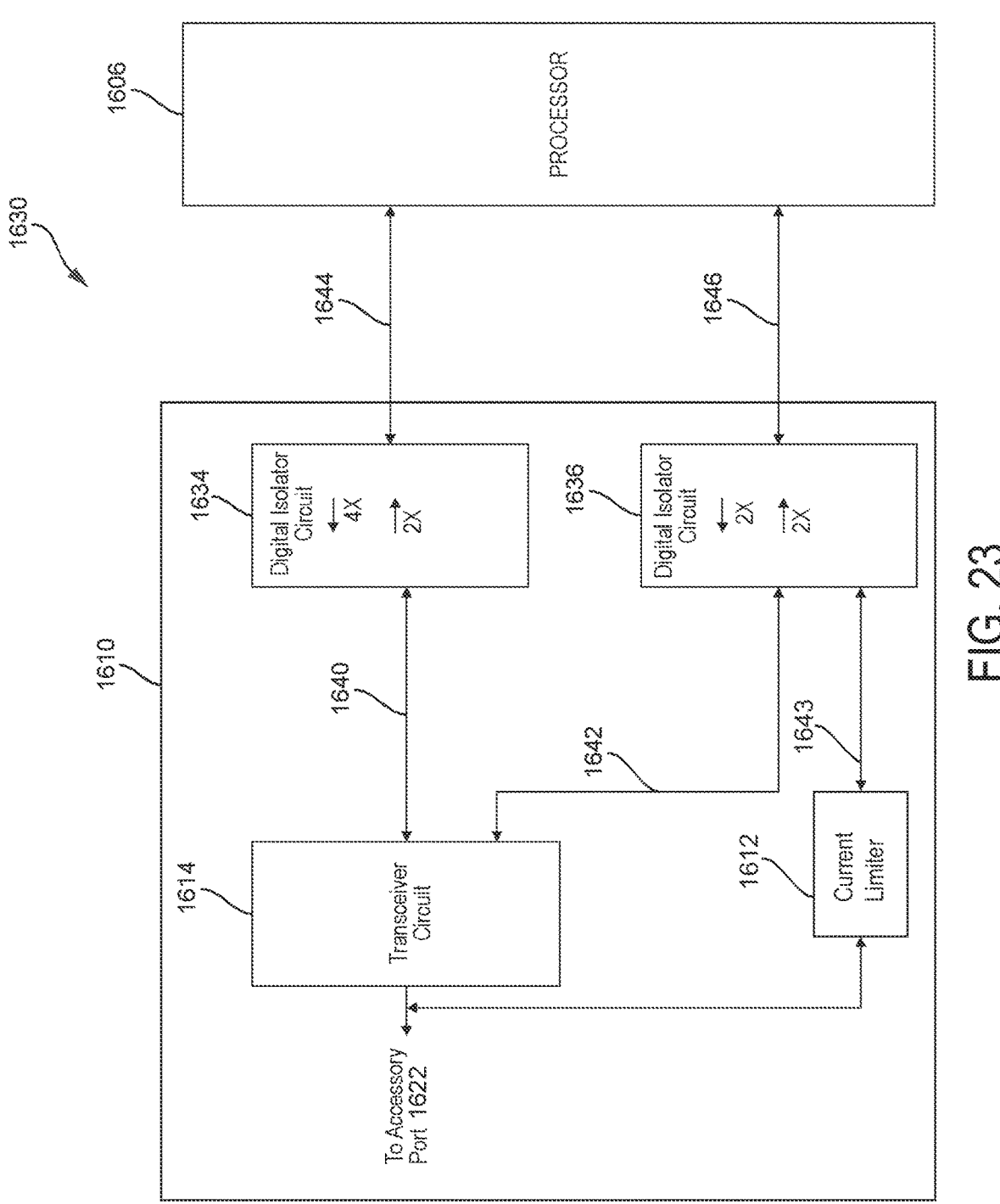
FIG. 23 is an electrical isolation circuit 1630 portion of the modular energy system accessory circuit shown in FIG. 22, in accordance with at least one aspect of the present disclosure.

FIG. 23 is an electrical isolation circuit 1630 portion of the modular energy system accessory circuit 1600 shown in FIG. 22, in accordance with at least one aspect of the present disclosure. In one aspect, the isolation barrier 1610 shown in FIG. 22 comprises a first digital isolator circuit 1634 and a second digital isolator circuit 1636. Each one of the digital isolator circuits 1634, 1636 is coupled between the processor 1606 and the transceiver circuit 1614, e.g., the serial communications interface 1614 and current limiter shown in FIG. 22. The first digital isolator circuit 1634 is coupled to the processor 1606 via a first bus lines 1644. The second digital isolator circuit 1636 is coupled to the processor 1606 via a second bus line 1646. The first and second digital isolator circuits 1634, 1636 provide electrical isolation to allow use of surgeon-accessible accessories 1626 and reduce or eliminate shock hazard to the patient or surgeon. In one aspect, the first and second digital isolator circuits 1634, 1636 may be high speed six-channel digital isolators, for example.

In one aspect, the first digital isolator circuit 1634 may be coupled to the transceiver circuit 1614 via a third bus lines 1640. The second digital isolator circuit 1636 is coupled to the transceiver circuit 1614 via a fourth bus lines 1642 and to the current limiter 1612 via a fifth bus line 1643. The transceiver circuit 1614 portion of the flexible serial port is configured for both RS232 and RS485 serial protocols to maximize the functionality of the modular energy system 2000, 3000, 6000 in various applications and to enable the modular energy system 2000, 3000, 6000 functions to adapt to real-time needs, for example.

Figure 24:
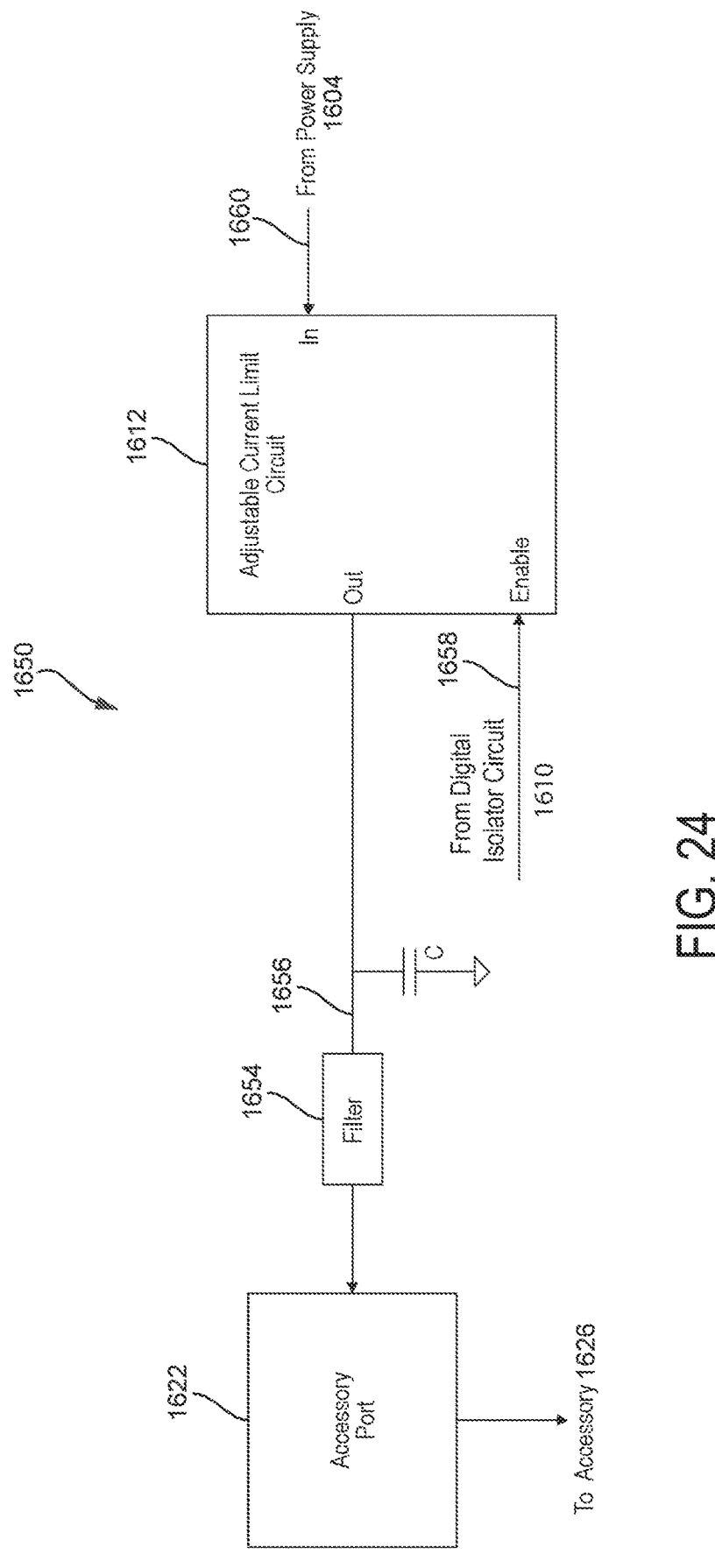
FIG. 24 is a current limit circuit portion of the modular energy system accessory circuit shown in FIG. 22, in accordance with at least one aspect of the present disclosure.

FIG. 24 is a current limit circuit 1650 portion of the modular energy system accessory circuit 1600 shown in FIG. 22, in accordance with at least one aspect of the present disclosure. The adjustable current limiter circuit 1612 receives power from the power supply 1604 at input 1660. The output 1656 of the adjustable current limiter circuit 1612 is provided when the adjustable current limiter circuit 1612 is enabled by the processor 1606 at input 1658. The output 1656 of the adjustable current limiter circuit 1612 is provided to an filter 1654 which is coupled to the accessory port 1622. In one aspect, the filter 1654 may be a common mode filter, differential mode filter, TVS device, or a combination thereof, to suppress noise in and out of the current limiter circuit 1612. In one aspect, the adjustable current limiter circuit 1612 prevents the accessory 1626 from drawing too much current and thus limits the power that the accessory 1626 can use to prevent damage to the modular energy system 2000, 3000, 6000.

To provide cybersecurity, the adjustable current limiter circuit 1612 can power down or cease power delivery to the accessory 1626 if it is an unacceptable accessory. In case of accessory 1626 malfunction, the adjustable current limiter circuit 1612 may power cycle the accessory 1626 to resolve the malfunction. In addition, the adjustable current limiter circuit 1612 alleviates the power budget of the modular energy system 2000, 3000, 6000 by limiting power draw from the accessory 1626. It will appreciated that the above referenced functions are be driven by the processor 1606.

Figure 25:
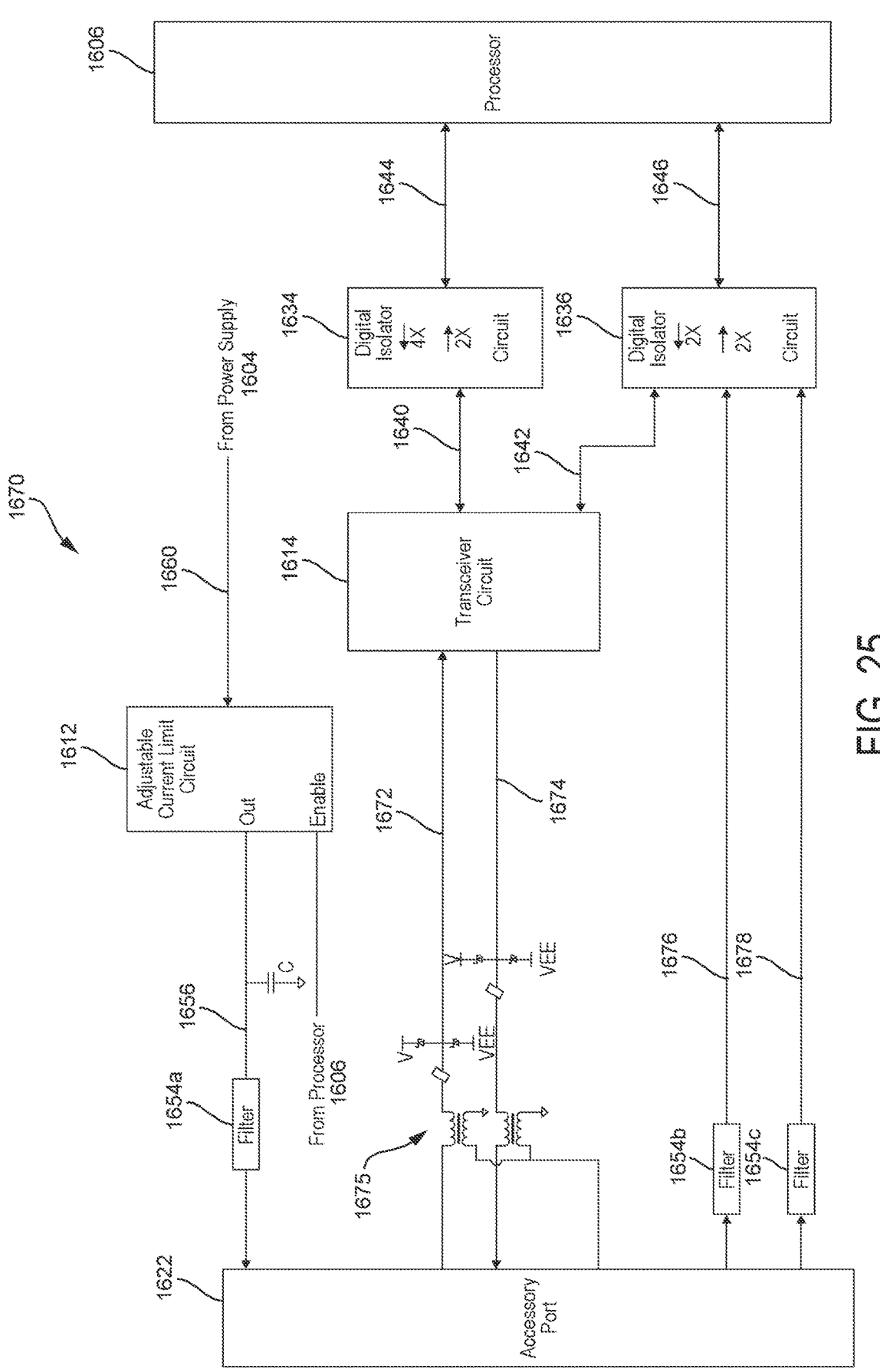
FIG. 25 is a detailed view of the electrical isolation circuit portion and the current limit circuit portion of the of the modular energy system accessory circuit shown in FIGS. 22-24, in accordance with at least one aspect of the present disclosure.

FIG. 25 is a detailed view of the electrical isolation circuit 1630 portion and the current limit circuit 1650 portion of the of the modular energy system accessory circuit 1600 shown in FIGS. 22-24, in accordance with at least one aspect of the present disclosure. Accordingly, for conciseness and clarity of disclosure, corresponding portions of FIGS. 23 and 24 will not be repeated here. As shown in FIG. 25, the adjustable current limiter circuit 1612 is coupled to the accessory port 1622 via a first filter 1654*a*. The transceiver circuit 1614 is coupled to the accessory port 1622 via a common mode choke 1675 that couples the signals on lines 1672, 1674 to the transceiver circuit 1614 and the accessory 1626. In one aspect, signal lines 1672, 1674 are bi-directional in RS-485 mode and uni-directional in RS-232 mode, for example. The digital isolator circuit 1636 is coupled to a first presence line 1676 and a second presence line 1678. The first and second presence lines 1676, 1678 are coupled to the accessory port 1622 through second and third filters 1654*b*, 1654*c*, respectively. As discussed above, the filters 1654*a*, 1654*b*, 1654*c* may be a common mode filter, differential mode filter, TVS device, or a combination thereof.

Figure 26:
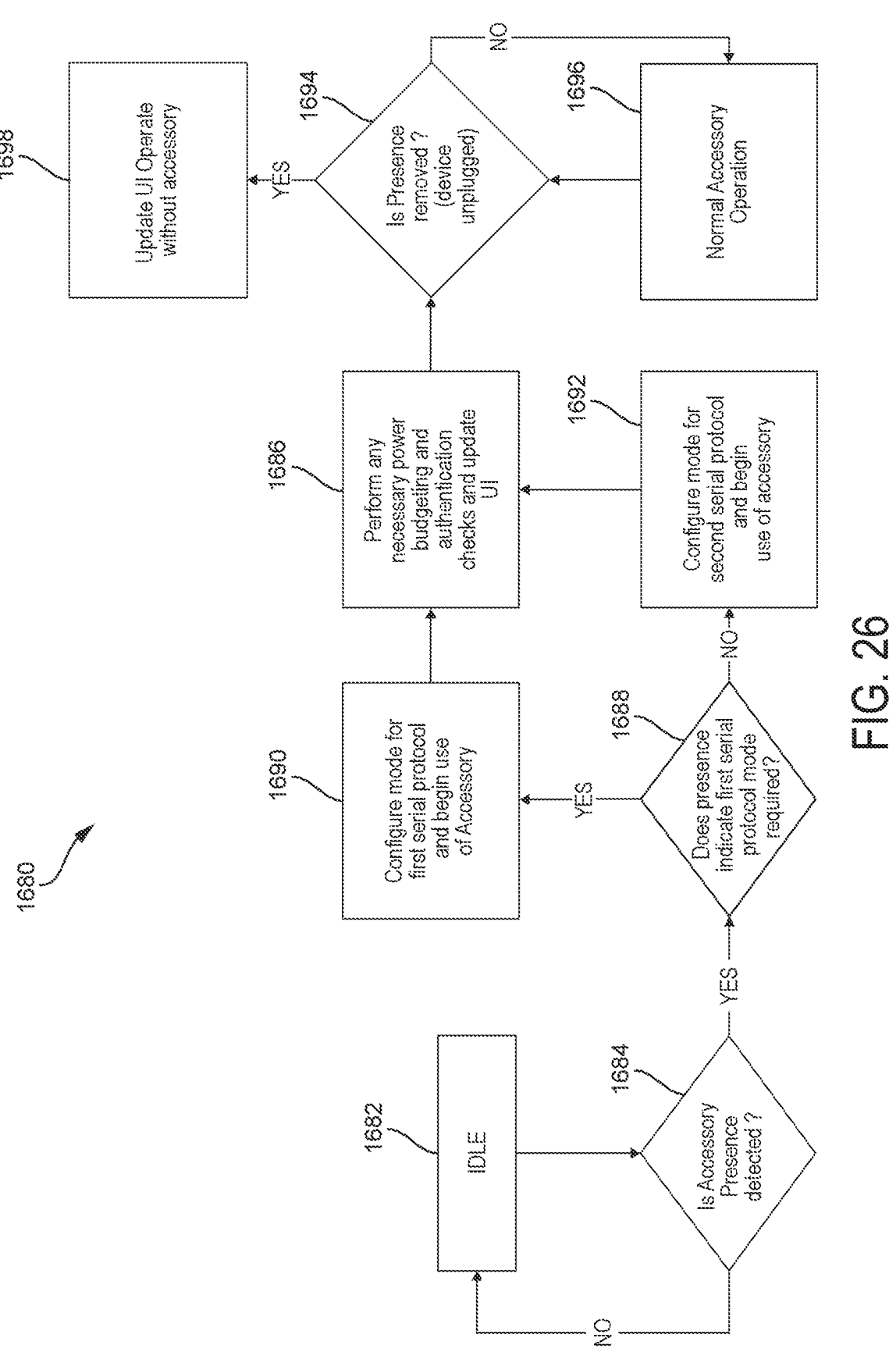
FIG. 26 is a logic flow diagram to detect the presence of an accessory and initiate automatic serial communication between the accessory and the modular energy system accessory circuit shown in FIG. 22, in accordance with at least one aspect of the present disclosure.

FIG. 26 is a logic flow diagram 1680 to detect the presence of an accessory and initiate automatic serial communication between the accessory and the modular energy system accessory circuit 1600 shown in FIG. 22, in accordance with at least one aspect of the present disclosure. Generally, the presence detection circuit 1620 detects "arriving" or "departing" presence (i.e., plug-in, unplug) of an accessory 1626. The presence detection circuit 1620 instructs the modular energy system 2000, 3000, 6000 which serial communication mode to use, for example, RS232 or RS485. The modular energy system 2000, 3000, 6000 automatically selects the appropriate communication mode based on the detected presence signal. This technique eliminates the need for negotiating the communication method that may be required by some other techniques.

Turning now to the logic flow diagram 1680 in FIG. 26 and the modular energy system accessory circuit 1600 comprising a flexible accessory port 1622 in FIG. 22, the presence detection circuit 1620 remains in idle 1682 and continually checks the presence of an accessory 1626 detected 1684 at the accessory port 1622. After the presence detection circuit 1620 detects 1684, at line 1623, the presence of an accessory 1626 plugged into the accessory port 1622, the presence detection circuit 1620 signals the processor 1606 via line 1620.

In the instance that the processor 1606 determines 1688 that the presence detection circuit 1620 indicates that a first serial protocol mode is required to communicate with the accessory 1626, the processor 1606 configures 1690 the communication mode for the first serial protocol and initiates communications with the accessory 1626 via the first serial protocol. In one aspect, the first serial protocol may be the RS232 protocol, for example. The processor 1606 then performs 1686 any necessary power budgeting and authentication checks and updates the user interface (UI).

In the instance that the processor 1606 determines 1688 that the presence detection circuit 1620 indicates that a protocol other than the first serial protocol is required to communicate with the accessory 1626, the processor 1606 configures 1692 the communication mode for a second serial communication protocol, such as for example, the RS485 serial protocol and initiates communication with the accessory 1626 via the second serial protocol. The processor 1606 then performs 1686 any necessary power budgeting and authentication checks and updates the user interface (UI). Following the presence detection by the presence detection circuit 1620, the operation of the modular energy system 2000, 3000, 6000 includes the accessory 1626 plugged into the accessory port 1622 and communication via the first or second communication protocol.

Once a serial communication protocol is configured 1690 and performed 1686 any necessary power budgeting and authentication checks and updated the UI, the processor 1606 determines 1694 the removal of the accessory 1626 (e.g., was the device unplugged?). In the instance that the accessory 1626 was not unplugged and remains plugged into the accessory port 1622, the processor 1606 enables 1696 normal operation of the accessory 1626 and loops back to determine 1694 whether the presence of the accessory 1626 has been removed. Once the processor 1606 determines 1694 that the accessory 1626 has been removed from the accessory port 1622, the processor 1606 updates 1698 the user interface and resumes operation of the modular energy system 2000, 3000, 6000 without the accessory 1626.

Flexible Universal Serial Bus (USB) Power Configuration for Modular Energy Systems As explained in the foregoing description, providing the modular energy system 2000, 3000, 6000 with serial interface functionality to support future accessories and technologies provides many advantages. Providing serial interface functionality for existing or future accessories, however, presents potential challenges related to cybersecurity, system reliability, and system power budgeting. In one aspect, future accessory expansion may comprise Universal Serial Bus (USB) functionality. Accordingly, in one aspect, the present disclosure provides flexible USB power configuration circuits and associated methods for the modular energy system 2000, 3000, 6000.

In one aspect, the present disclosure provides circuits and associated methods for controlling power delivery to USB ports of the modular energy system 2000, 3000, 6000, and in one aspect, the header module 2002 of the modular energy system 2000, 3000, 6000. It will be appreciated, however, that the circuits and associated methods may be applicable to any medical equipment utilizing USB ports. In one aspect, the circuits and associated methods according to the present disclosure provide to the onboard processor system independent power control for each USB port on the system, allowing for application, removal, and current limiting of the provided power. Several applications for this capability include security, fault recovery, and power budgeting, as explained in more detail in the following description and accompanying drawings.

Figure 27:
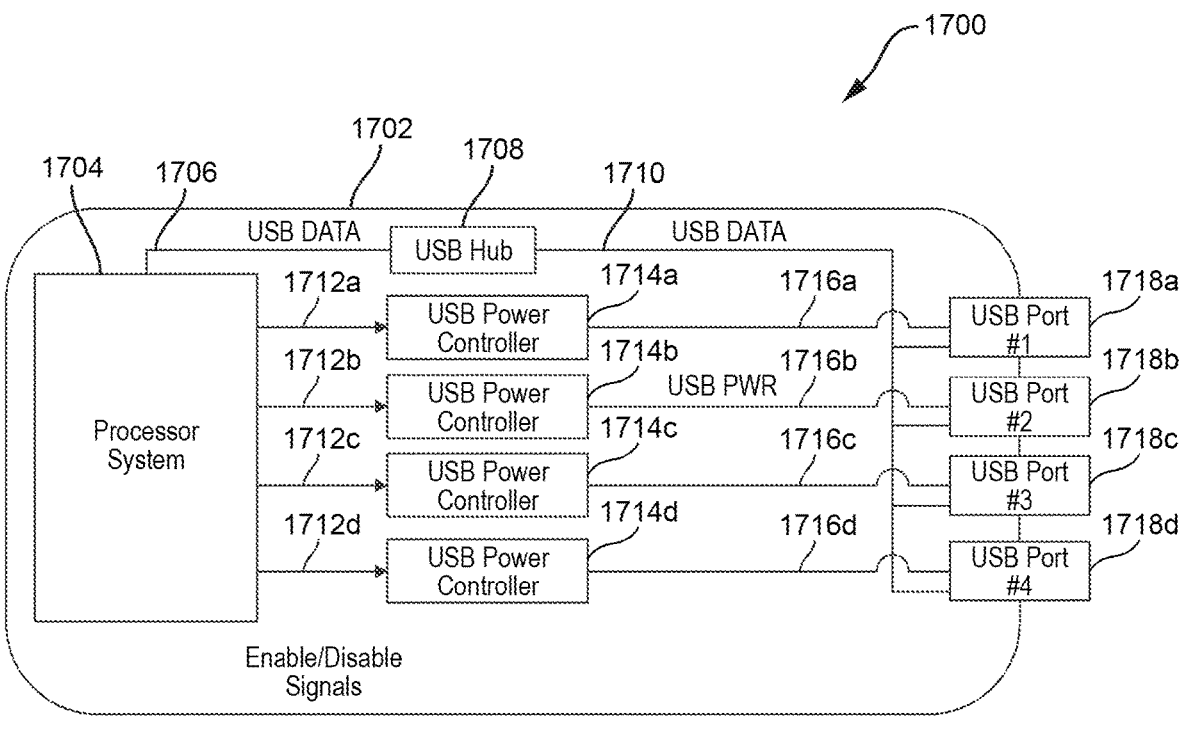
FIG. 27 is a flexible universal serial bus (USB) power configuration circuit for the modular energy system, in accordance with at least one aspect of the present disclosure.

Turning now to FIG. 27, there is shown a flexible universal serial bus (USB) power configuration circuit 1700 for the modular energy system 2000, 3000, 6000, in accordance with at least one aspect of the present disclosure. The flexible USB power configuration circuit 1700 provides power control for individual USB ports 1718a, 1718b, 1718c, 1718d, for example. Controlling the power of each USB port 1718a-1718d individual enhances cybersecurity protection, system reliability, and system power budgeting. The system processor 1704 transmits USB data over line 1706 to a USB hub 1708. USB data is transmitted from the USB hub 1708 over lines 1710 to the individual USB ports 1718a-1718d. Each of the individual USB ports 1718a-1718d are controlled by individual USB power controllers 1714a, 1714b, 1714c, 1714d, respectively. Each of the individual USB power controllers 1714a-1714d can be controlled by the system processor 1704 via individual enable/disable signals 1712a, 1712b, 1712c, 1712d.

Figure 28:
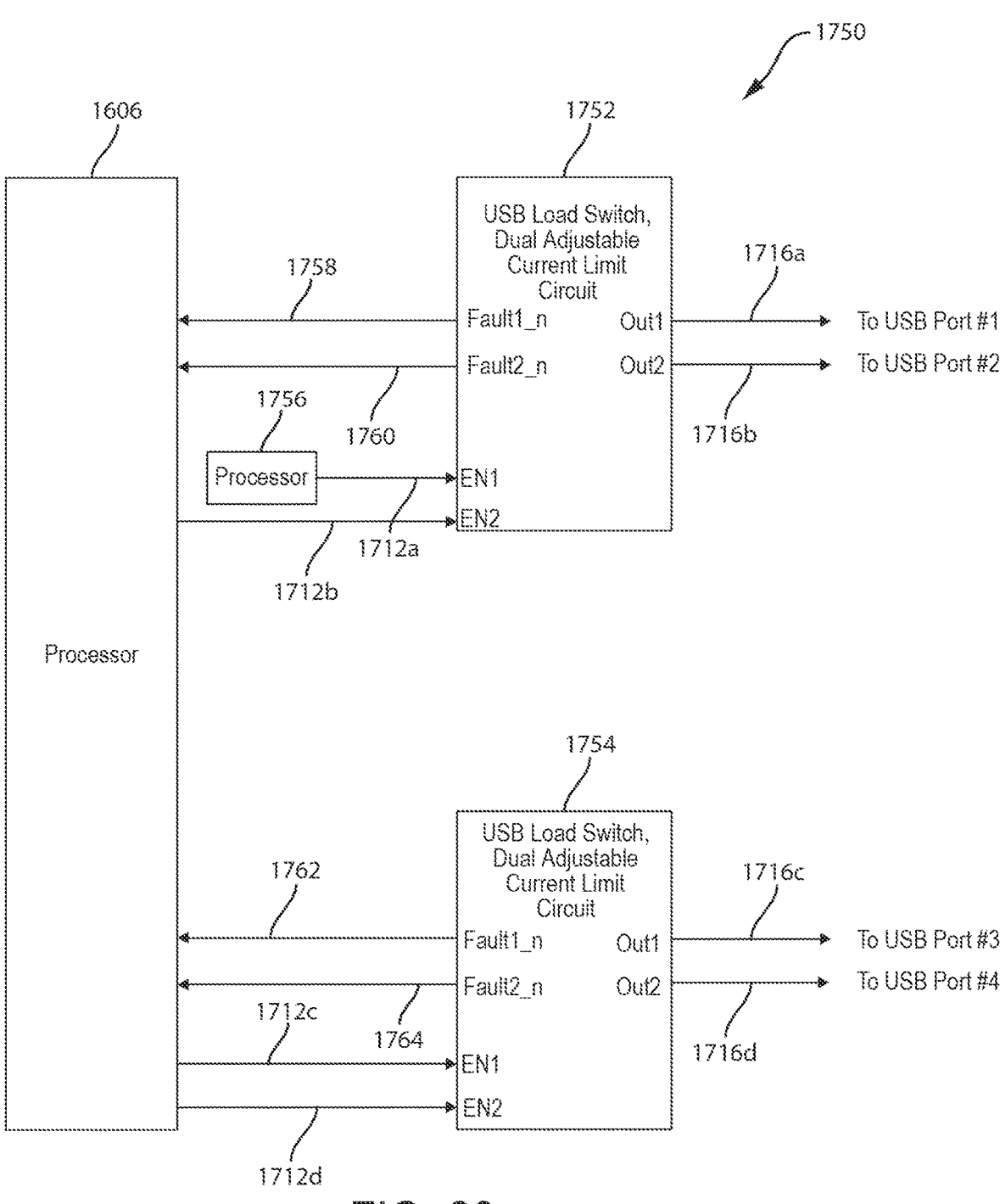
FIG. 28 is a circuit block diagram of a flexible USB power configuration circuit for the modular energy system shown FIG. 27, in accordance with at least one aspect of the present disclosure.

FIG. 28 is a circuit block diagram of a flexible USB power configuration circuit 1750 for the modular energy system 2000, 3000, 6000 shown FIG. 27, in accordance with at least one aspect of the present disclosure. The flexible USB power configuration circuit 1750 comprises a processor 1606 coupled to two dual channel power distribution switches 1752, 1754. Each of the dual channel power distribution switches 1752, 1754 comprises two USB load switches and adjustable current limit circuits that implement the USB power controllers 1714a-1714d shown in FIG. 27. Each of the two USB load switches and adjustable current limit circuits of the first dual channel power distribution switch 1752 are independently enabled/disabled by a standby processor 1756 via enable/disable line 1712a and by the processor 1606 via enable/disable line 1712b. Each of the two USB load switches and adjustable current limit circuits of the second dual channel power distribution switch 1754 are independently enabled/disabled by the processor 1606 via enable/disable lines 1712c, 1712d, respectively. One of the functions of the dual channel power distribution switches 1752, 1754 is to provide USB power fault signals to the processor 1606 via lines 1758, 1760, 1762, 1764. Another function of the dual channel power distribution switches 1752, 1754 is to independently limit current supplied to the USB ports #1-#4 through power output lines 1716a-1716d.

Figure 29:
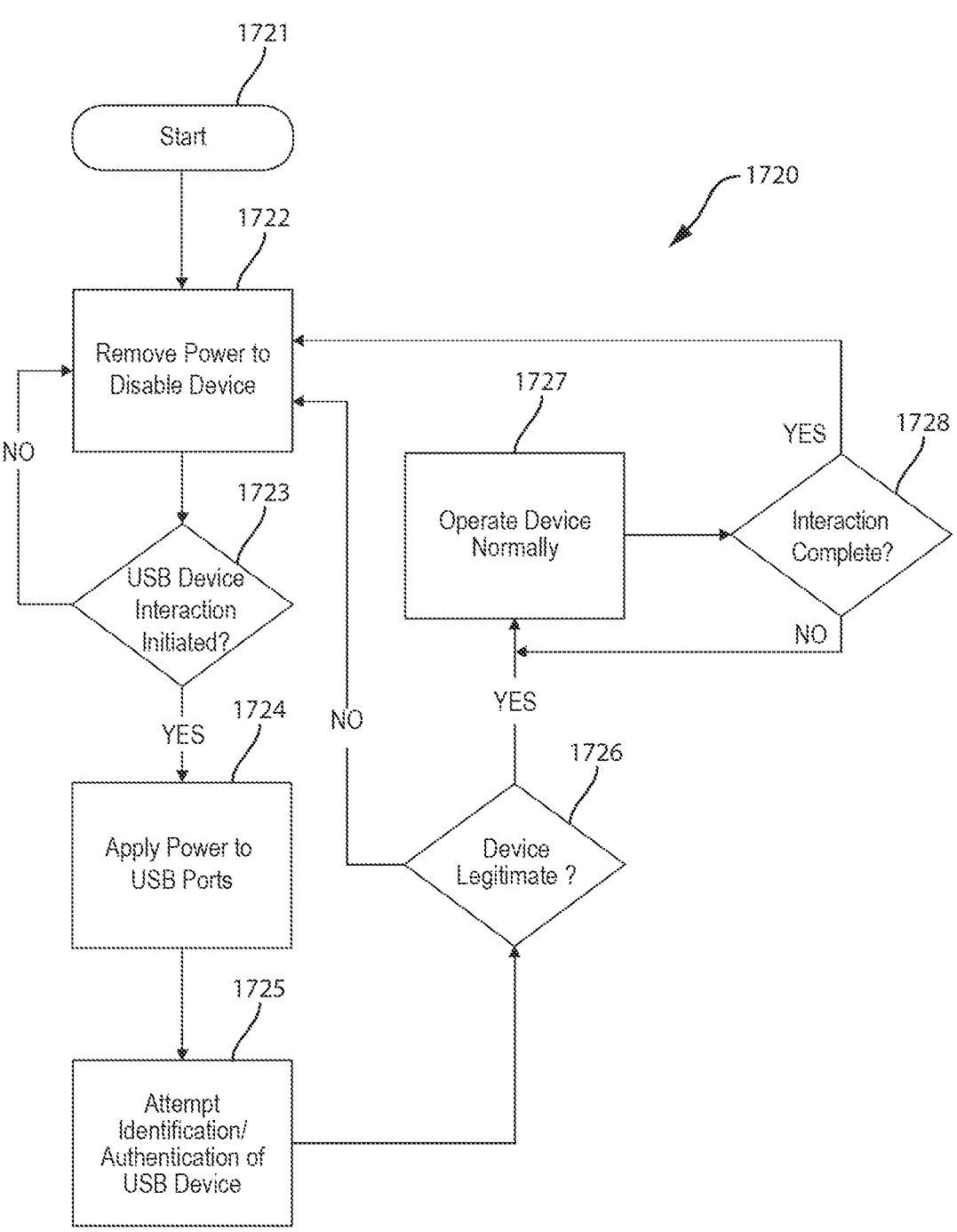
FIG. 29 is logic flow diagram of a method of providing security for a USB device implemented by the flexible USB power configuration circuit shown in FIGS. 27 and 28, in accordance with at least one aspect of the present disclosure.

FIG. 29 is logic flow diagram of a method 1720 of providing security for a USB device implemented by the flexible USB power configuration circuit 1700 shown in FIGS. 27 and 28, in accordance with at least one aspect of the present disclosure. Due to the ubiquity of USB technology, support for USB technology is a major cybersecurity concern. Utilizing the power control capabilities of the flexible USB power configuration circuit 1700 any USB device or peripheral that is detected to be unapproved, unsupported, or unauthenticated may be shut down by the removal of power to the associated USB ports #1-#4 (1718a-1718d) by the processor 1606 of the processor system 1704. This can minimize or eliminate the threat of foul play by a "bad actor" on the USB port #1-#4 (1718a-1718d).

Turning now to FIG. 29, according to the security method 1720, at the start 1721, the processor 1606 removes 1722 power to the USB ports #1-#4 (1718a-1718d) via the USB power controllers 11714a-1714d to disable any USB device that may be plugged into the USB ports #1-#4 (1718a-1718d) and checks if any USB device interaction is initiated 1723. As long as no USB device interaction is initiated 1723 at any of the USB ports #1-#4 (1718a-1718d), the processor 1606 keeps the power removed 1722. In the instance that USB device interaction is initiated 1723 at any one of the USB ports #1-#4 (1718a-1718d), the processor 1606 applies 1724 power to the USB port via the USB power controller 1714a-1714d and attempts identification/authentication 1725 of the USB device. The processor 1606 determines 1726 whether the USB device plugged into any one of the prost #1-#4 (1718a-1718d) is legitimate. If the USB device is not legitimate, the processor 1606 removes 1722 power to disable the illegitimate device. In the instance that the processor 1606 determines 1726 that the USB device is legitimate, the processor 1606 operates 1727 the identified/authenticated USB device normally and allows the exchange of USB data through the USB hub 1708. During the normal operation of the USB device, the processor 1606 determines 1728 whether the interaction is complete and continuously loops until the interaction is complete and the removes 1722 power to the USB port #1-#4 (1718a-1718d) to disable the USB device.

Figure 30:
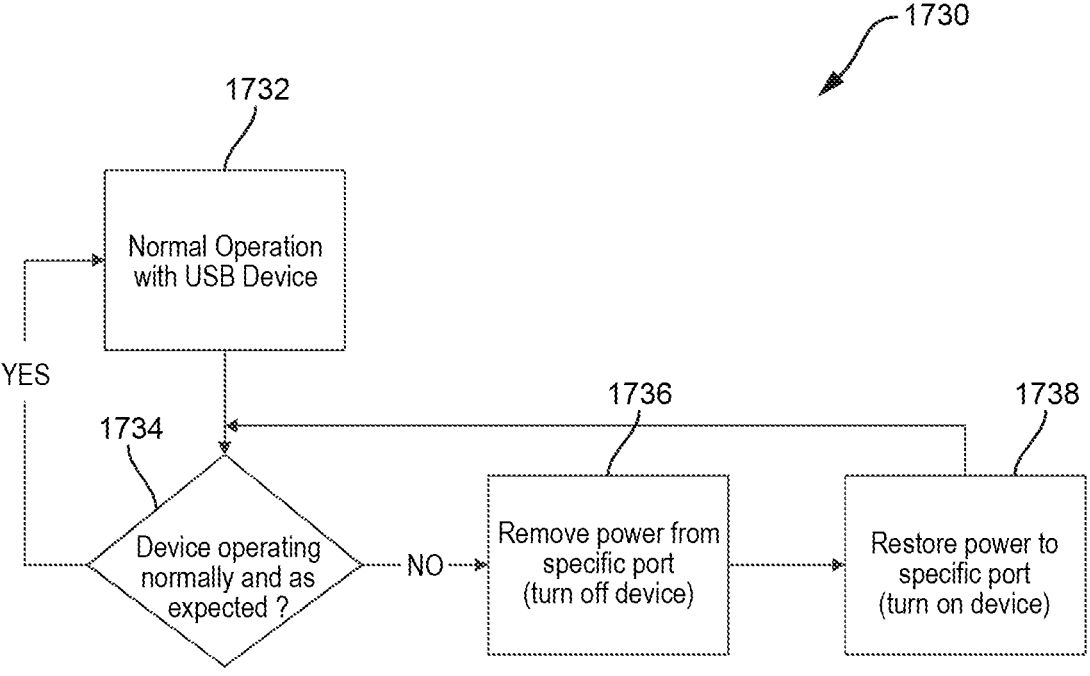
FIG. 30 is a logic flow diagram of a method of recovering from a fault implemented by the flexible USB power configuration circuit shown in FIGS. 27 and 28, in accordance with at least one aspect of the present disclosure.

FIG. 30 is a logic flow diagram of a method 1730 of recovering from a fault implemented by the flexible USB power configuration circuit 1700 shown in FIGS. 27 and 28, in accordance with at least one aspect of the present disclosure. There are intended legitimate uses of the USB ports on the modular energy system 2000, 3000, 6000, including use of approved accessories. In some cases, such peripherals may become integral to the surgical flow requiring high reliability operations. If a device is determined to be malfunctioning, the processor 1606 of the onboard processor system 1704, in an attempt to recover the correct function of the accessory, may briefly remove power from the USB port #1-#4 (1718a-1718d) and restore power shortly thereafter. Power cycling the malfunctioning USB device may restore correct and proper operation of the USB device.

Still with reference to FIG. 30, according to the fault recovery method 1730, during normal operation 1732 of the USB device, the processor 1606 monitors 1734 the operation of the USB device until the processor 1606 determines that the USB device is not operating normally and as expected. The processor 1606 then removes 1736 power from the specific USB port #1-#4 (1718a-1718d) to turn off the USB device. The processor 1606 restores 1738 power to the specific USB port #1-#4 (1718a-1718d) to turn on the USB device for the purpose of monitoring 1734 the operation of the USB device to determine whether correct and proper operation of the USB device has been restored. In the instance that the USB device recovers proper and normal operation as expected, the processor 1606 resumes normal operation 1732 with the USB device. Otherwise, the processor 1606 removes power 1736 from the USB port #1-#4 (1718a-1718d) to turn off the USB device and periodically restores 1738 power to the USB device to determine whether the operation of the USB device has been restored to the correct and proper operation.

Figure 31:
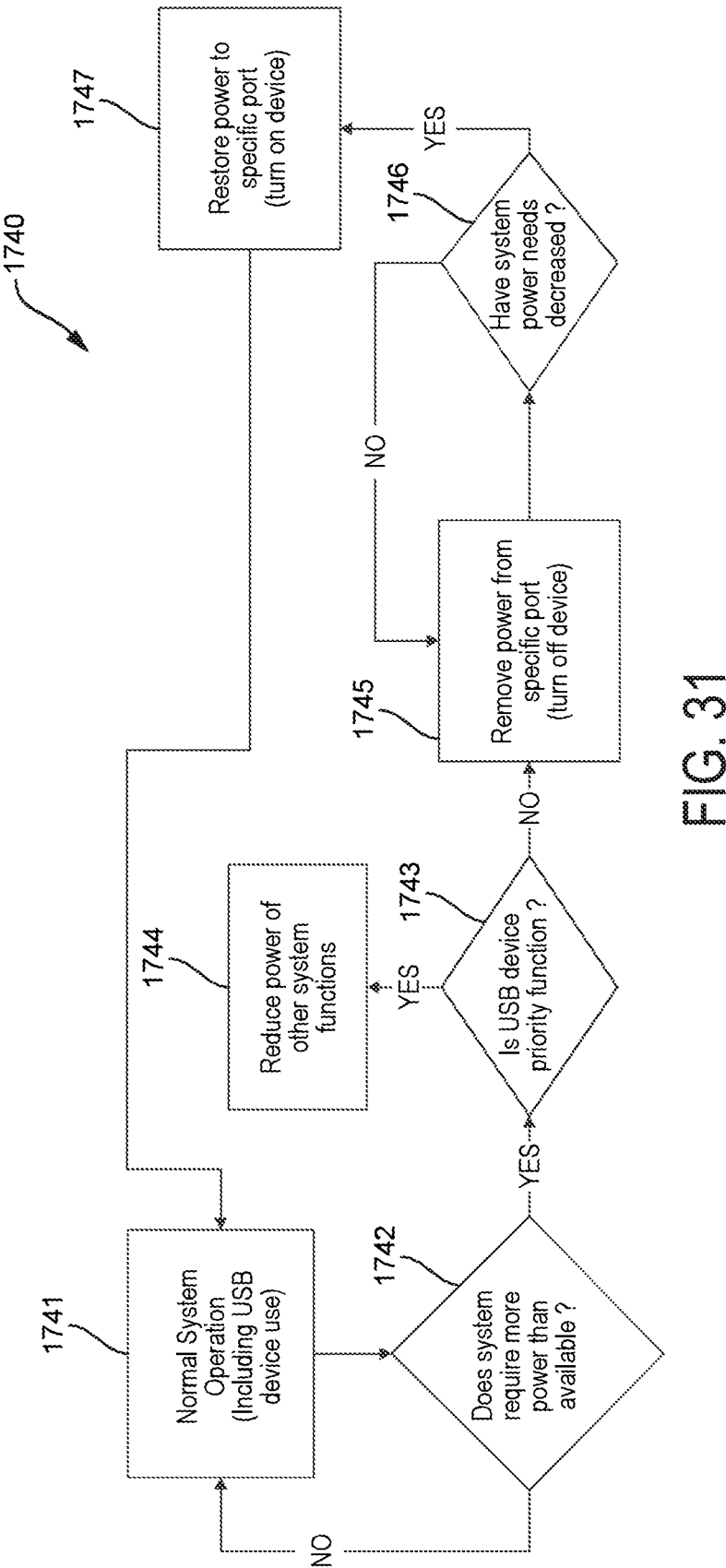
FIG. 31 is a logic flow diagram of a method of budgeting power implemented by the flexible USB power configuration circuit shown in FIGS. 27 and 28, in accordance with at least one aspect of the present disclosure.

FIG. 31 is a logic flow diagram of a method 1740 of budgeting power implemented by the flexible USB power configuration circuit 1700 shown in FIGS. 27 and 28, in accordance with at least one aspect of the present disclosure. In a modular system, such as the modular energy system 2000, 3000, 6000, total available power may be limited to the overall system, leading to constraints on total power consumption at a given moment in time. For example, in a modular energy system 2000, 3000, 6000 with two energy generator modules, such as energy modules 2004a, 2004b discussed above, using both energy generator modules each with a "high power" instrument may limit power available to the rest of the system to a relatively low amount. In such cases, a priority of functions can be determined and power consumption reduced accordingly. In one aspect, a USB peripheral may be less critical to the modular energy system 2000, 3000, 6000 use than another module or even another USB peripheral. To therefore reduce total power consumption by the modular energy system 2000, 3000, 6000, the onboard processor may selectively turn off specific USB peripherals by removing power to the USB peripherals and thus reducing the overall power burden.

Still with reference to FIG. 31, according to the power budgeting method 1740, during normal operation 1741 of the modular energy system 2000, 3000, 6000, including USB device use, the processor 1606 determines 1742 whether the modular energy system 2000, 3000, 6000 requires more power than is available. In the instance the modular energy system 2000, 3000, 6000 requires more power than is available, the processor 1606 determines 1743 the priority function of the USB device. In the instance the USB device is a priority function, the processor 1606 reduces 1744 power to other devices performing lower priority functions. In the instance the processor 1606 determines 1743 that the USB is not a priority function, the processor 1606 removes 1745 power from the specific USB port #1-#4 (1718a-1718d) to turn off or disable the low priority USB device. The processor 1606 then determines 1746 whether the power requirements of the modular energy system 200 have decreased. The processor 1606 maintains power removed from the specific USB port #1-#4 (1718a-1718d) until the modular energy system 2000, 3000, 6000 power requirements have decreased. The processor 1606 then restores 1747 power to the specific USB port #1-#4 (1718a-1718d) and continues to normal operation 1741 of the modular energy system 2000, 3000, 6000.

Remote Power Control Interface for Modular Energy Systems

In one aspect, the present disclosure provides circuits and associated methods for resolving the ability of a master control, such as a robotic system, to command a remote system. The master control can power up or power down the remote system while the remote system may be in a limited functionality operational state (such as "powered down"). Various aspects of the present disclosure provide circuits and associated methods for commanding a remote system, such as the modular energy system 2000, 3000, 6000, to power On/Off.

Figure 32:
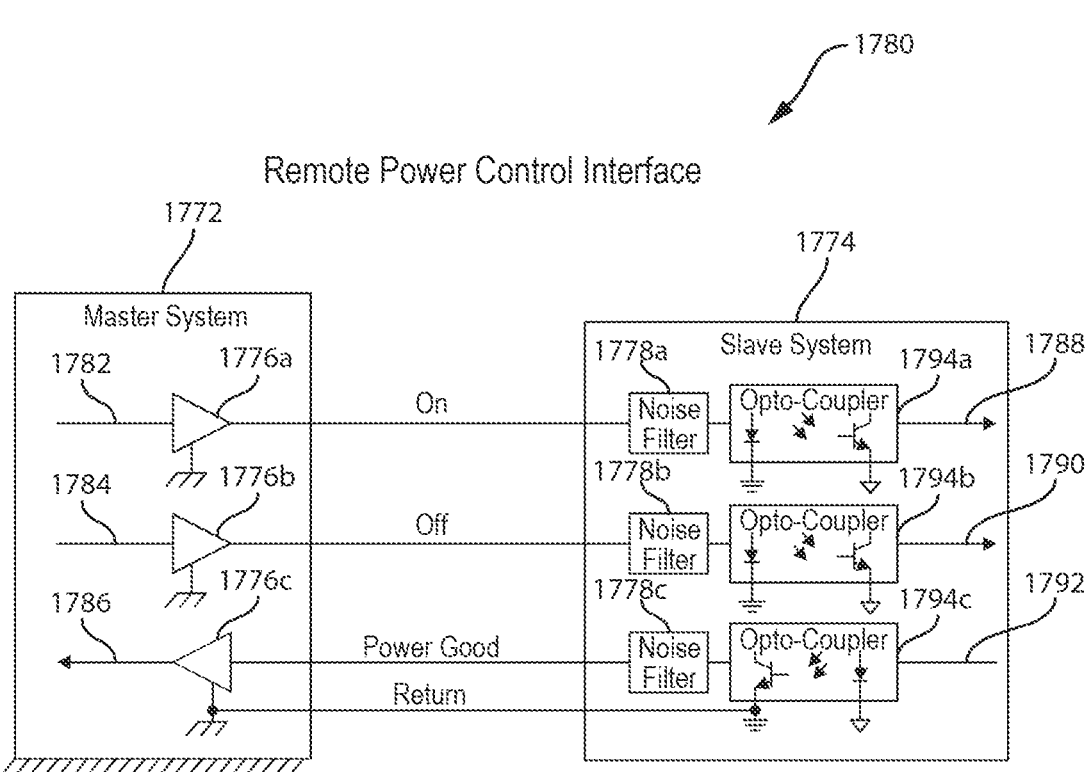
FIG. 32 is a schematic diagram of a remote power control interface circuit for a modular energy system, in accordance with at least one aspect of the present disclosure.

FIG. 32 is a schematic diagram of a remote power control interface circuit 1780 for a modular energy system 2000, 3000, 6000, in accordance with at least one aspect of the present disclosure. In one aspect, the remote power control interface circuit 1780 provides an elegant, isolated, discrete communication technique between two independent systems. One system is the master system 1772 and the other system is the slave system 1774. The local master system 1772 controls the remotely located slave system 1774. In one aspect, the master system 1772 may comprise two driver/buffer circuits 1776a, 1776b and one receiver circuit 1776c, with filter and isolation circuit, for example, coupled to the slave system 1774. The slave system 1774 may comprise two input circuits 1778a, 1778b and one driver/buffer circuit 1778c. In other aspects, the master system 1772 and the slave system 1774 may comprise additional or fewer driver/buffer circuits and filter/isolation circuits. For example, in one aspect, the master system 1772 may comprise at least one driver/buffer circuit 1776a and at least one receiver circuit 1776c, with filter and isolation circuit, for example, and the slave system 1774 may comprise at least one input circuit with noise filter 1778a and at least one driver/buffer circuit 1778c, for example. It will be appreciated that noise filtering for the remote power control interface circuit 1780 can alternatively be implemented digitally in an FPGA or processor circuitry, for example.

In one aspect, the remote power control interface circuit 1780 includes three signals 1782 (On), 1784 (Off), 1786 (Power Good) and a return line. Each signal 1782, 1784, 1786 is independent, with the "On" signal 1782 being the method by which the master system 1772 enables the slave system 1774, the "Off" signal 1784 being the method by which the master system 1772 disables the slave system 1774, and the "Power Good" signal 1786 being a feedback signal from the slave system 1774 to the master system 1772 used by the control system as a status indicator of the slave system 1774.

In one aspect, the slave system 1774 comprises three noise filters 1778a, 1778b, 1778c coupled to the signals 1782, 1784, 1786, respectively. The noise filters 1778a, 1778b, 1778c are coupled to isolation circuits 1780a, 1780b, 1780c, respectively, where the first two noise filters 1778a, 1778b are coupled to the input side of the isolation circuits 1794a, 1794b and the third noise filter 1778c is coupled to the output of the isolation circuit 1794c. In the example illustrated in FIG. 32, the isolation circuits 1794a, 1794b, 1794c are opto-couplers, although other isolation circuits may be employed. The first and second isolation circuits 1794a, 1794b provide isolated outputs 1788, 1790 and the third isolation circuit 1794c receives an input signal 1792.

Electrical isolation at the slave system 1774 prevents ground loops and high immunity to interference in the event the master system 1772 and the slave system 1774 are powered from different power systems with the remote power control interface of claim 16. Pulsed, discrete signaling provides a simple, robust, cost effective means of "On" and "Off" control and a single discrete feedback signal provides continuous feedback to the master system 1772 of the status of the slave system 1774. Also, pulsed discrete signaling provides robustness against "stuck high" and "stuck low" failure modes. In one aspect, the master system 1772 is configured to enable and disable the slave system 1774 by static (or logic-level) discrete signaling.

EXAMPLES

Various aspects of the subject matter described herein are set out in the following numbered examples.

Example 1. An accessory circuit for a modular energy system, the accessory circuit comprising: an accessory port configured to receive an accessory; a power supply; a processor; an isolation barrier configured to electrically isolate the processor and the power supply from the accessory port; a flexible serial communication interface coupled between the processor and the accessory port, the flexible serial communication interface configured to support multiple communication protocols; and a presence detection circuit coupled between the accessory port and the processor, wherein the presence detection circuit is configured to detect presence of an accessory connected to the accessory port.

Example 2. The accessory circuit of Example 1, wherein the processor is configured to determine a malfunctioning or unacceptable accessory and to disable power to the malfunctioning or unacceptable accessory through a current limiter circuit coupled between the power supply and the processor and the accessory port.

Example 3. The accessory circuit of any one or more of Examples 1 through 2, wherein the presence detection circuit detects a presence signal, wherein the presence signal directly configures the flexible serial communication interface as the correct communications protocol.

Example 4. The accessory circuit of any one or more of Examples 1 through 3, comprising a current limiter circuit coupled between the power supply and the processor and the accessory port, the current limiter circuit configured to limit current supplied to an accessory connected to the accessory port.

Example 5. The accessory circuit of any one or more of Examples 1 through 4, wherein the current limiter is an adjustable current limiter circuit configured to power down an accessory determined to be unacceptable by the processor.

Example 6. The accessory circuit of any one or more of Examples 1 through 5, wherein the isolation barrier comprises: at least one digital isolator circuit coupled between the processor and the flexible serial communications interface.

Example 7. The accessory circuit of any one or more of Examples 1, wherein the presence detection circuit is configured to signal the presence of an accessory to the processor and the processor is configured to budget power delivered to the accessory.

Example 8. The accessory circuit of any one or more of Examples 1 through 7, wherein the processor is configured to determine which protocol to use to communicate with an accessory based on a signal from the presence detection circuit.

Example 9. A flexible serial bus power configuration circuit for a modular energy system, the flexible serial bus power configuration circuit comprising: a processor system; a serial bus hub coupled to the processor system; at least two serial bus power controllers, wherein each of the at least two serial bus controllers is independently coupled to the processor system; and a serial bus port configurable in a first or second mode, the serial bus port configured to independently receive a serial bus device, wherein the serial bus hub is coupled to the serial bus port, and wherein one of the at least two serial bus power controllers is coupled to the serial bus port configured in a first mode, and wherein another of the at least two serial bus power controllers is coupled to the serial bus port configured in a second mode; and wherein the processor system is configured to individually control each of the at least two serial bus power controllers to control power applied to the serial bus port.

Example 10. The flexible serial bus power configuration circuit of Example 9, wherein each of the least two serial bus power controllers comprises: a serial bus load switch; and an adjustable current limit circuit.

Example 11. The flexible serial bus power configuration circuit of any one or more of Examples 9 through 10, wherein the serial bus load switch and the adjustable current limit circuit are configured to provide power fault signals to the processor system.

Example 12. The flexible serial bus power configuration circuit of any one or more of Examples 9 through 11, wherein the serial bus load switch and the adjustable current limit circuit are configured to independently limit current supplied to the serial bus port.

Example 13. The flexible serial bus power configuration circuit of any one or more of Examples 9 through 12, wherein the processor system is configured to authenticate a serial bus device connected to the serial bus port and remove power from an unauthenticated serial bus device.

Example 14. The flexible serial bus power configuration circuit of any one or more of Examples 9 through 13, comprising an additional processor configured to control one of the at least two serial bus power controllers, wherein the processor is configured to control the other one of the at least two serial bus power controllers.

Example 15. The flexible serial bus power configuration circuit of any one or more of Examples 9 through 14, wherein the processor system is configured to: detect connection of a new serial bus device to the serial bus port; determine authenticity of the connected new serial bus device; and operate a legitimate connected new serial bus device normally; and remove power to an illegitimate connected new serial bus device.

Example 16. The flexible serial bus power configuration circuit of Example 15, wherein the processor system is configured to: determine unexpected operation of the legitimate connected new serial bus device; remove power from the serial bus port where the legitimate connected new serial bus device is connected; and restore power to the serial bus port.

Example 17. The flexible serial bus power configuration circuit of any one or more of Examples 15 through 16, wherein the processor system is configured to: determine power requirement of the modular energy system; determine priority function of the legitimate connected new serial bus device; remove power supplied to the serial bus port where the legitimate connected new serial bus device is connected for a low priority legitimate connected new serial bus device; and reduce power supplied to the modular energy system for a high priority legitimate connected new serial bus device.

Example 18. A remote power control interface for a modular energy system, the remote power control interface comprising: a master system comprising at least one driver/buffer circuit and one input circuit; and a slave system located remotely from the master system, the slave system comprising at least one driver/buffer circuit and at least one input circuit; wherein the master is configured to enable and disable the slave system.

Example 19. The remote power control interface of Example 18, wherein the master system is configured to enable and disable the slave system by pulsed, discrete signaling.

Example 20. The remote power control interface of any one or more of Examples 18 through 19, wherein the master system is configured to enable and disable the slave system by static or logic-level discrete signaling.

Example 21. The remote power control interface of any one or more of Examples 18 through 20, wherein the slave system is configured to send a continuous feedback signal to the master system to indicate a status of the slave system.

Example 22. The remote power control interface of any one or more of Examples 18 through 21, wherein the master system and the slave system are powered from separate power supplies.

Example 23. The remote power control interface of any one or more of Examples 18 through 22, wherein the slave system comprises at least one noise filter circuit and at least one isolation circuit.

Example 24. The remote power control interface of any one or more of Examples 18 through 23, wherein the least one driver/buffer circuit of the slave system is coupled to a first isolation circuit and the at least one input circuit of the slave system is coupled to a second isolation circuit.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. An accessory circuit for a modular energy system, the accessory circuit comprising:
   an accessory port configured to receive:
      a first accessory associated with a first serial communication protocol; and
      a second accessory associated with a second serial communication protocol, wherein the first serial communication protocol is different from the second communication protocol;
   a power supply;
   a processor;
   a current limiter circuit coupled between the power supply and the accessory port, the current limiter circuit configured to limit a current drawn by at least one of the first accessory and the second accessory coupled to the accessory port based on receiving an enable signal from the processor;
   an isolation barrier configured to electrically isolate the processor and the power supply from the current limiter circuit and the accessory port;
   a flexible serial communication transceiver coupled between the processor and the accessory port, wherein the processor is capable of configuring the flexible serial communication transceiver according to a first configuration that supports the first serial communication protocol and a second configuration that supports the second serial communication protocol; and
   a presence detection circuit coupled between the accessory port and the processor, wherein the presence detection circuit is configured to:
      cause the processor to configure the flexible serial communication transceiver according to the first serial communication protocol based on detecting connection of the first accessory to the accessory port; and
      cause the processor to configure the flexible serial communication transceiver according to the first serial communication protocol based on detecting connection of the second accessory to the accessory port.

2. The accessory circuit of claim 1, wherein the processor is configured to determine a malfunctioning or unacceptable accessory and to disable power to the malfunctioning or unacceptable accessory based on transmitting the enable signal to the current limiter circuit.

3. The accessory circuit of claim 1, wherein the presence detection circuit is configured to detect the connection of the first accessory to the accessory port based on detecting a presence signal, and wherein the processor sends a protocol selection signal to the flexible serial communication transceiver to configure the flexible serial communication transceiver according to the first serial communication protocol.

4. The accessory circuit of claim 2, wherein the current limiter circuit is an adjustable current limiter circuit.

5. The accessory circuit of claim 1, wherein the isolation barrier comprises:

at least one digital isolator circuit to electrically isolate the processor and the power supply from the current limiter circuit and the flexible serial communications transceiver.

6. The accessory circuit of claim 1, wherein the presence detection circuit is configured to signal the presence of the first accessory to the processor and the processor is configured to budget power delivered to the first accessory.

7. The accessory circuit of claim 1, wherein the processor is configured to determine which serial communications protocol of the first serial communication protocol and the second serial communication protocol to configure the flexible serial communication transceiver according to based on receiving a signal from the presence detection circuit.

8. A module for use in a modular energy system, the module comprising:

an instrument port for coupling a surgical instrument to the modular energy system;

an accessory port for coupling a first accessory and a second accessory to the modular energy system;

a power supply;

a processor;

a current limiter circuit coupled between the power supply and the accessory port, the current limiter circuit configured to limit a current drawn by at least one of the first accessory and the second accessory coupled to the accessory port based on receiving an enable signal from the processor;

an isolation barrier configured to electrically isolate the processor and the power supply from the current limiter circuit and the accessory port;

a flexible serial communication transceiver coupled between the processor and the accessory port, the flexible serial communication transceiver configurable to support multiple serial communication protocols, wherein the multiple serial communications protocols comprise a first serial communication protocol and a second serial communication protocol, and wherein the processor is capable of configuring the flexible serial communication transceiver according to a first configuration that supports the first serial communication protocol and a second configuration that supports the second serial communication protocol; and a presence detection circuit coupled between the accessory port and the processor, wherein the presence detection circuit is configured to;

cause the processor to configure the flexible serial communication transceiver according to the first serial communication protocol based on detecting coupling of the first accessory to the accessory por; and cause the processor to configure the flexible serial communication transceiver according to the first serial communication protocol based on detecting coupling of the second accessory to the accessory port.

9. The module of claim 8, wherein the processor is configured to determine a malfunctioning or unacceptable accessory and to disable power to the malfunctioning or unacceptable accessory based on transmitting the enable signal to the current limiter circuit.

10. The module of claim 8, wherein the presence detection circuit is configured to detect the connection of the first accessory to the accessory port based on detecting a presence signal, and wherein the processor sends a protocol selection signal to the flexible serial communication transceiver to configure the flexible serial communication transceiver according to the first serial communication protocol.

11. The module of claim 9, wherein the current limiter circuit is an adjustable current limiter circuit.

12. The module of claim 8, wherein the isolation barrier comprises:

at least one digital isolator circuit to electrically isolate the processor and the power supply from the current limiter circuit and the flexible serial communications transceiver.

13. The module of claim 8, wherein the presence detection circuit is configured to signal the presence of an accessory to the processor and the processor is configured to budget power delivered to the accessory.

14. The module of claim 8, wherein the processor is configured to determine which serial communications protocol of the multiple serial communications protocols to use based on a signal from the presence detection circuit.

15. A modular energy system, comprising:

an energy module comprising an instrument port for coupling a surgical instrument to the modular energy system, wherein the energy module is to deliver power for driving an energy mode of the surgical instrument via the instrument port; and a header module couplable to the energy module, the header module comprising:

an accessory port for coupling a first accessory and a second accessory to the modular energy system;

a power supply;

a processor;

a current limiter circuit coupled between the power supply and the accessory port, the current limiter circuit configured to limit a current drawn by at least one of the first accessory and the second accessory coupled to the accessory port based on receiving an enable signal from the processor;

an isolation barrier configured to electrically isolate the processor and the power supply from the current limiter circuit and the accessory port;

a flexible serial communication transceiver coupled between the processor and the accessory port, the flexible serial communication transceiver configurable to support multiple serial communication protocols, wherein the multiple serial communications protocols comprise a first serial communication protocol and a second serial communication protocol, and wherein the processor is capable of configuring the flexible serial communication transceiver according to a first configuration that supports the first serial communication protocol and a second configuration that supports the second serial communication protocol; and a presence detection circuit coupled between the accessory port and the processor, wherein the presence detection circuit is configured to:

cause the processor to configure the flexible serial communication transceiver according to the first serial communication protocol based on detecting coupling of the first accessory to the accessory port; and cause the processor to configure the flexible serial communication transceiver according to the first serial communication protocol based on detecting coupling of the second accessory to the accessory port.

16. The module of claim 15, wherein the processor is configured to determine a malfunctioning or unacceptable accessory and to disable power to the malfunctioning or unacceptable accessory based on transmitting the enable signal to the current limiter circuit.

17. The module of claim 15, wherein the presence detection circuit is configured to detect the connection of the first accessory to the accessory port based on detecting a presence signal, and wherein the processor sends a protocol selection signal to the flexible serial communication transceiver to configure the flexible serial communication transceiver according to the first serial communication protocol.

\* \* \* \* \*